(12) United States Patent
Chaum et al.

(10) Patent No.: US 11,375,929 B2
(45) Date of Patent: Jul. 5, 2022

(54) METHOD AND DEVICE FOR DETECTION OF BIOAVAILABLE DRUG CONCENTRATION IN A FLUID SAMPLE

(71) Applicants: THE UNIVERSITY OF TENNESSEE RESEARCH FOUNDATION, Knoxville, TN (US); THE UNIVERSITY OF MEMPHIS RESEARCH FOUNDATION, Memphis, TN (US)

(72) Inventors: Edward Chaum, Memphis, TN (US); Erno Lindner, Germantown, TN (US)

(73) Assignees: THE UNIVERSITY OF TENNESSEE RESEARCH FOUNDATION, Knoxville, TN (US); THE UNIVERSITY OF MEMPHIS RESEARCH FOUNDATION, Memphis, TN (US)

( * ) Notice: Subject to any disclaimer, the term of this patent is extended or adjusted under 35 U.S.C. 154(b) by 695 days.

(21) Appl. No.: 15/989,765

(22) Filed: May 25, 2018

(65) Prior Publication Data
US 2018/0271413 A1 Sep. 27, 2018

Related U.S. Application Data

(63) Continuation-in-part of application No. 15/611,089, filed on Jun. 1, 2017, now abandoned, and a
(Continued)

(51) Int. Cl.
*A61B 5/1468* (2006.01)
*A61B 5/145* (2006.01)
(Continued)

(52) U.S. Cl.
CPC .......... *A61B 5/1468* (2013.01); *A61B 5/053* (2013.01); *A61B 5/1459* (2013.01);
(Continued)

(58) Field of Classification Search
CPC ...... G01N 27/49; G01N 27/404; G01N 33/00; G01N 27/327; G01N 27/333;
(Continued)

(56) References Cited

U.S. PATENT DOCUMENTS

| 3,856,649 A | 12/1974 | Genshaw et al. |
| 4,053,381 A | 10/1977 | Hamblen et al. |

(Continued)

FOREIGN PATENT DOCUMENTS

| WO | 2006/0040588 | 4/2006 |
| WO | 2008/030582 | 3/2008 |
| WO | 2010/045465 | 4/2010 |

OTHER PUBLICATIONS

Absalom et al "Pharmacokinetic models for propofol—defining and illuminating the devil in the detail," Br J Anaesth. Jul. 2009;103(1):26-37.
(Continued)

*Primary Examiner* — Eric J Messersmith
(74) *Attorney, Agent, or Firm* — Baker Donelson

(57) ABSTRACT

The invention relates to a method for the controlled delivery of a drug as a function of bioavailable drug concentration, a sensor device for detecting bioavailable drug concentration, and a delivery device that controls delivery of the drug based on the real-time detection of bioavailable drug concentration.

20 Claims, 56 Drawing Sheets

Related U.S. Application Data continuation-in-part of application No. 14/404,674, filed as application No. PCT/US2013/031757 on Mar. 14, 2013, now Pat. No. 9,983,162, which is a continuation-in-part of application No. 13/124,036, filed as application No. PCT/US2009/060852 on Oct. 15, 2009, now Pat. No. 9,700,246.

(60) Provisional application No. 61/654,469, filed on Jun. 1, 2012, provisional application No. 61/105,604, filed on Oct. 15, 2008.

(51) Int. Cl.
| | |
|---|---|
| A61B 5/053 | (2021.01) |
| A61B 5/00 | (2006.01) |
| A61M 5/172 | (2006.01) |
| A61M 5/142 | (2006.01) |
| A61M 5/145 | (2006.01) |
| A61B 5/1459 | (2006.01) |
| G01N 27/49 | (2006.01) |
| A61M 25/00 | (2006.01) |
| A61M 31/00 | (2006.01) |
| G01N 27/403 | (2006.01) |
| G01N 33/00 | (2006.01) |

(52) U.S. Cl.
CPC ...... *A61B 5/14539* (2013.01); *A61B 5/14546* (2013.01); *A61B 5/4839* (2013.01); *A61M 5/1452* (2013.01); *A61M 5/14216* (2013.01); *A61M 5/172* (2013.01); *G01N 27/49* (2013.01); *A61B 5/6852* (2013.01); *A61L 2300/402* (2013.01); *A61M 25/0017* (2013.01); *A61M 31/002* (2013.01); *A61M 2205/3303* (2013.01); *A61M 2205/3576* (2013.01); *A61M 2205/502* (2013.01); *A61M 2205/52* (2013.01); *G01N 27/403* (2013.01); *G01N 33/00* (2013.01)

(58) Field of Classification Search
CPC ... G01N 27/3275; A61M 5/142; A61M 5/172; A61M 5/1723; A61M 2202/048
See application file for complete search history.

(56) References Cited

U.S. PATENT DOCUMENTS

| | | | |
|---|---|---|---|
| 4,280,494 A | | 7/1981 | Cosgrove, Jr. et al. |
| 4,381,011 A | * | 4/1983 | Somers, III ........ A61B 5/14539 600/350 |
| 4,409,980 A | * | 10/1983 | Yano .................. A61B 5/14542 204/406 |
| 4,533,346 A | | 8/1985 | Cosgrove, Jr. et al. |
| 4,711,703 A | * | 12/1987 | Wright ................. G01N 27/404 165/177 |
| 4,869,264 A | | 9/1989 | Silberstein |
| 5,094,235 A | | 3/1992 | Westenskow et al. |
| 5,212,050 A | | 5/1993 | Mier et al. |
| 5,554,339 A | | 9/1996 | Cozzette et al. |
| 5,649,531 A | | 7/1997 | Heinonen |
| 5,830,341 A | | 11/1998 | Gilmartin |
| 6,631,291 B2 | | 10/2003 | Viertio-Oja et al. |
| 6,646,071 B1 | | 11/2003 | Klosin et al. |
| 6,691,705 B2 | | 2/2004 | Dittmann et al. |
| 6,745,764 B2 | | 6/2004 | Hickle |
| 6,757,558 B2 | | 6/2004 | Lange et al. |
| 7,108,680 B2 | | 9/2006 | Rohr et al. |
| 7,182,847 B1 | * | 2/2007 | Millar .................. G01N 27/333 204/433 |
| 7,220,240 B2 | | 5/2007 | Struys et al. |
| 7,364,552 B2 | | 4/2008 | Kiesele et al. |
| 7,630,747 B2 | | 12/2009 | Corl et al. |
| 9,700,246 B2 | | 7/2017 | Chaum et al. |
| 2003/0209450 A1 | | 11/2003 | McVey et al. |
| 2003/0212441 A1 | | 11/2003 | Starkweather et al. |
| 2004/0103897 A1 | | 6/2004 | Hickle et al. |
| 2004/0217017 A1 | | 11/2004 | Kidwell |
| 2005/0022811 A1 | | 2/2005 | Kiesele et al. |
| 2005/0054905 A1 | * | 3/2005 | Corl .................. A61B 5/14539 600/309 |
| 2006/0004271 A1 | | 1/2006 | Peyser et al. |
| 2006/0167722 A1 | | 7/2006 | Struys et al. |
| 2007/0060874 A1 | | 3/2007 | Nesbitt et al. |
| 2007/0078373 A1 | | 4/2007 | Sharma et al. |
| 2007/0118075 A1 | | 5/2007 | Uutela et al. |
| 2007/0134721 A1 | | 6/2007 | Laitenberger et al. |
| 2007/0203448 A1 | | 8/2007 | Melker et al. |
| 2008/0000290 A1 | | 1/2008 | Nagels et al. |
| 2008/0021436 A1 | * | 1/2008 | Wolpert ............. A61M 5/1723 604/504 |
| 2008/0086042 A1 | * | 4/2008 | Brister ................. A61B 5/6848 600/347 |
| 2008/0176271 A1 | | 7/2008 | Silver et al. |
| 2008/0200789 A1 | | 8/2008 | Brister et al. |
| 2009/0124964 A1 | * | 5/2009 | Leach .................. A61B 5/0215 604/66 |
| 2009/0177146 A1 | | 7/2009 | Nesbitt et al. |
| 2009/0277805 A1 | | 11/2009 | Amemiya et al. |
| 2010/0010328 A1 | * | 1/2010 | Nguyen ............... A61B 5/6852 600/354 |
| 2010/0173421 A1 | | 7/2010 | Piletsky et al. |
| 2010/0331644 A1 | * | 12/2010 | Neale ....................... A61N 1/05 600/345 |
| 2011/0118583 A1 | * | 5/2011 | Yuasa .................... A61B 5/412 600/377 |
| 2012/0116195 A1 | * | 5/2012 | Chaum ............... A61B 5/4839 600/345 |
| 2015/0119848 A1 | * | 4/2015 | Chaum ................ G01N 27/333 604/504 |
| 2017/0196488 A1 | * | 7/2017 | Hofius ................. A61B 5/6852 |
| 2017/0370880 A1 | | 12/2017 | Chaum et al. |
| 2019/0331656 A1 | * | 10/2019 | Chaum ............. G01N 27/3275 |

OTHER PUBLICATIONS

Amemiya et al, "Electrochemical heparin sensing at liquid/liquid interfaces and polymeric membranes." Anal. Bioanal. Chem. 399:571-579 (2011).

Ammann et al, "Lipophilic salts as membrane additives and their influence on the properties of macro- and micro-electrodes based on neutral carriers" Analytica Chimica Acta 171 : 119-129 (1985).

Armstrong et al, "Properties of PVC based membranes used in ion-selective electrodes," Electrochim. Acta 35: 1-7 (1990).

Arumugam et al., "Wafer-scale fabrication of patterned carbon nanofiber nanoelectrode arrays: A route for development of multiplexed, ultrasensitive disposable biosensors," Biosensors Bioelectronics 24(9): 2818-2824 (2009).

Azevedo et al. "Detection of phenol at boron-doped nanocrystalline diamond electrodes," J. Electroanal. Chem. 658:38-45 (2011).

Bard and Falkner, Electrochemical Methods, John Wiley and Sons, New York (2001).

Bhattacharya et al, "Binding of the General Anesthetics Propofol and Halothane to Human Serum Albumin," J. Biol. Chem. 275:38731-38738 (2000).

Blanco et al, "Microfluidic-optical Integrated CMOS Compatible Devices for Label-free Biochemical Sensing," J Micromechanics Microengineering 16: 1006-1016 (2006).

Bodor et al, "Electrochemical methods for the determination of the diffusion coefficient of ionophores and ionophore-ion complexes in plasticized PVC membranes," Analyst 133 :635-642 (2008).

Brookes, Benjamin A., et al. "Voltammetric sensing of thiols. The electrocatalytic oxidation of 4-acetamidophenol in the presence of cysteine: A mechanistic rotating disk electrode study." The Journal of Physical Chemistry B 105.27 (2001): 6361-6366.

CA Office Action dated Oct. 14, 2016; CA 2,740,421.
CA Office Action dated Dec. 4, 2015; CA 2,740,421.

(56) References Cited

OTHER PUBLICATIONS

Casati et al. "Clinical Assessment of Target-controlled Infusion of Propofol During Monitored Anesthesia Care," Can J Anesth 46(3):235-239 (1999).
Chen & Weber, "A high-throughput method for lipophilicity measurement," Anal. Chem. 79: 1043-1049 (2007).
Chen and Lee, "A Bonding Technique using Hydrophilic SU-8," J Micromechanics Microengineering 17: 1978-1984 (2007).
Chen et al, "Computation of Transient Flow Rates in Passive Pumping Micro-fluidic Systems," Lab. Chip. 9: 107-114 (2009).
Chen et al, "Lab-on-Chip Flow Injection Analysis System without an External Pump and Valves and Integrated with an in Line Electrochemical Detector," Anal. Chem. 81 :9955-9960 (2009).
Chen et al., "A comparison between target-controlled and manually controlled propofol infusions in patients undergoing routine surgical procedures," Eur J Anaesthesiol. Nov. 2009;26(11):928-35.
Chen et al., "The Stability of Radio-Frequency Plasma Treated Polydimethylsiloxane Surface," Langmuir 23(6):3118-3122 (2007).
Coppens et al., "Study of the time course of the clinical effect of propofol compared with the time course of the predicted effect-site concentration: Performance of three pharmacokinetic-dynamic models" Br J Anaesth. Apr. 2010;104(4):452-8.
Delamarche et al, "Stability of Molded polydimethylsiloxane," Adv. Materials 9:741-746 (1997).
Diprifusor manual: Target Controlled Infusion (TCI) in Anaesthetic Practice, AstraZeneca pp. 1-59 (1999).
Drugs.com Internet site (2012).
Engbers et al., "Pharmacokinetic models for propofol: defining and illuminating the devil in the detail." Br J Anaesth. Feb. 2010;104(2):261-4.
Enlund, Mats "TCI: Target Controlled Infusion, or Totally Confused Infusion? Call for an Optimised Population Based Pharmacokinetic Model for Propofol," Upsala J Med Sci 113(2):161-170 (2008).
EP Search report dated Jun. 20, 2017 (EP 13 798 117.1).
European Search Report for corresponding European Application No. 09821258.2 (dated Oct. 30, 2014).
European Search Report for corresponding European Application No. 18809058.3 (dated Feb. 10, 2021).
Fletcher et al. "Transfer of Flexible Arrays of Vertically Aligned Carbon Nanofiber Electrodes to Temperature-Sensitive Substrates." Advanced Materials 18.13 (2006): 1689-1694.
Geertsma et al. "New and Emerging Medical Technologies: A Horizon Scan of Opportunities and Risks," RIVM Report 65/07:59-63 (2007).
Glen et al, "The Development of 'Diprifusor' : A TCI System for Propofol," Anesthesia, 53,Supplement 1, pp. 13-21 (1998).
Gray et al, "Development of the Technology for 'Diprifusor' TCI Systems," Anesthesia, 53, Suppl. 1, pp. 22-27 (1998).
Grossherr M, Hengstenberg A, Meier T, Dibbelt L, Igl BW, Ziegler A, Schmucker P, Gehring H. Propofol concenlration in exhaled air and arterial plasma in mechanically ventilated patients undergoing cardiac surgery. Br J Anaesth. May 2009;102(5):608-13.
Grossherr, Martin, et al. "Discontinuous monitoring of propofol concentrations in expired alveolar gas and in arterial and venous plasma during artificial ventilation." The Journal of the American Society of Anesthesiologists 104.4 (2006): 786-790.
Guillorn et al. "Individually addressable vertically aligned carbon nanofiber-based electrochemical probes." Journal of Applied Physics 91.6 (2002): 3824-3828.
Guo et al, "Voltammetric heparin-selective electrode based on thin liquid membrane with conducting polymer-modified solid support." Anal. Chem. Oct. 1, 2006;78(19):6893-902.
Harrison, G. R., et al. "Real-time breath monitoring of propofol and its volatile metabolites during surgery using a novel mass spectrometric technique: a feasibility study." British journal of anaesthesia 91.6 (2003): 797-799.
Horváth, Viola, and George Horvai. "Cyclic voltammetric experiments with plasticized PVC membranes." Analytica chimica acta 273.1-2 (1993): 145-152.

Huang et al. "Microelectrode arrays for electrochemistry: Approaches to fabrication." Small 5.7 (2009): 776-788.
International Search Report for PCT/US2018/035313, dated Aug. 3, 2018.
Justin M. Zook, Jan Langmaier, Ern Lindner, Current-polarized ion-selective membranes: The influence of plasticizer and lipophilic background electrolyte on concentration profiles, resistance, and voltage transients, Sensors and Actuators B: Chemical, vol. 136, Issue 2, Mar. 2, 2009, pp. 410-418, ISSN 0925-4005, http://dx.doi.org/10.1016/j.snb.
Kim, Min Ah, and Won-Yong Lee. "Amperometric phenol biosensor based on sol-gel silicate/Nafion composite film." Analytica Chimica Acta 479.2 (2003): 143-150.
Kivlehan, et al. "Toward Feedback-Controlled Anesthesia: Voltammetric Measurement of Propofol (2, 6-Diisopropylphenol) in Serum-Like Electrolyte Solutions." Analytical Chemistry. 2012. vol. 84, p. 7670-7676.
Krasowski, Matthew D., et al. "General anesthetic potencies of a series of propofol analogs correlate with potency for potentiation of ?-aminobutyric acid (GABA) current at the GABAA receptor but not with lipid solubility." Journal of Pharmacology and Experimental Therapeutics 297.1 (2001): 338-351.
Langmaier J, Garay F, Kivlehan F, Chaum E, Lindner E. Electrochemical quantification of 2,6-diisopropylphenol (propofol). Anal Chim Acta. Oct. 17, 2011;704(1-2):63-7.
Lee et al. "An aqueous-based surface modification of poly (dimethylsiloxane) with poly (ethylene glycol) to prevent biofouling." Langmuir 21.25 (2005): 11957-11962.
Leslie et al. Target-controlled Infusion Versus Manually-controlled Infusion of Propofol for General Anaesthesia of Sedation in Adults, Cochrane Database of Systematic Reviews 2: 1-33 (2008).
Lund and Hammerich, Organic Electrochemistry, 4th Revised and Expanded Revision, Marcel Dekker, Inc, New York, 2001.
Mazzi, G., and M. Schinella. "Simple and practical high-performance liquid chromatographic assay of propofol in human blood by phenyl column chromatography with electrochemical detection." Journal of Chromatography B: Biomedical Sciences and Applications 528 (1990): 537-541.
McDonald et al, "Fabrication of Micro fluidic Systems in poly(dimethylsiloxane)," Electrophoresis 21 :27-40 (2000).
McKeage and Perry. "Propofol: a review of its use in intensive care sedation of adults." CNS drugs 17.4 (2003): 235-272.
McKnight et al. "Effects of microfabrication processing on the electrochemistry of carbon nanofiber electrodes." The Journal of Physical Chemistry B 107.39 (2003): 10722-10728.
Melechko et al. "Vertically aligned carbon nanofibers and related structures: controlled synthesis and directed assembly." Journal of applied physics 97.4 (2005): 041301.
Miekisch et al., "Assessment of propofol concentrations in human breath and blood by means of HS-SPME-GC-MS" Clin Chim Acta. Sep. 2008;395(1-2):32-7.
Mijatovic et al, "Technologies for Nanofluidic Systems: Top-down vs. Bottom-up—A Review," Lab on a Chip 5:492-500 (2005).
Mohr, "Polymer fir optical sensors," Optical Chemical Sensors, vol. 224, pp. 297-321 (2006).
Nablo, et al. "Sol-Gel Derived Nitric-Oxide Releasing Materials that Reduce Bacterial Adhesion." Journal of American Chemical Society. vol. 123, No. 39. 2001. pp. 9712-9713.
Nieman et al., "Neutral carrier potassium-selective electrodes with low resistances," Analytica Chimica Acta 170:359-363 (1985).
Nordstrom et al, "Rendering SU-8 Hydrophilic to Facilitate use in Micro Channel Fabrication," J Micromechanics Microengineering 14: 1614-1617 (2004).
PCT International Search Report and Written Opinion for PCT/US2009/060852 dated Dec. 2, 2009.
PCT International Search Report and Written Opinion for PCT/US2013/031747, filed Mar. 14, 2013 (dated Jul. 15, 2013).
Perl, T., et al. "Determination of serum propofol concentrations by breath analysis using ion mobility spectrometry." British journal of anaesthesia 103.6 (2009): 822-827.

(56) References Cited

OTHER PUBLICATIONS

Phillips et al. "Measurement of sodium ion concentration in undiluted urine with cation-selective polymeric membrane electrodes after the removal of interfering compounds" Talanta. Nov. 30, 2007; 74(2): 255-264.

Pissinis, Diego E., and Juan M. Marioli. "Electrochemical Detection of 2, 6-Diisopropylphenol (Propofol) in Reversed Phase HPLC at High pH." Journal of liquid chromatography & related technologies 30.12 (2007): 1787-1795.

Potje-Kamloth et al. "Electrochemically prepared insulation for carbon fiber microelectrodes." Berichte der Bunsengesellschaft für physikalische Chemie 93.12 (1989): 1480-1485.

Ruzicka & Hansen, Flow Injection Analysis, John Wiley & Sons, New York (1988).

Schnider and Minto, "Pharmacokinetic models of propofol for TCI" Anaesthesia. Feb. 2008;63(2):206.

Schywalsky, Michael, et al. "Binding of propofol to human serum albumin." Arzneimittelforschung 55.06 (2005): 303-306.

Spataru et al., "Voltammetric detection of phenol at platinum-polytyramine composite electrodes in acidic media" J. Hazard. Mater. 180:777-780 (2010).

Sreevastava et al. "Automated Target Controlled Infusion Systems: The Future of Total Intravenous Anaesthesia," MJAFI 64:261-262 (2008).

Stonell et al. "Effect-site targeted patient-controlled sedation with propofol: comparison with anaesthetist administration for colonoscopy," Anaesthesia. Mar. 2006;61(3):240-7.

Struys et al. "Performance evaluation of two published closed-loop control systems using bispectral index monitoring: a simulation study" Anesthesiology. Mar. 2004;100(3):640-7.

Toth et al. "Electrochemical Detection in Liquid Flow Analytical Techniques: Characterization and Classification," Pure Appl Chem 76(6):1119-1138 (2004).

Trocewicz, J., Z. Suprynowicz, and J. Markowicz. "Determination of diprivan in urine by a supported liquid membrane technique and liquid chromatography-electrochemical detection." Journal of Chromatography B: Biomedical Sciences and Applications 685.1 (1996): 129-134.

Unger et al. "Monolithic microfabricated valves and pumps by multilayer soft lithography." Science 288.5463 (2000): 113-116.

Van Poucke et al. "Target Controlled Infusions: Targeting the Effect Site While Limiting Peak Plasma Concentration," IEEE Transactions on Biomedical Engineering 51(11):1869-1875 (2004).

Viviand et al. "Induction and Maintenance of Intravenous Anaesthesia Using Target-controlled Infusion Systems," Best Practice & Research Clinical Anaesthesiology 15(1):19-33 (2001).

Wang et al. "New Target Controlled Infusion Using a Hybrid Physiologically Based Pharmacokinetic Model," The 2nd International Conference on Bioinformatics and Biomedical Engineering, Shanghai, China, May 16-18, 2008, (978-1-4244-1748-3108) (EI, IEEE Xplore).

Willmann et al., "PK-Sim®: A Physiologically Based Pharmacokinetic 'Whole-body' Model," Biosilico I: 121-124 (2003).

Yin et al., "Electrochemical behavior of catechol, resorcinol and hydroquinone at graphene-chitosan composite film modified glassy carbon electrode and their simultaneous determination in water samples," Electrochimica Acta 56(6):2748-2753 (2011).

Yin et al., "Voltammetric sensing of paracetamol, dopamine and 4-aminophenol at a glassy carbon electrode coated with gold nanoparticles and an organophillic layered double hydroxide," Microchimica Acta Oct. 2011, 175:39-46.

Ymeti et al, "Integration of Microfluidics with a Four-channel Integrated Optical Young Interferometer Immunosensor," Biosens. Bioelectron. 20: 1417-1421 (2005).

Yun et al., "Clinical Application of Disposable Heparin Sensors—Blood Heparin Measurements During Open Heart Surgery," ASAIO J. 41:M661-M664 (1995).

Zaccheo and Bucher, "Propofol infusion syndrome: a rare complication with potentially fatal results" Crit Care Nurse. Jun. 2008;28(3):18-26.

Zejli et al., "Phenol biosensor based on Sonogel-Carbon transducer with tyrosinase alumina sol-gel immobilization," Anal Chim Acta Apr. 7, 2008;612(2):198-203.

* cited by examiner

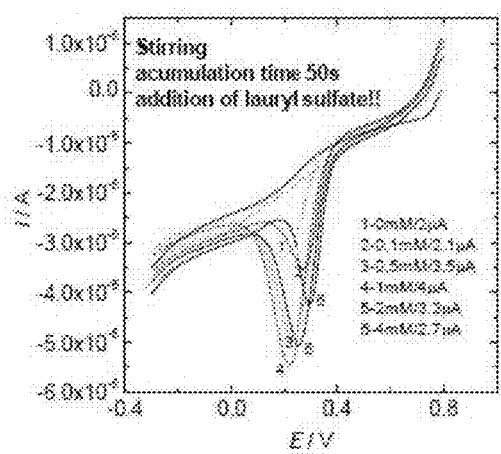 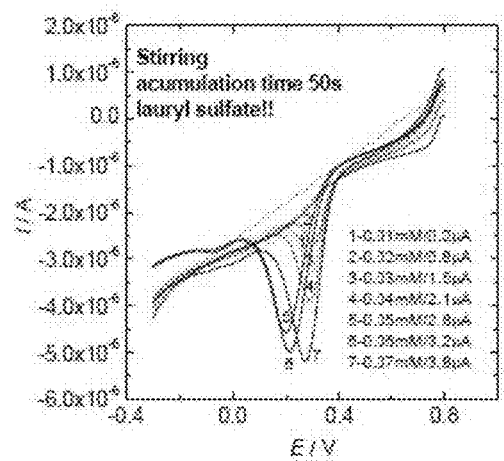
Figure 21　　　　　　　　　　Figure 22
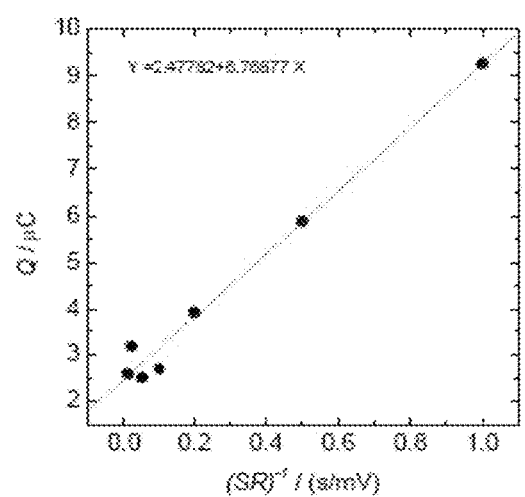
Figure 23

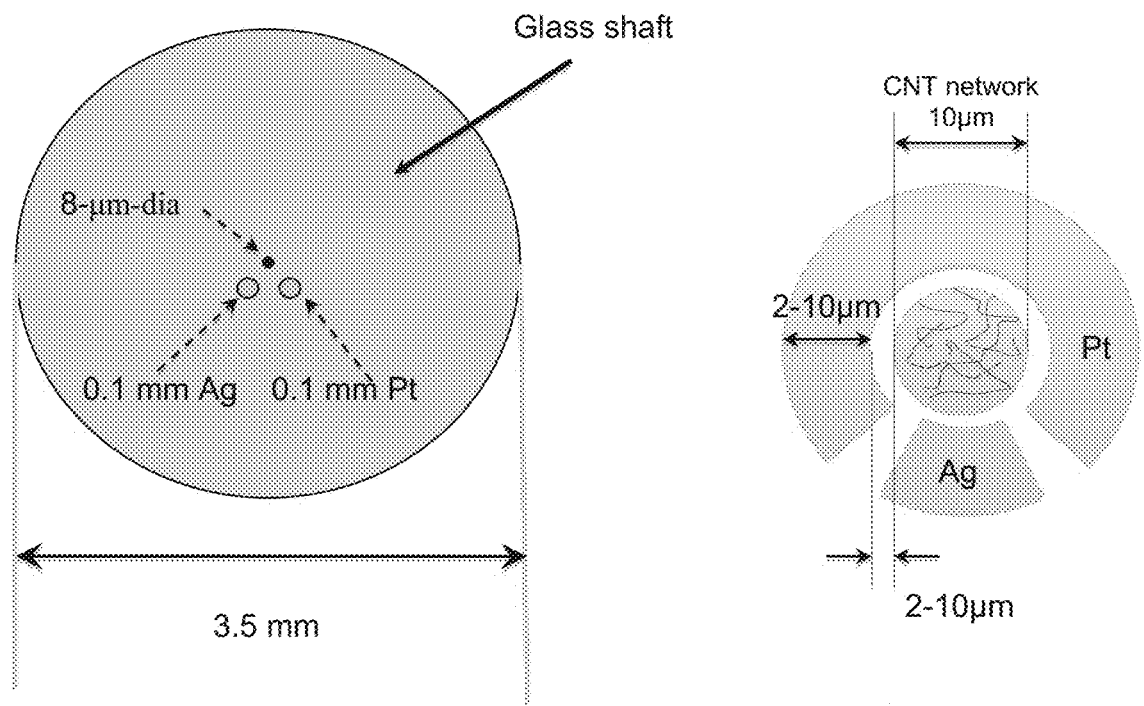
Figure 29A
Figure 29C
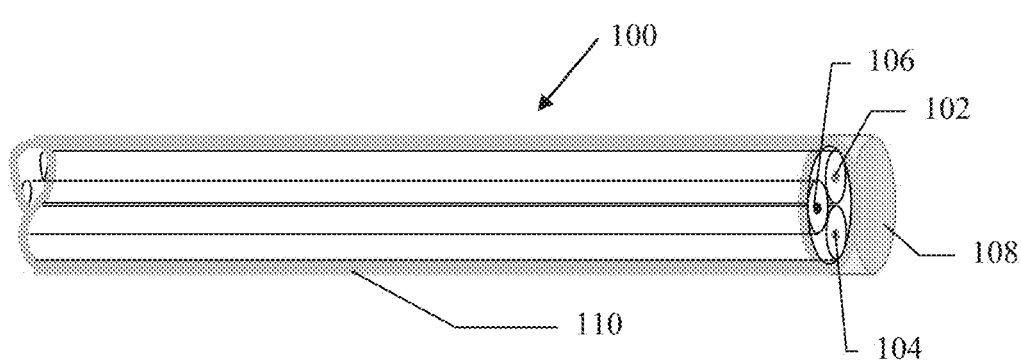
Figure 29B

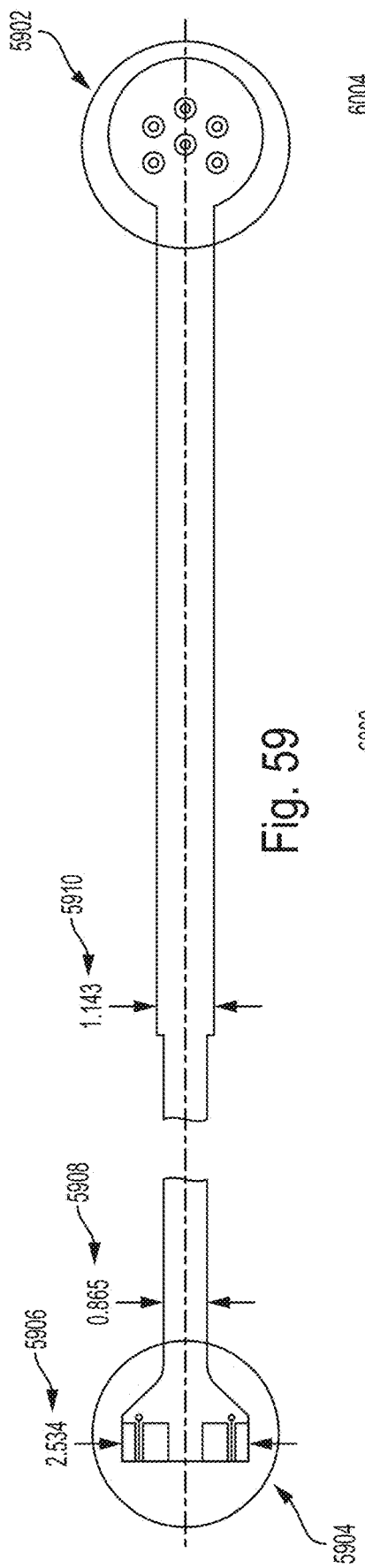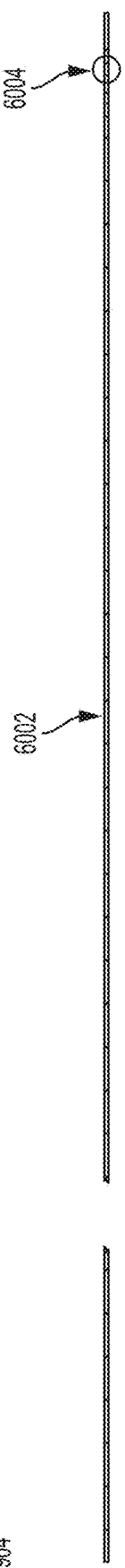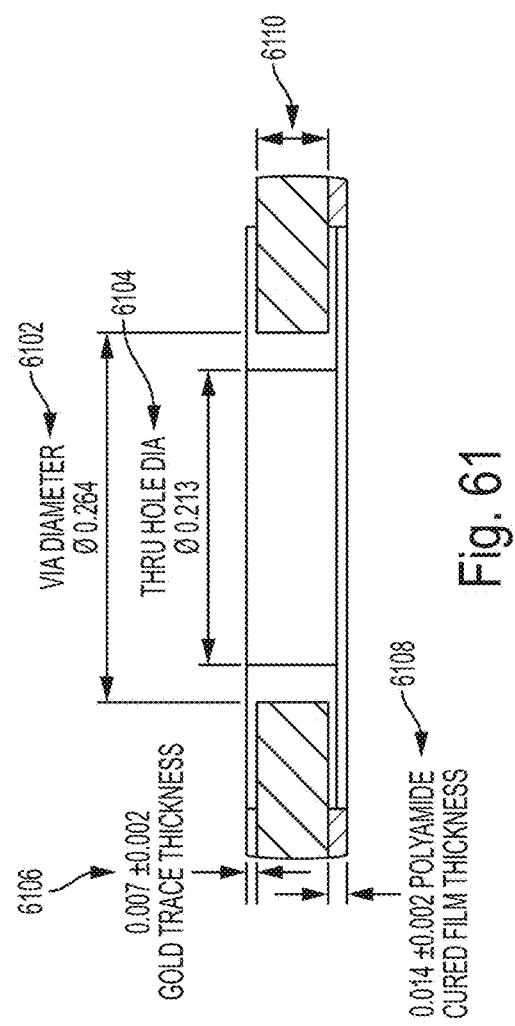
Fig. 59
Fig. 60
Fig. 61

METHOD AND DEVICE FOR DETECTION OF BIOAVAILABLE DRUG CONCENTRATION IN A FLUID SAMPLE

CROSS-REFERENCE TO RELATED APPLICATIONS

This application is a continuation in part of U.S. application Ser. No. 15/611,089, which is a continuation in part application of U.S. application Ser. No. 13/124,036, which is a 371 National Stage Entry Application of International Patent Application No. PCT/US09/60852, filed Oct. 15, 2009, which claims the benefit of U.S. Provisional Patent Application No. 61/105,604, filed Oct. 15, 2008; and is a continuation in part of U.S. application Ser. No. 14/404,674, which is a 371 National Stage Entry Application of International Patent Application No. PCT/US2013/031747, filed Mar. 14, 2013, which claims the benefit of U.S. Provisional Patent Application No. 61/654,469, filed Jun. 1, 2012. All patents and patent application publications referred to in this application are incorporated herein by reference to the same extent as if set forth herein in their entirety.

STATEMENT OF GOVERNMENT SPONSORSHIP

The present invention was made with funding received from the U.S. Army under grant W81XWH-05-2-0064 and W81XWH-10-1-0358. The government has certain rights in this invention.

FIELD OF THE INVENTION

The invention relates to a method for the controlled delivery of a drug as a function of bioavailable drug concentration, a sensor device for detecting bioavailable drug concentration, and a delivery device that controls delivery of the drug based on the real-time detection of bioavailable drug concentration.

BACKGROUND OF THE INVENTION

Computer-controlled infusion pumps, the delivery functions of which are typically determined by means of a pharmacokinetic ("PK") model, are known according to the prior art as Target Controlled Infusion ("TCI") devices and are commercially available. The main application field of TCI is the control of intravenously administered narcotics (for example Propofol, marketed as Diprifusor™ by Astra-Zeneca (Product information "Diprifusor™: Target Controlled Infusion (TCI) in anaesthetic practice", AstraZeneca Anaesthesia, New Edition (1998)). A disadvantage of these known methods is that the pharmacokinetic model is a three-compartment model fitted to experimental plasma data. With such a "black-box" method, there is no opportunity for the patient's individual drug-response to be considered.

Modifications to these TCI devices include the consideration of one or more physiological factors in combination with the PK model. The physiology-based pharmacokinetic/pharmacodynamic ("PK/PD") models such as PK-Sim® developed by Bayer Technology Services GmbH (Willmann et al., "PK-Sim®: A Physiologically Based Pharmacokinetic 'Whole-body' Model," *Biosilico* 1:121-124 (2003)), makes it possible to describe the influence of individual physiological and anatomical parameters such as organ size and composition, blood flow rates, etc., on the pharmacokinetic behavior of drugs as a function of time. These physiological and anatomical parameters can in turn be attributed to a few easily measurable quantities such as body weight and body mass index.

The exact dosage of a drug as a function of time is crucial for the safety and success of the treatment in many indication fields (e.g., anesthesia, diabetes, shock, sepsis, cardiovascular failure, asthma, and cancer). With the aid of electronically controlled infusion pumps, drugs can be administered with an arbitrarily predetermined time-variable rate. The resulting concentration-time profile and effect-time profile do not depend only on the dosage profile, however, but are essentially determined by the PK and PD properties of the drug in question. Physiology-based PK and PD computer models are only capable of simulating the concentration-time profile as well as the effect-time profile of a drug in a patient's body. They are, simply, an approximation.

Thus, there remains a need for a sensor device that can accurately detect bioavailable drug concentration, and a drug delivery device that includes such a sensor device for controlling drug delivery, in real-time, based upon detected bioavailable drug concentration.

The present invention is directed to overcoming these and other deficiencies in the art.

SUMMARY OF THE INVENTION

A first aspect of the present invention relates to an electrochemical sensor that includes two or more electrodes, and a coating that surrounds the two or more electrodes, wherein the coating comprises a structural component, a water immiscible organic solvent, and a charge transfer component, and wherein the coating selectively partitions an electrochemically active drug such that an oxidation/reduction current within the coating can be measured (via the two or more electrodes).

A second aspect of the present invention relates to an indwelling catheter that includes a body and a lumen, and one or more electrochemical sensors secured in the body with at least a portion of the sensors being in communication with either the lumen or externally of the body (such that the sensor(s) are exposed to the interior of a blood vessel). According to a preferred embodiment, the catheter contains one or more electrochemical sensors according to the first aspect of the present invention. According to another preferred embodiment, the catheter contains a sensor array that includes a plurality of working electrodes.

A third aspect of the present invention relates to a target-controlled infusion drug delivery device that includes a drug reservoir; a pump in communication with the drug reservoir; an electrochemical sensor or sensor array, the electrochemical sensor(s) comprising one or more electrodes and being capable of detecting a bioavailable drug concentration in a fluid sample; and a control system that receives output of the electrochemical sensor(s) upon detection of a bioavailable drug concentration in the fluid sample and controls operation of the pump based on the detected concentration of bioavailable drug.

A fourth aspect of the present invention relates to a method of modulating drug delivery that includes the steps of: exposing a fluid sample obtained from a patient to an electrochemical sensor comprising one or more electrodes, the electrochemical sensor capable of detecting a bioavailable drug concentration in a fluid sample; detecting an oxidation/reduction current during said exposing, wherein the detected current relates to a concentration of bioavailable drug in the fluid sample; and modulating delivery of the drug into a patient based on the concentration of the bioavailable drug in the fluid sample.

According to this aspect of the invention, the electrochemical sensor can be in the form of a sensor according to the first aspect of the present invention or a sensor array comprising a plurality of working electrodes and one or more additional electrodes, whereby the sensor or sensor array is capable of detecting a bioavailable drug concentration in a fluid sample from the patient. The sensor or sensor array can be positioned ex vivo or in vivo.

A fifth aspect of the present invention relates to a method for electrochemical detection of bioavailable drug concentration in a fluid sample, the method including the steps of exposing a fluid sample to an electrochemical sensor comprising one or more electrodes and a coating that surrounds the one or more electrodes, which coating is capable of partitioning the bioavailable drug directly from the fluid sample; and detecting an oxidation/reduction current during said exposing, wherein the detected current relates to the concentration of bioavailable drug in the fluid sample.

A sixth aspect of the present invention relates to a method for electrochemical detection of bioavailable drug concentration in a fluid sample, the method including the steps of exposing a fluid sample to an electrochemical sensor array comprising a plurality of working electrodes and one or more additional electrodes; and detecting an oxidation/reduction current during said exposing, wherein the detected current relates to the concentration of bioavailable drug in the fluid sample. By virtue of the array comprising the plurality of working electrodes, the detecting is intended to be carried out repeatedly with a different working electrode during each step.

A seventh aspect of the present invention relates to an electrochemical sensor including an electrode and a coating that surrounds the electrode, the coating comprising a structural component, a water immiscible solvent, a resistance decreasing component, and an ion exchange component, wherein the coating selectively partitions an electrochemically active drug from a fluid or vapor sample whereby an electrochemical signal within the coating can be measured using the electrode.

An eighth aspect of the present invention relates to a target-controlled infusion drug delivery device that includes a drug reservoir, a pump in communication with the drug reservoir, an electrochemical sensor according to an aspect of the present invention described herein, and a control system that receives an output of the electrochemical sensor upon detection of the bioavailable drug concentration in a fluid or vapor sample and controls operation of the pump based on the detected concentration of bioavailable drug.

A ninth aspect of the present invention relates to a microfluidic device that includes a microfluid channel and an electrochemical sensor according to the an aspect of the present invention in communication with the microfluid channel.

A tenth aspect of the present invention relates to a method of modulating drug delivery that includes exposing a fluid or vapor sample obtained from a patient to an electrochemical sensor according to an aspect of the present invention; detecting an electrochemical signal within the coating during said exposing, wherein the detected electrochemical signal relates to a concentration of bioavailable drug in the fluid or vapor sample; and modulating delivery of the drug into a patient based on the concentration of the bioavailable drug in the fluid or vapor sample.

An eleventh aspect of the present invention relates to a method for electrochemical detection of bioavailable drug concentration in a fluid or vapor sample, which method includes exposing a fluid or vapor sample to an electrochemical sensor according to an aspect of the present invention; and detecting an electrochemical signal within the coating during said exposing, wherein the detected electrochemical signal relates to the concentration of bioavailable drug in the fluid or vapor sample.

The accompanying experimental data demonstrate the preparation and testing of electrochemical sensors that permit electrochemical monitoring of hydrophobic drugs, such as propofol, in aqueous electrolyte solutions, blood, serum, or plasma. This will allow for the construction of a closed-loop, feedback controlled infusion of propofol during anesthesia. To obtain a mechanically robust working electrode, the organic film was immobilized to the electrode surface in the form of a highly plasticized PVC membrane (Horvath et al., Anal. Chim. Acta 273:145-152 (1993); Amemiya et al., Anal. Bioanal. Chem. 399:571-579 (2011); Guo et al., Anal. Chem. 78:6893-6902 (2006), each of which is hereby incorporated by reference in its entirety). Coating the surface of a working electrode, advantageously made of glassy carbon or gold, with a highly plasticized PVC membrane prevented electrode fouling and allowed for chronoamperometric detection of sub-micromolar levels of propofol in serum-like electrolytes containing 5% bovine serum albumin (BSA), 3 mM ascorbic acid (AA), and 1 mM p-acetamido phenol (APAP), as well as in serum like electrolytes containing 5% human serum albumin (HSA), 3 mM ascorbic acid (AA), and 1 mM p-acetamido phenol (APAP), and patient serum samples.

These methods of electrochemical detection of bioavailable drug concentration are intended to be used to modify the delivery rate of the drug to a patient during real-time.

The accompanying Examples demonstrate that the drug Propofol ("DIPP") can be detected in acidic solutions in vitro and can be quantified down to a concentration as low as $1 \times 10^{-6}$M, which is within the therapeutic dose range of the drug for its use as a general anesthetic agent. It has also been determined that the accuracy of DIPP signal detection and signal intensity is influenced by several features of the electrochemical method, including pH and composition of the solution, voltage scan rate, presence and optimal concentration of detergents, agitation of the solution during quantitation, and the deposition of biofilms/electrode fouling. The Examples further demonstrate that an accurate quantification of DIPP can be obtained within 30 seconds using this method and that a robust signal is seen at therapeutic and sub-therapeutic levels using cyclic voltammetry. The ability to measure therapeutic levels using microfabricated thin film microelectrodes and nanoelectrode arrays demonstrate different approaches for overcoming the problem of biofouling. In particular, the coated electrodes are capable of partitioning free (bioactive) DIPP into the organic sensor membrane from complex solutions, removing chloride ion interference from the detection of DIPP in salt-containing solutions, and are free from interference with other molecules such as acetaminophen (Tylenol®) and Vitamin C. Sensor arrays overcome the problem using a plurality of working electrodes, such that for each sensing event a new working electrode is employed. These results will allow for construction of an indwelling sensor or ex vivo microfluidic sensor for use in closed-loop control systems that integrate into TCIA biosensor for delivery of DIPP.

Embodiments comprise an electrochemical voltammetric sensor device comprising, a body comprising a first lumen; a securing body comprising a second lumen; a flexible circuit comprising a connection end and a sensor end, wherein the flexible circuit comprises a flexible strip of material; the connection end comprising a plurality of vias; the sensor end comprising an electrochemical sensor, wherein the electrochemical sensor comprises a first array of electrodes, wherein the first array of electrodes are electrically connected to the vias using conductive traces, wherein the first array of electrodes comprises a water-immiscible coating that surrounds the first array of electrodes, wherein the coating partitions a hydrophobic drug from a fluid sample; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising a first opening positioned above the first array of electrodes, wherein the first opening exposes the first array of electrodes to the fluid sample.

Embodiments further comprise an electrochemical voltammetric sensor device, wherein the flexible strip of material comprises a first layer and a second layer, wherein the first layer and the second layer comprise polyamide.

Still further embodiments comprise an electrochemical voltammetric sensor device, wherein the flexible strip of material comprises a third layer between the first and the second layer, wherein the third layer comprises adhesive and the conductive traces.

Further, embodiments comprise an electrochemical voltammetric sensor device, wherein pins of a mating connector pass through corresponding vias of the connection end, wherein the pins and the connection end are joined by soldering the pins to the corresponding vias.

Embodiments also comprise an electrochemical voltammetric sensor device, wherein the mating connector couples the vias to a potentiostat circuit which controls voltage and current supplied to the electrochemical sensor.

Embodiments further comprise an electrochemical voltammetric sensor device, wherein the electrochemical sensor comprises a second array of electrodes, wherein the second array of electrodes are electrically connected to the vias using conductive traces, wherein the second array of electrodes comprises the water-immiscible coating that surrounds the second array of electrodes, wherein the coating partitions the hydrophobic drug from the fluid sample.

Still further, embodiments comprise an electrochemical voltammetric sensor device, wherein the securing body comprising a second opening positioned above the second array of electrodes, wherein the second opening exposes the second array of electrodes to the fluid sample.

Embodiments also comprise an electrochemical, voltammetric sensor device, wherein the hydrophobic drug is oxidized within the coating, wherein at least one of the first array of electrodes and the second array of electrodes measure an oxidation/reduction current within the coating, and wherein the measured oxidation/reduction current correlates to the amount of the hydrophobic drug partitioned into the coating.

In embodiments, the coating further comprises a membrane resistance controlling component selected from the group consisting of lipophilic electrolytes, tetradodecyl ammonium-tetrakis(4-chlorophenyl) borate (ETH500), and bis(triphenylphoranylidene) ammonium tetrakis[3,5-bis(trifluoromethyl)phenyl] borate (BTPPATFPB); a biocompatibility enhancing component selected from the group consisting of nitric-oxide releasing sol-gel materials, N-(6-aminohexyl)aminopropyltrimethoxysilane, and balanced isobutyltrimethoxysilane diazeniumdiolate; or both.

In embodiments the coating comprises PVC, o-NPOE, and TDATPFPB.

In further embodiments, the coating is less than about 200 μm thick.

Embodiments further comprise a drug delivery device. For example, the drug delivery system comprises a body comprising a first lumen; a securing body comprising a second lumen; a flexible circuit comprising a connection end and a sensor end, wherein the flexible circuit comprises a flexible strip of material; the sensor end comprising an electrochemical sensor, wherein the electrochemical sensor comprises an array of electrodes; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising at least one opening positioned above the array of electrodes, wherein the at least one opening exposes the array of electrodes to a fluid sample; a control system that receives an output of the electrochemical sensor upon detection of a bioavailable drug concentration in the fluid sample and controls delivery of a bioavailable drug into a patient based on the bioavailable drug concentration.

In embodiments, the bioavailable drug is selected from the group of anesthetics, barbiturates, and sedatives.

In further embodiments, the bioavailable drug is selected from the group consisting of Propofol, midazolam, methohexital, etomidate, and sufentanil.

Further, in embodiments, the control system measures the output of the electrochemical sensor and controls drug delivery in real-time based on the measured output.

Embodiments are also directed towards a method of modulating drug delivery. For example, the method comprises placing a sensor device into a blood vessel of a patient, the sensor device including a body, a securing body, and a flexible circuit, wherein the body comprises a first lumen, wherein the securing body comprises a second lumen, wherein the flexible circuit comprises an electrochemical sensor, wherein the electrochemical sensor comprises an array of electrodes, wherein the array of electrodes comprises a water-immiscible coating surrounding the array of electrodes, wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body, wherein the securing body comprises at least one opening positioned above the array of electrodes; the placing the sensor device into the blood vessel including the at least one opening exposing a fluid sample containing a bioavailable hydrophobic drug to the array of electrodes, wherein the coating of the array of electrodes partitions the bioavailable hydrophobic drug from the fluid sample; detecting an oxidation/reduction current within the coating during said exposing, wherein the detected current relates to a concentration of the bioavailable hydrophobic drug in the fluid sample; and modulating delivery of a hydrophobic drug into the patient based on the concentration of the bioavailable hydrophobic drug in the fluid sample.

In embodiments, the step of detecting is repeated.

In embodiments, the repetition of said detecting is carried out at a frequency of at least every 5 minutes.

In embodiments, modulating is carried out if the bioavailable drug concentration in the fluid sample is less than a first threshold value or greater than a second threshold value.

In further embodiments, modulating is carried out in real-time based on said detecting.

Embodiments are further directed towards a method comprising, exposing a fluid sample to an electrochemical, voltammetric sensor device, wherein the electrochemical, voltammetric sensor device comprises, a body comprising a lumen; a securing body comprising a second lumen; a flexible circuit comprising a connection end and a sensor end, wherein the flexible circuit comprise a flexible strip of material; the connection end comprising a plurality of vias; the sensor end comprising an electrochemical sensor, wherein the electrochemical sensor comprises an array of electrodes, wherein the array of electrodes are electrically connected to the vias using conductive traces, wherein the array of electrodes comprises a water-immiscible coating that surrounds the array of electrodes, wherein the coating partitions a hydrophobic drug from the fluid sample; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising at least one opening positioned above the array of electrodes; the exposing the fluid sample to the electrochemical, voltammetric sensor device including the at least one opening exposing the array of electrodes to the fluid sample; detecting an oxidation/reduction current within the coating during said exposing, wherein the detected current depends on a concentration of the hydrophobic drug in the coating as a consequence of the partitioning of the hydrophobic drug from the fluid sample, wherein the detected current correlates to the concentration of the hydrophobic drug in the fluid sample.

In embodiments, the hydrophobic drug is Propofol, the fluid sample is blood or serum, and a concentration of bioavailable Propofol is detected.

Other embodiments are directed towards an electrochemical, voltammetric sensor device comprising a body comprising a first lumen; a securing body comprising a second lumen; a flexible circuit comprising a connection end and a sensor end, wherein the flexible circuit comprises a flexible strip of material; the sensor end comprising an electrochemical sensor, wherein the electrochemical sensor comprises two or more electrodes and a coating that surrounds the two or more electrodes, wherein the coating comprises a structural component, a water immiscible organic solvent, a charge transfer component, and an electrochemically active, hydrophobic drug, wherein the sensor device measures an oxidation/reduction current within the coating using the two or more electrodes, wherein the measured oxidation/reduction current correlates to the amount of the electrochemically active, hydrophobic drug partitioned into the coating from a fluid sample during use of the sensor device; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising at least one opening positioned above the two or more electrodes, wherein at least one opening exposes the two or more electrodes to the fluid sample.

In embodiments, the structural component comprises a polymer selected from the group consisting of polyvinylchloride (PVC), silicone rubber, polyurethane, (meth)acrylate polymer, polypyrrole, polythiophene, polyanaline, polyvinyl pyrrolidone, agarose, hydrogel, sol-gel materials, and combinations thereof.

Embodiments further comprise an electrochemical, voltammetric sensor device, wherein the water immiscible organic solvent comprises 2-nitrophenyl octyl ether (o-NPOE), dioctyl sebacate (DOS), bis(2-ethylhexyl) sebacate, benzyl s-nitrophenyl ether, bis(1-butilpentyl) adipate, bis(2-ethylhexyl) adipate, bis(2-ethylhexyl) phthalate, 1-chloronaphthalene, chloroparaffin, I-decanol, dibutyl phthalate, dibutyl sebacate, dibutyldilaurate, dodecyl 2-nitrophenyl ether, or combinations thereof.

In embodiments, the charge transfer component is tetradecylammonium tetrakis(pentofluorophenyl)borate (TDATPFPB), tetrahexylammonium perchlorate, or a combination thereof.

Embodiments are also directed towards an electrochemical, voltammetric sensor device comprising a body comprising a first lumen; a securing body comprising a second lumen; a flexible circuit comprising a connection end and a sensor end, wherein the flexible circuit comprises a flexible strip of material; the sensor end comprising an electrochemical sensor, wherein the electrochemical sensor comprises at least two electrodes and a water-immiscible coating that surrounds the at least two electrodes, wherein the coating is in contact with the at least two electrodes, wherein the coating comprises about 15 to about 67 wt percent PVC, about 33 to about 85 wt percent 0-NPOE, and about 0.001 to about 15 wt percent TDATPFPB, wherein the coating partitions a hydrophobic drug from a fluid sample, wherein the partitioned drug is oxidized within the coating, wherein the at least two electrodes measure an oxidation/reduction current within the coating, and wherein the measured oxidation/reduction current indicates the concentration of the hydrophobic drug in the fluid sample; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising at least one opening positioned above the at least two electrodes, wherein the at least one opening exposes the at least two electrodes to the fluid sample.

In embodiments, the at least two electrodes comprise a working electrode, a reference electrode, a counter electrode, or any combination thereof.

In embodiments, the working electrode comprises glassy carbon, the reference electrode comprises silver, and the counter electrode comprises platinum.

In embodiments, the coating comprises a structural component, a water immiscible organic solvent, and a charge transfer component.

Embodiments further comprise an electrochemical, voltammetric sensor device comprising a body comprising a first lumen; a securing body comprising a second lumen; a flexible circuit comprising a connection end and a sensor end, wherein the flexible circuit comprise a flexible strip of material; the sensor end comprising an electrochemical sensor, wherein the electrochemical sensor comprises electrodes and a water-immiscible coating that surrounds the electrodes, wherein the coating comprises about 15 to about 67 wt percent PVC, about 33 to about 85 wt percent o-NPOE, and about 0.001 to about 15 wt percent TDATPFPB, wherein the coating partitions a hydrophobic drug from a fluid sample; wherein the body resides within the second lumen of the securing body, wherein an upper surface of the flexible circuit is adjacent and conforms to an interior circumferential curvature of the second lumen, wherein a lower surface of the flexible circuit is adjacent and conforms to an exterior circumferential curvature of the body; the securing body comprising at least one opening positioned above the electrodes, wherein at least one opening exposes the electrodes to the fluid sample.

In embodiments, the electrodes comprise a glassy carbon working electrode, a silver reference electrode, a platinum counter electrode, or any combination thereof.

BRIEF DESCRIPTION OF THE DRAWINGS

FIG. 21 is a stripping voltammogram of $4 \times 10^{-5}$M DIPP in $10^{-2}$M $H_2SO_4$+0.1, 0.5, 1.2, $2.4 \times 10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 22 is a stripping voltammogram of $1\text{-}7 \times 10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water.

Working electrode=glassy carbon; counter electrode=Pt; and reference electrode=Ag/AgCl.

FIG. 23 is a graph showing the relationship between the charge under the DIPP stripping peak and the voltage scan rate for stripping under the conditions of $4\times10^{-5}$M DIPP in $10^{-2}$M $H_2SO_4 + 10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

Figure 24:
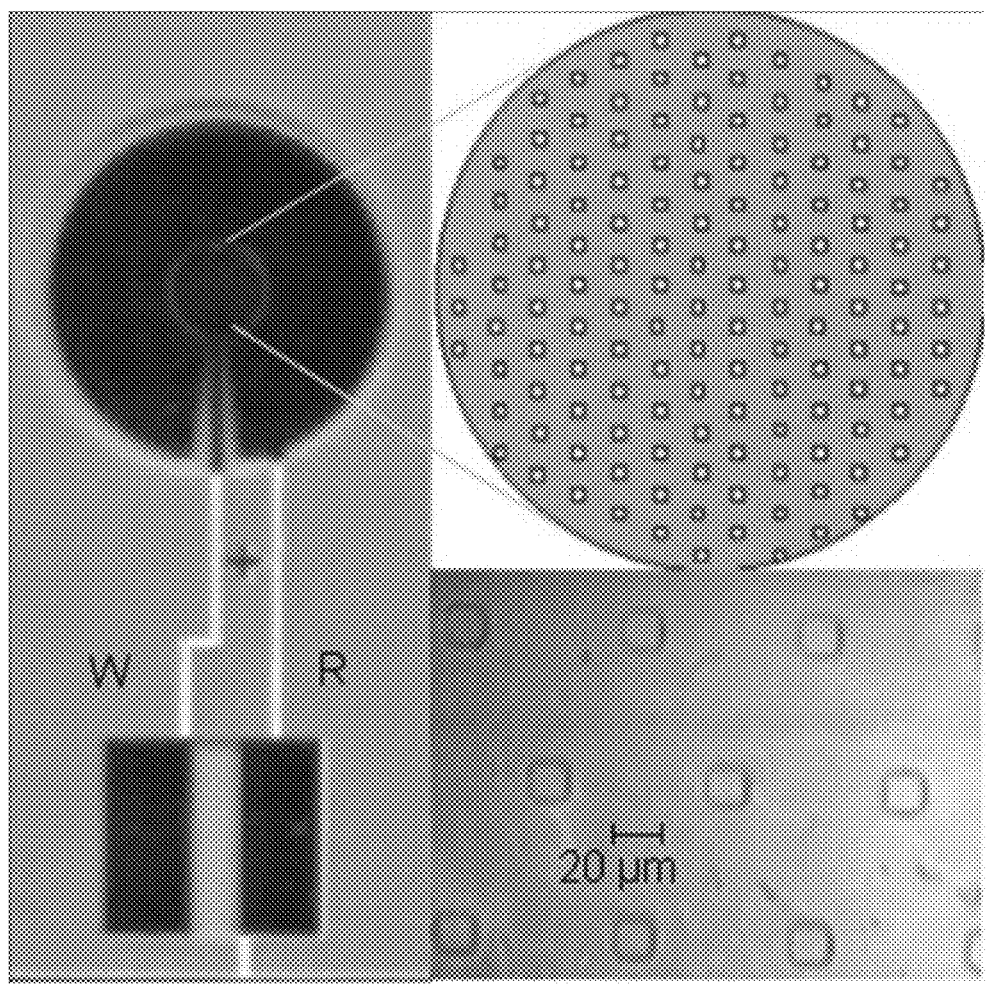

FIG. 24 is a microscopic image a fabricated carbon microelectrode containing a grid array of electrochemical sensors.

Figure 25:
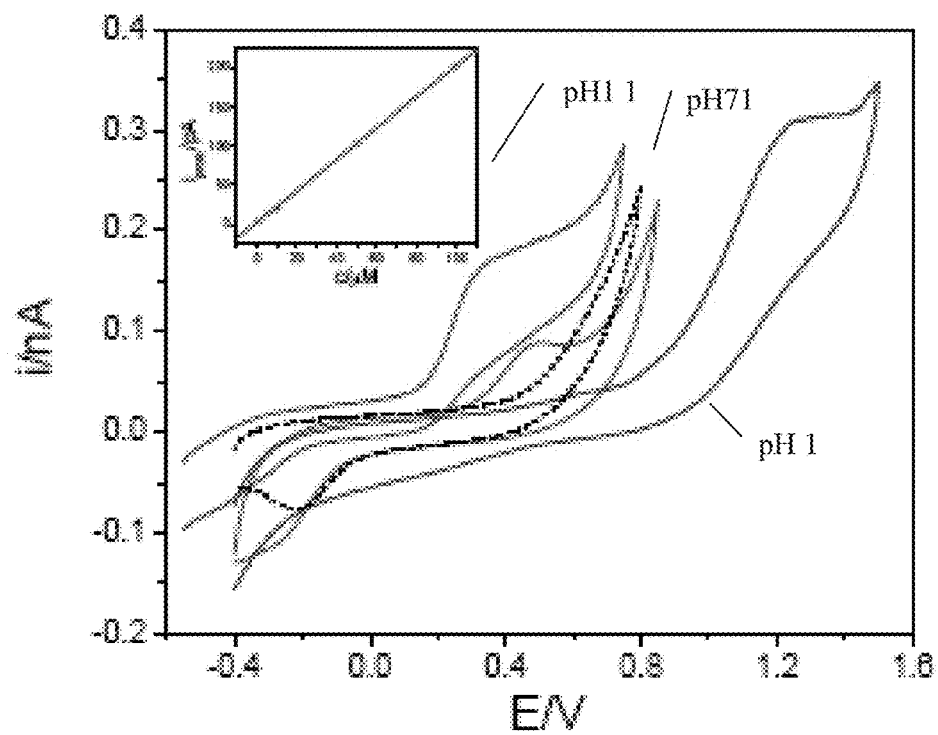

FIG. 25 is an overlay of cyclic voltammograms of the Propofol signal using carbon microelectrodes at varying pH values. Blue curve, pH1; neutral pH7 (dashed line 1st cycle, red line 2nd cycle), and green curve, pH11. Calibration curve (inset) is measured at pH7 and demonstrates a linear, dose-dependent response.

Figure 26A:
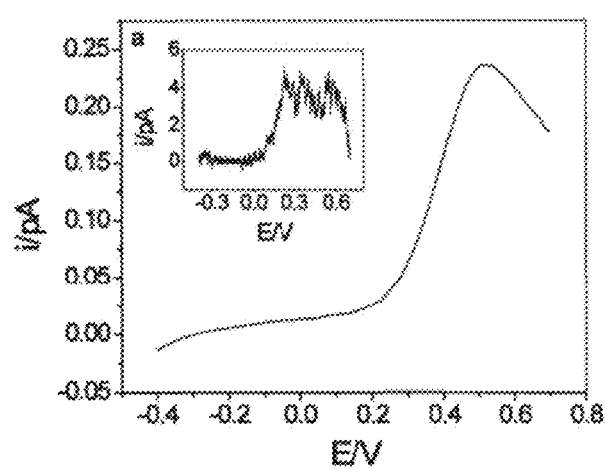
Figure 26B:
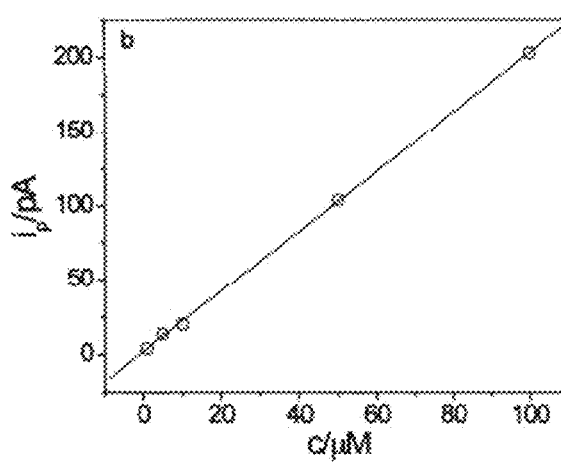

FIGS. 26A-B are a pair of graphs that illustrate the stripping analysis of Propofol in 0.01M pH7.0 HEPES solution: (a) the background-corrected stripping voltammograms for 0.1 mM and 1 μM Propofol (inset), and (b) the calibration curve of Propofol from 1.0 μM to 0.1 mM.

Figure 27:
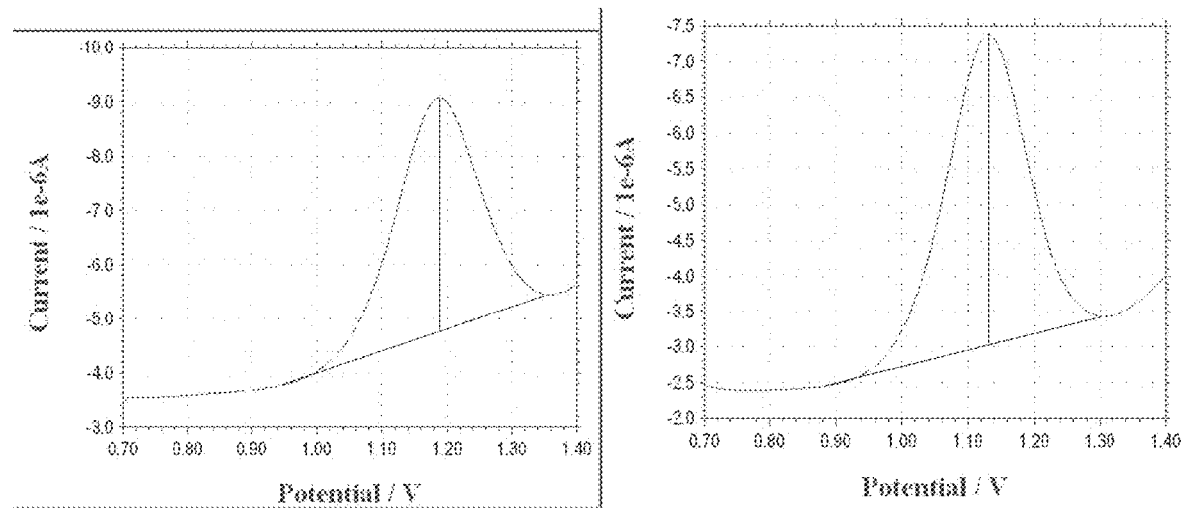

FIG. 27 is a pair of graphs illustrating signal intensity variances between different fibers in a CNF array.

Figure 28:
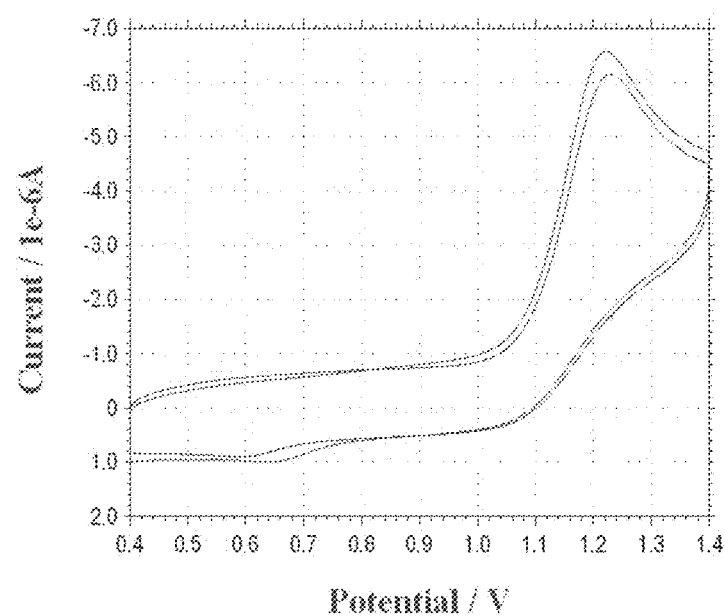

FIG. 28 is a cyclic voltammogram on a GC electrode in organic solution. No significant fouling is seen.

FIGS. 29A-C illustrate fabricated microelectrode designs, specifically the capillary array with sensors embedded in a coating (29A-B) and lithography design (29C).

Figure 30:
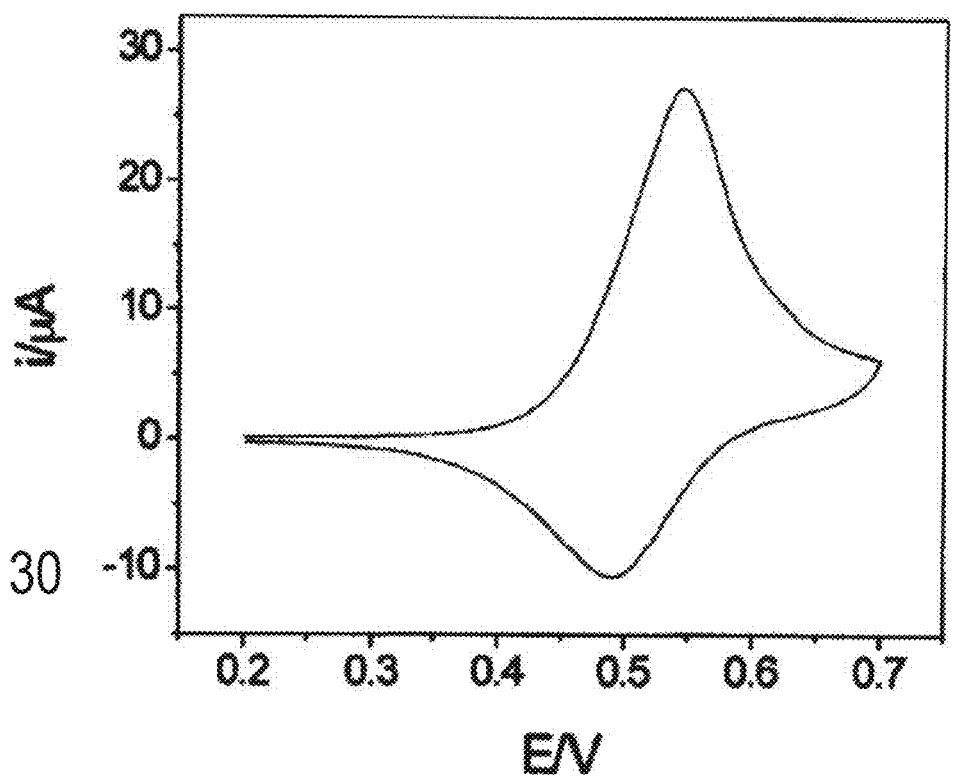

FIG. 30 is a cyclic voltammetry recorded with PVC-o-NPOE GC electrode in 0.5 mM FcMeOH and 8 mM TBAClO$_4$ solution.

Figure 31:
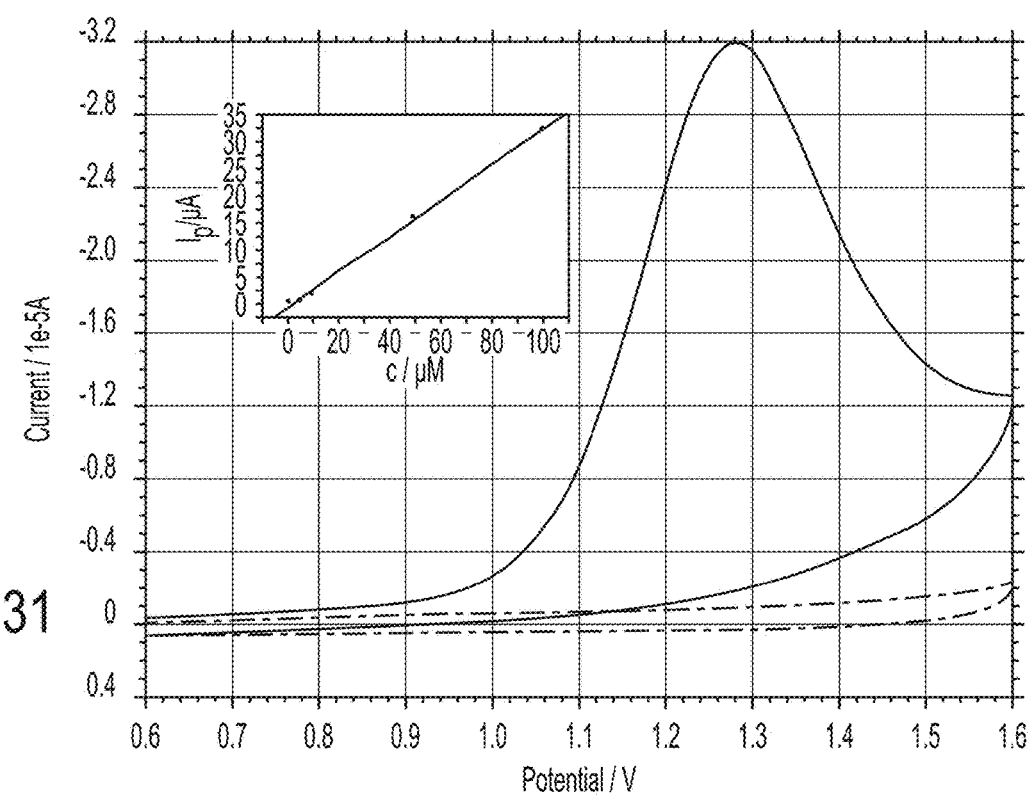

FIG. 31 is a cyclic voltammetry recorded with PVC-o-NPOE membrane-coated GC electrode in x mM Propofol+8 mM TBAClO4 pH 7.2 PBS solution (red line). The inset graph shows the calibration curve of DIPP from 1 μM to 0.1 mM in the same background solution.

Figure 32:
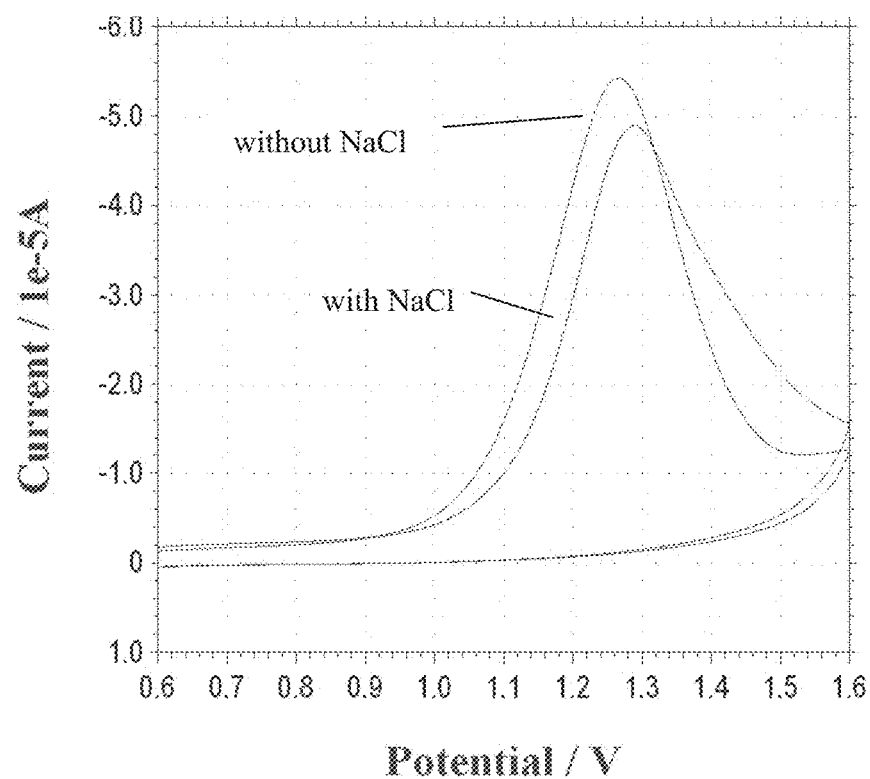

FIG. 32 is a cyclic voltammetry of 0.1M DIPP recorded with (red line) and without (blue line) 0.12M NaCl, with 8 mM TBAClO$_4$ and 0.1M PBS (pH 7.2).

Figure 33:
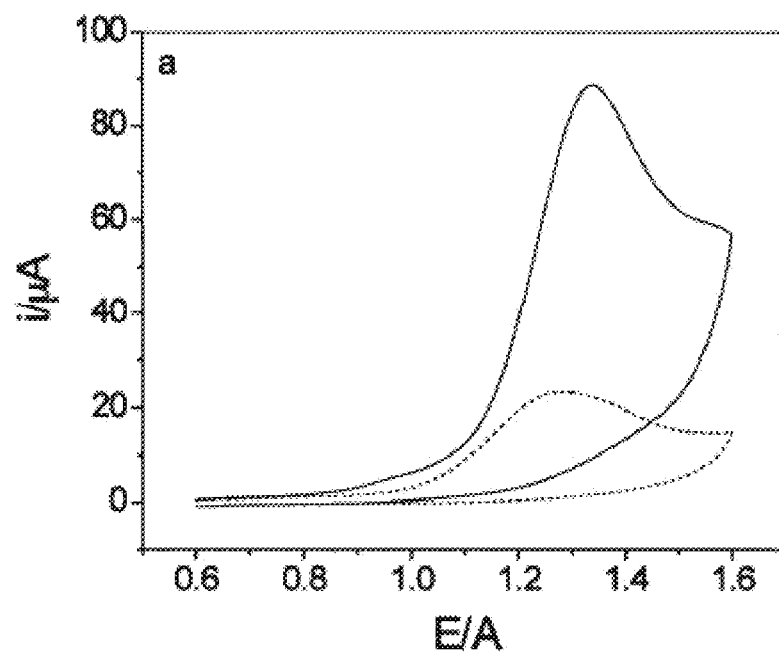

FIG. 33 is a cyclic voltammetry of 0.1M DIPP recorded with (dashed line) and without (solid line) 4% BSA.

Figure 34:
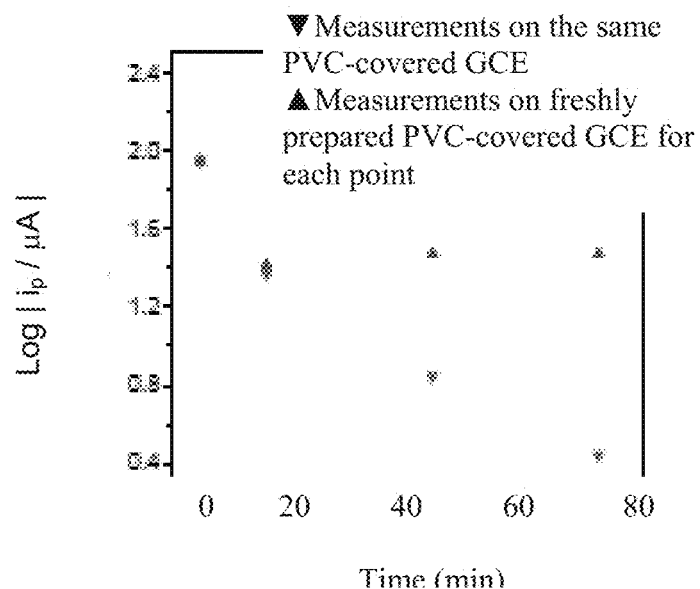

FIG. 34 is a graph showing the change in peak current over time in DIPP solution with 4% BSA. Maintained (red) or fresh GC electrode (blue) data are shown for comparison.

Figure 35:
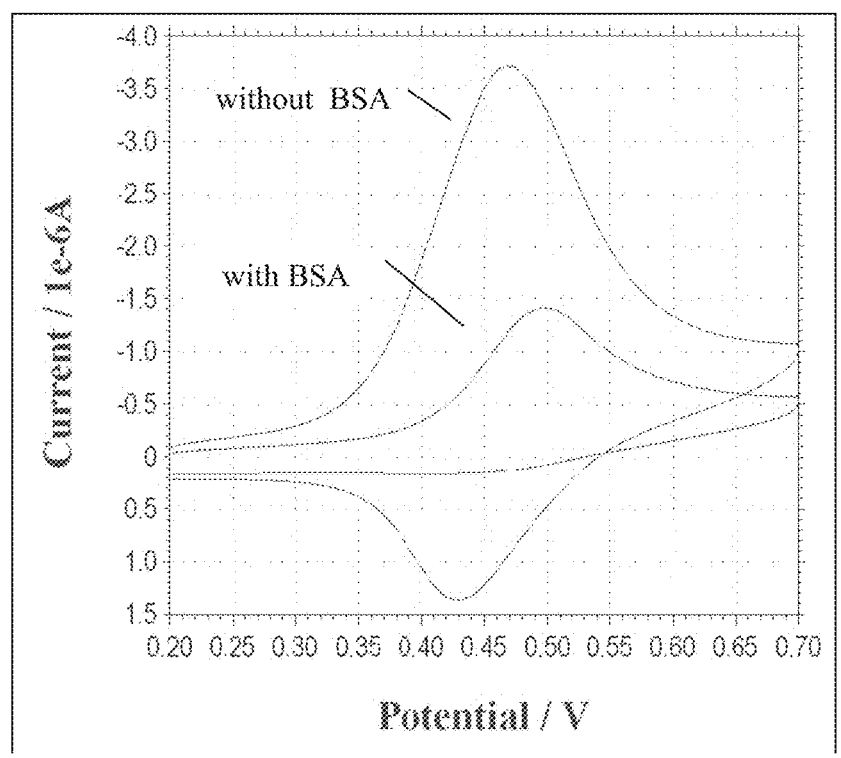

FIG. 35 is a cyclic voltammetry of 0.1M ferrocene methanol in the absence (blue line) or in the presence of 4% BSA (red line).

Figure 36:
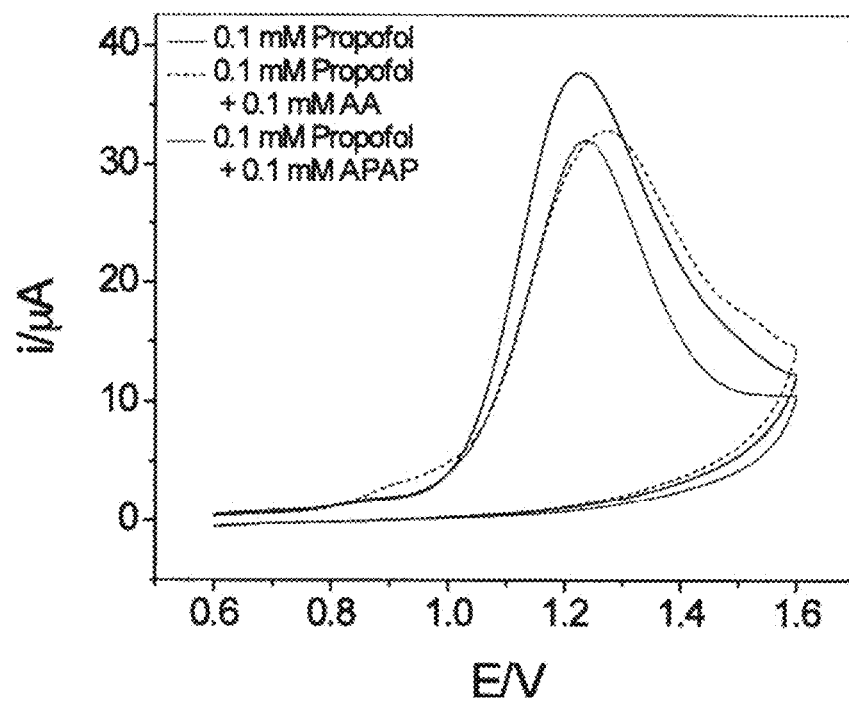

FIG. 36 is a cyclic voltammetry of 0.1 mM DIPP in the absence of interference (solid line), or in the presence of 0.1 mM ascorbate (dashed line) or 0.1 mM N-acetyl-p-aminophenol (dotted line).

Figure 37:
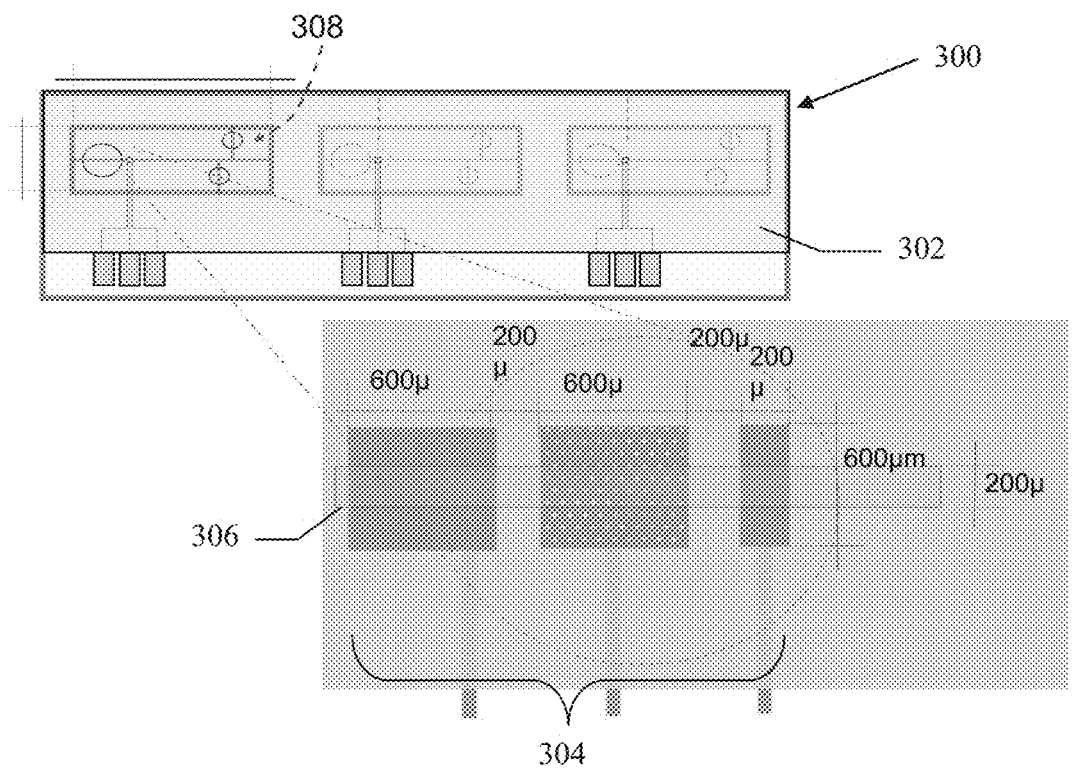

FIG. 37 is a plan view of a microfluidic DIPP biosensor with polyimide insulation and three microelectrochemical grid array sensors in series in a microfluidic channel. The electrochemical sensors are formed using 5 micron diameter gold discs positioned 50 μm center-to-center in a hexagonal arrangement.

Figure 38:
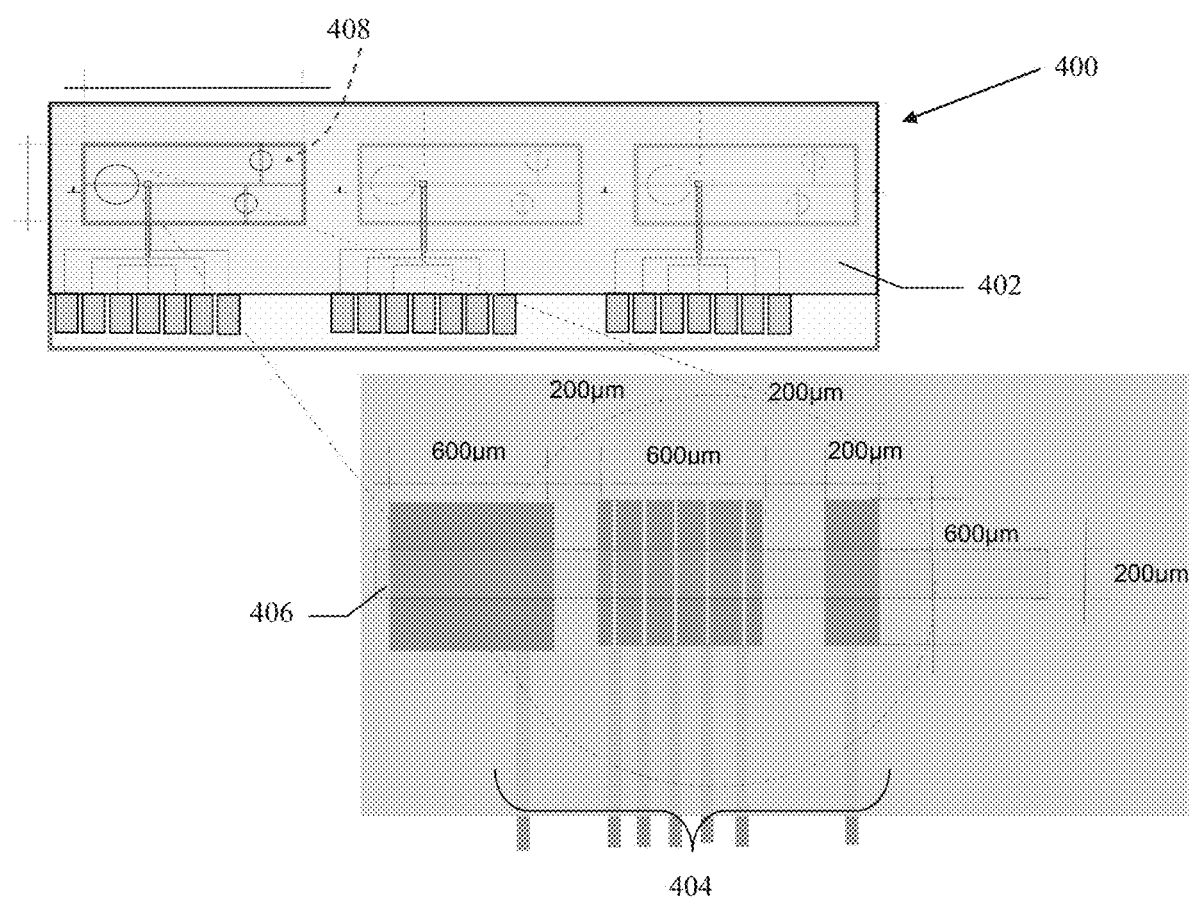

FIG. 38 is a plan view of a microfluidic DIPP biosensor with polyimide insulation and a microband sensor array in a microfluidic channel. 5 μm wide individually addressable bands are spaced 100 μm center-to-center. The sensors can optionally be interconnected with a single lead wire.

Figure 39:
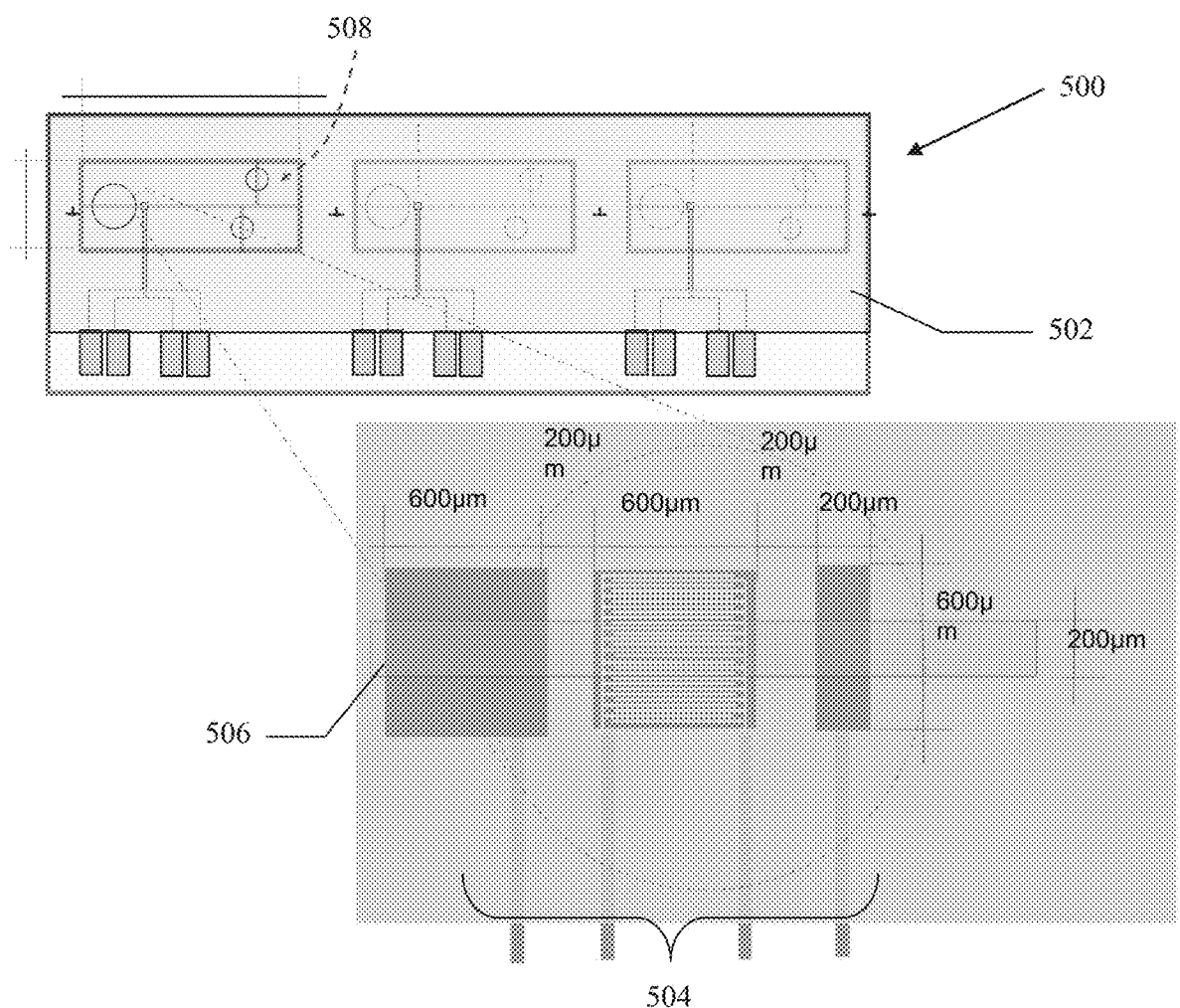

FIG. 39 is a plan view of a microfluidic DIPP biosensor with polyimide insulation and three interdigitated array electrochemical sensors in series in a microfluidic channel. The interdigitated electrode array includes with 5 μm wide fingers and 5 μm wide gaps between the fingers.

Figure 40:
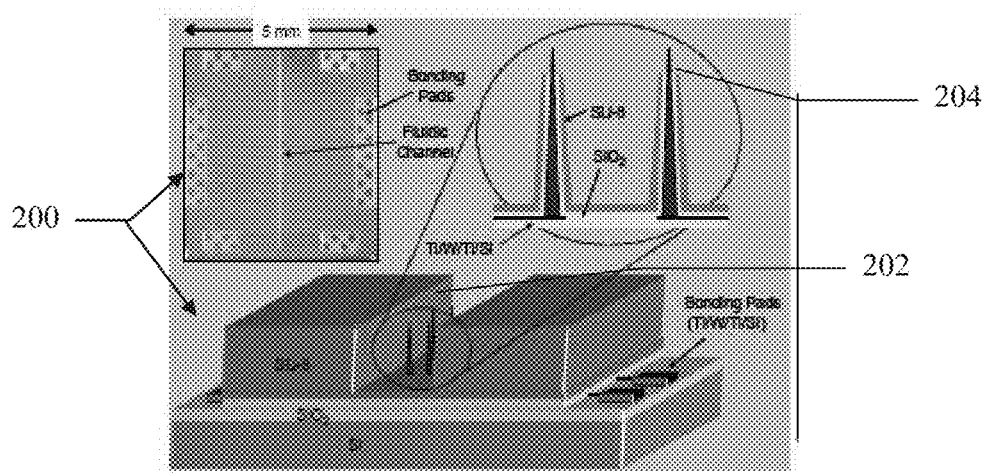

FIG. 40 is a schematic of a microfluidic device into which a plurality of carbon nanofibers are integrated into an array within a microfluidic channel of the device. This allows for the construction of multiscale devices capable of serial measurements. Individual nanofibers are electrically addressed using interconnect structures on the nanofiber substrate. Each nanofiber is passivated with an oxide layer, so that only the extreme tip is electrochemically active. Single fibers and nanofiber forest electrodes are configured. This exemplary figure was obtained from Dr. Timothy McKnight of Oak Ridge National Laboratory.

Figure 41:
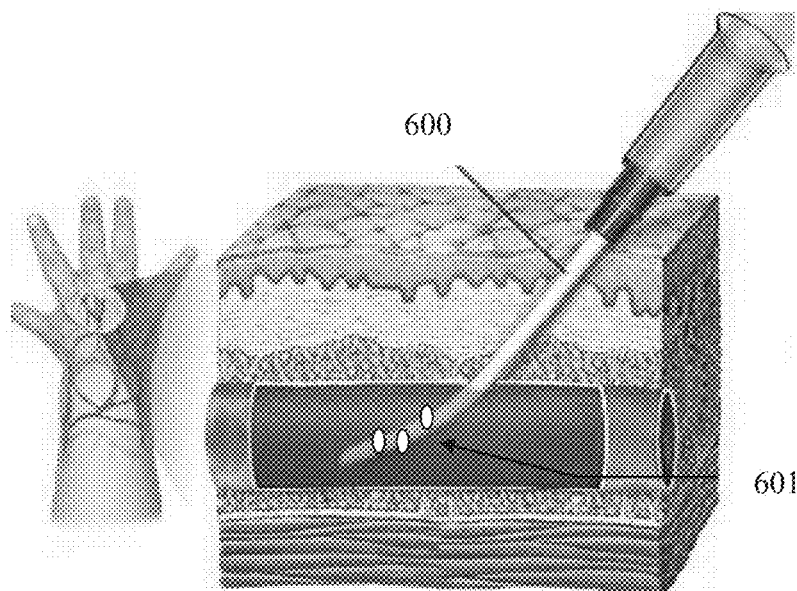

FIG. 41 is an illustration of a catheter of the invention that includes an electrochemical sensor of the present invention introduced into the body thereof, such that upon insertion of the catheter into a patient blood vessel, the electrochemical sensor is in fluid contact with the patient's blood for detection of bioavailable drug concentration.

Figure 42:
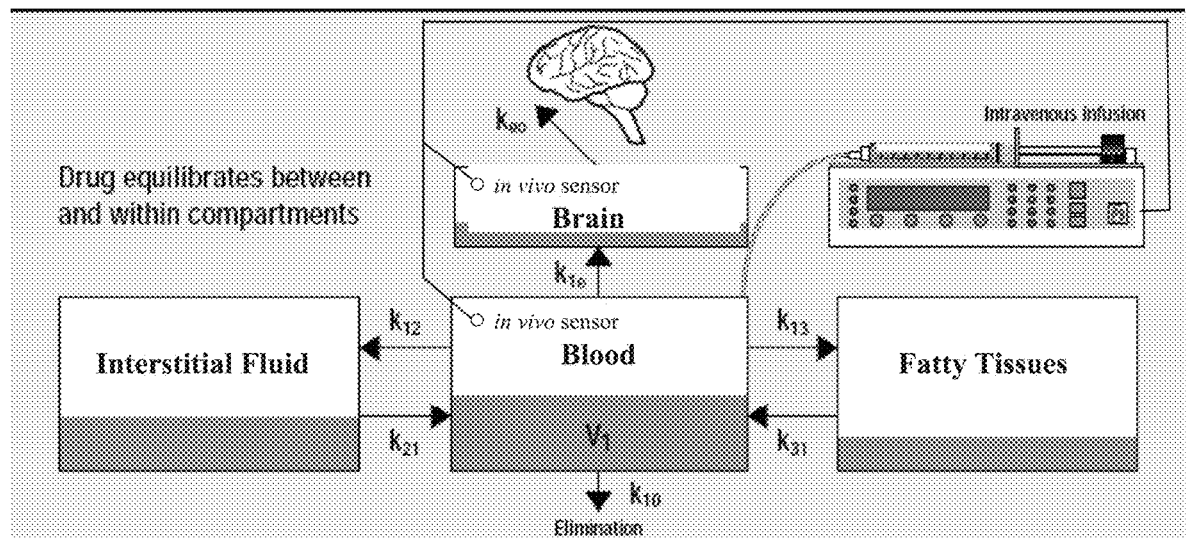

FIG. 42 is a schematic diagram illustrating the feedback mechanism for direct, real time feedback control by electrochemical biosensors regarding the bioavailable drug concentration. The measured bioavailable drug concentration is then used to direct drug delivery through a feedback loop to a pump.

Figure 43:
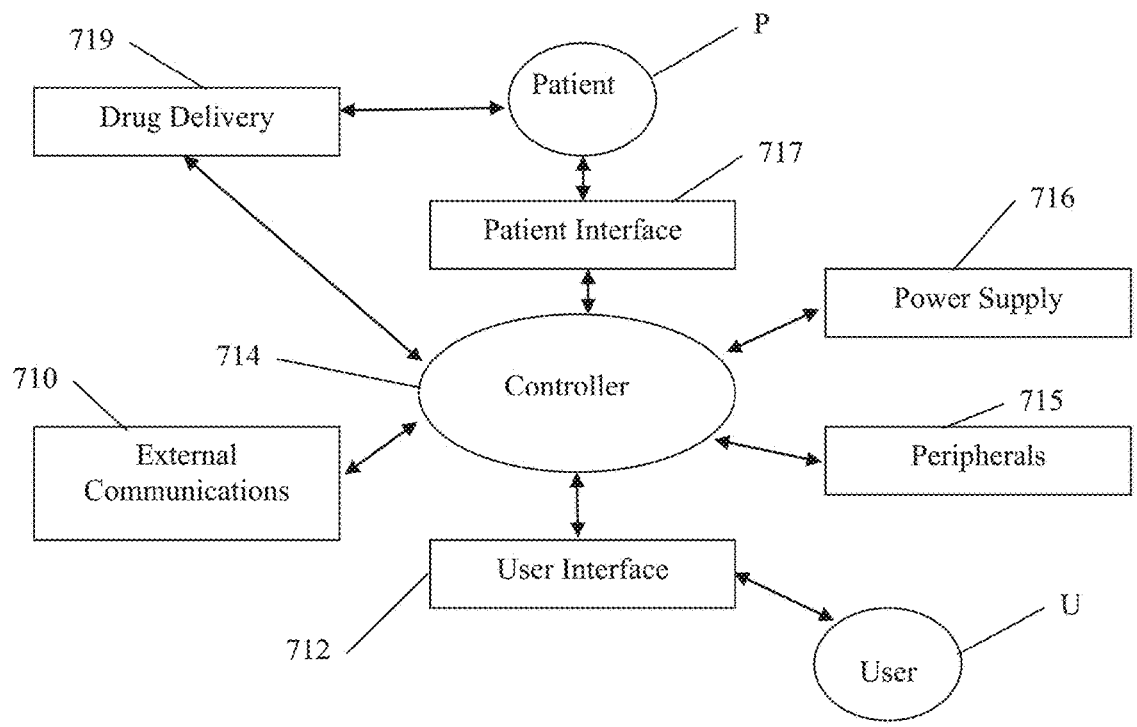

FIG. 43 is a block diagram illustrating a drug delivery system suitable for delivering sedation or analgesic drugs. The drug delivery system is integrated with an electrochemical sensor of the present invention to regulate drug delivery directly.

Figure 44:
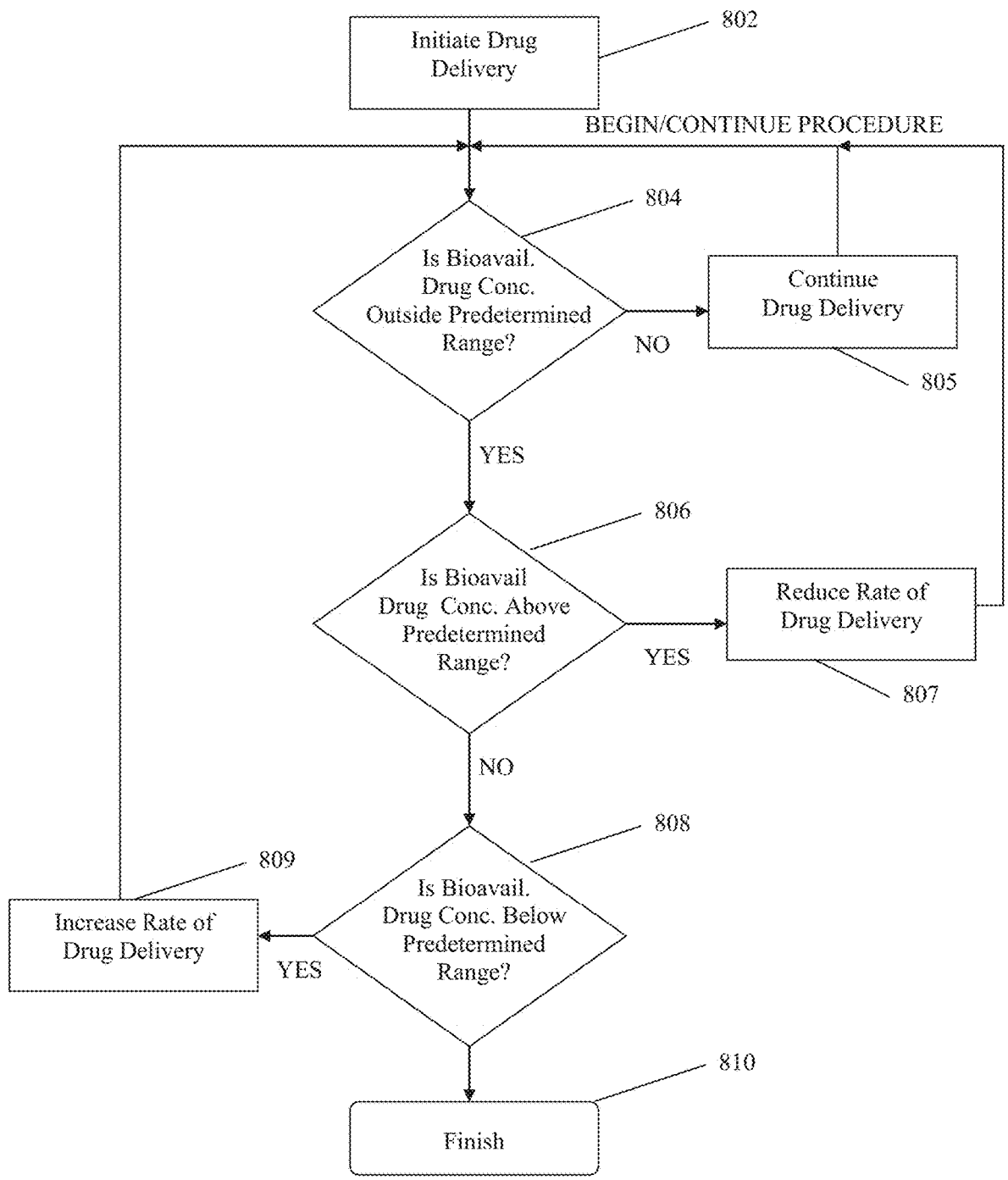

FIG. 44 is a flow chart of a method for detecting bioavailable drug concentration, i.e., in a patient, and then regulating the delivery rate of the drug to the patient in accordance with various aspects of this invention.

Figure 45A:

FIG. 45A shows a perspective view of a flex circuit, under an embodiment.

Figure 45B:
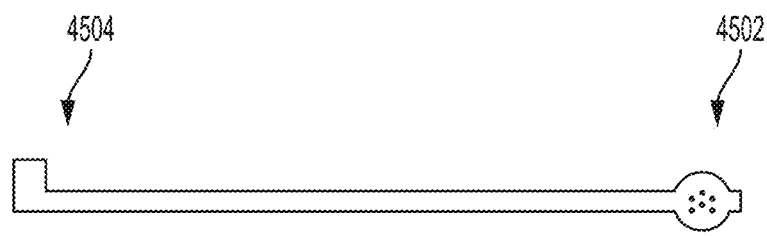

FIG. 45B shows a top down view of the flex circuit, under an embodiment.

Figure 45C:
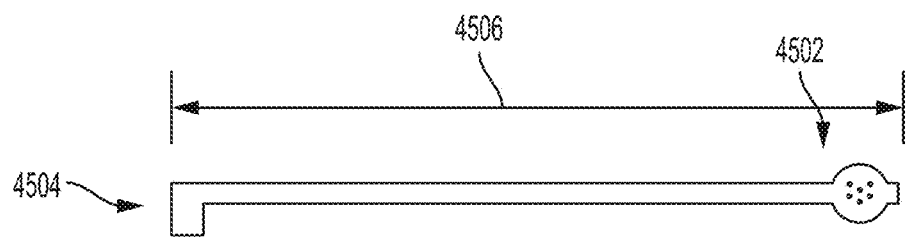

FIG. 45C shows a bottom up view of the flex circuit, under an embodiment.

Figure 46A:
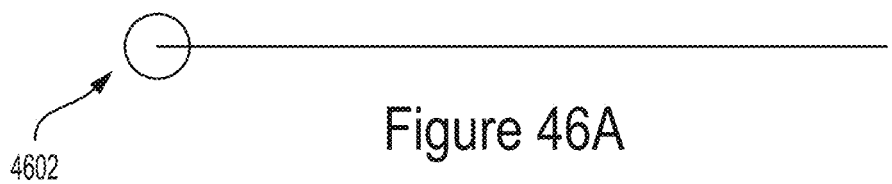

FIG. 46A shows a side view of the flex circuit, under an embodiment.

Figure 46B:
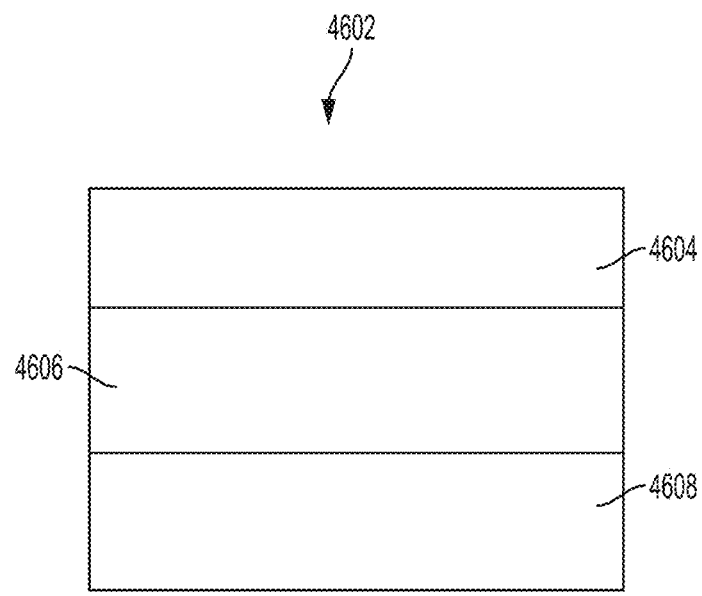

FIG. 46B provides a blow up illustration of the flex circuit's layered configuration, under an embodiment.

Figure 47:
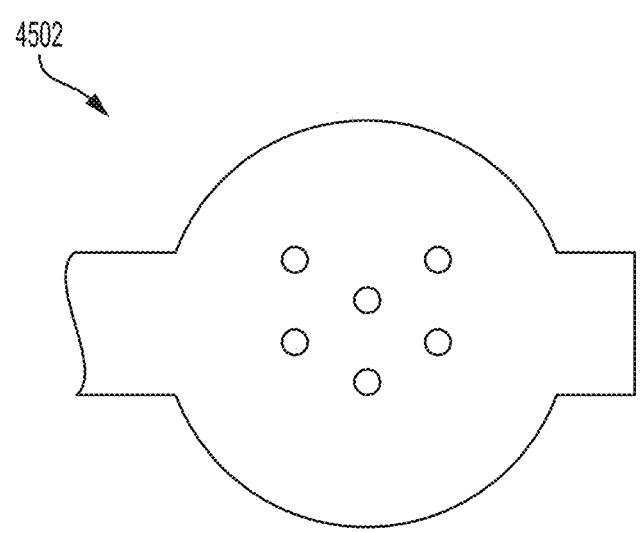

FIG. 47 provides a blow up view of the flex circuit's connection end, under an embodiment.

Figure 48A:
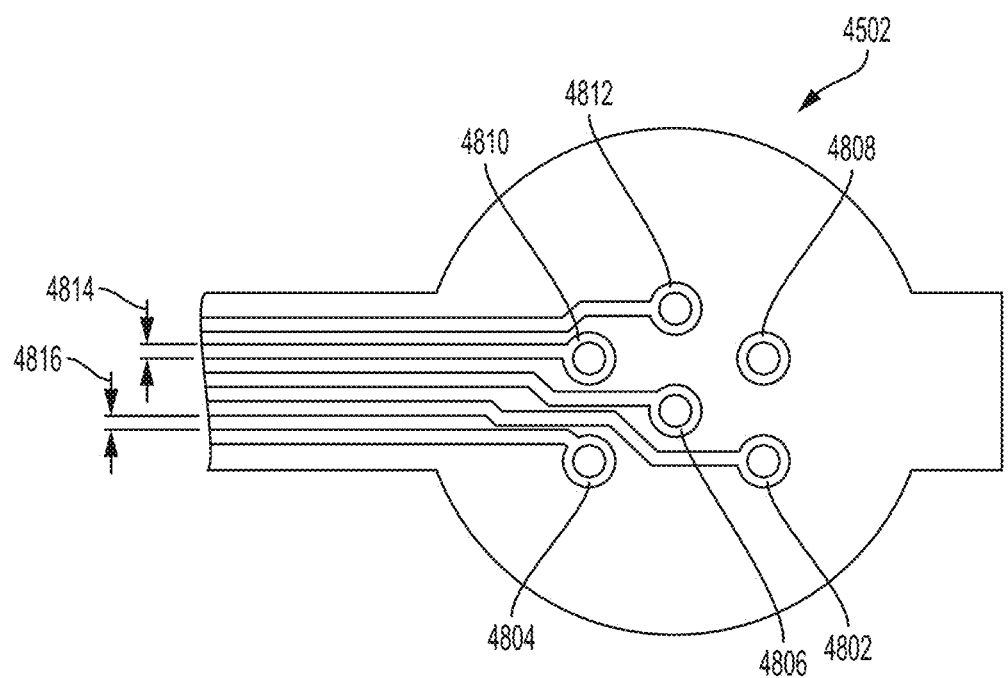

FIG. 48A provides a schematized blow up view of a flex circuit connection end, under an embodiment.

Figure 48B:
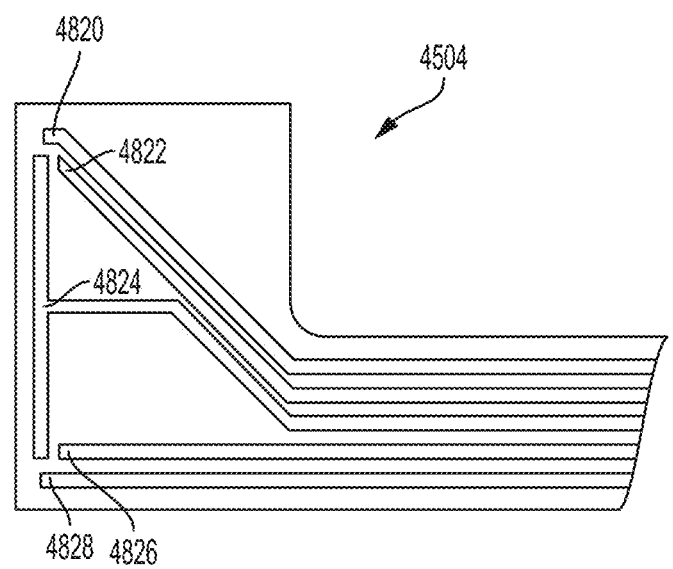

FIG. 48B shows a schematized blow up of a flex circuit sensor end, under an embodiment.

Figure 49:
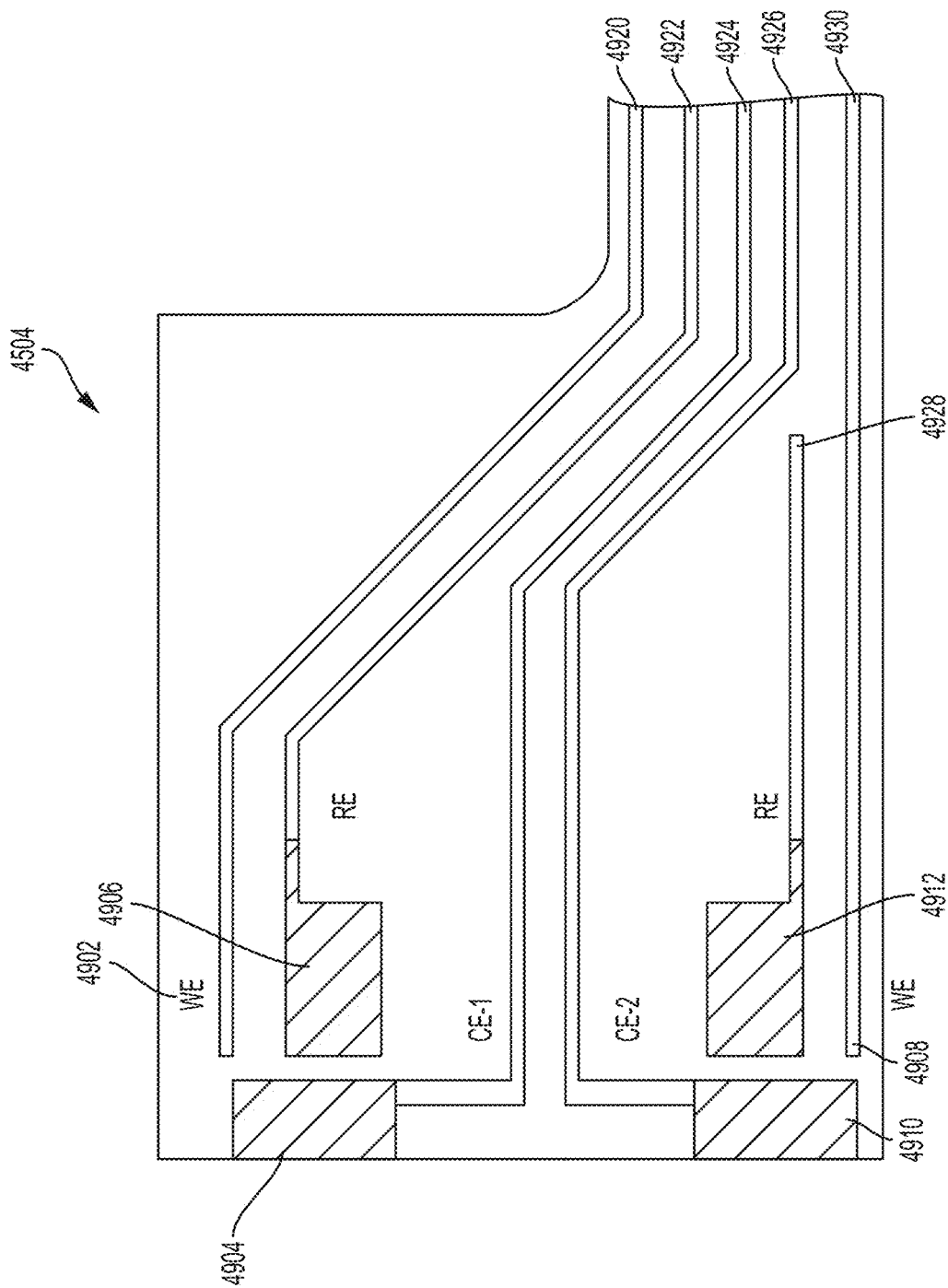

FIG. 49 shows an electrode array located at the flex circuit sensor end, under an embodiment.

Figure 50:
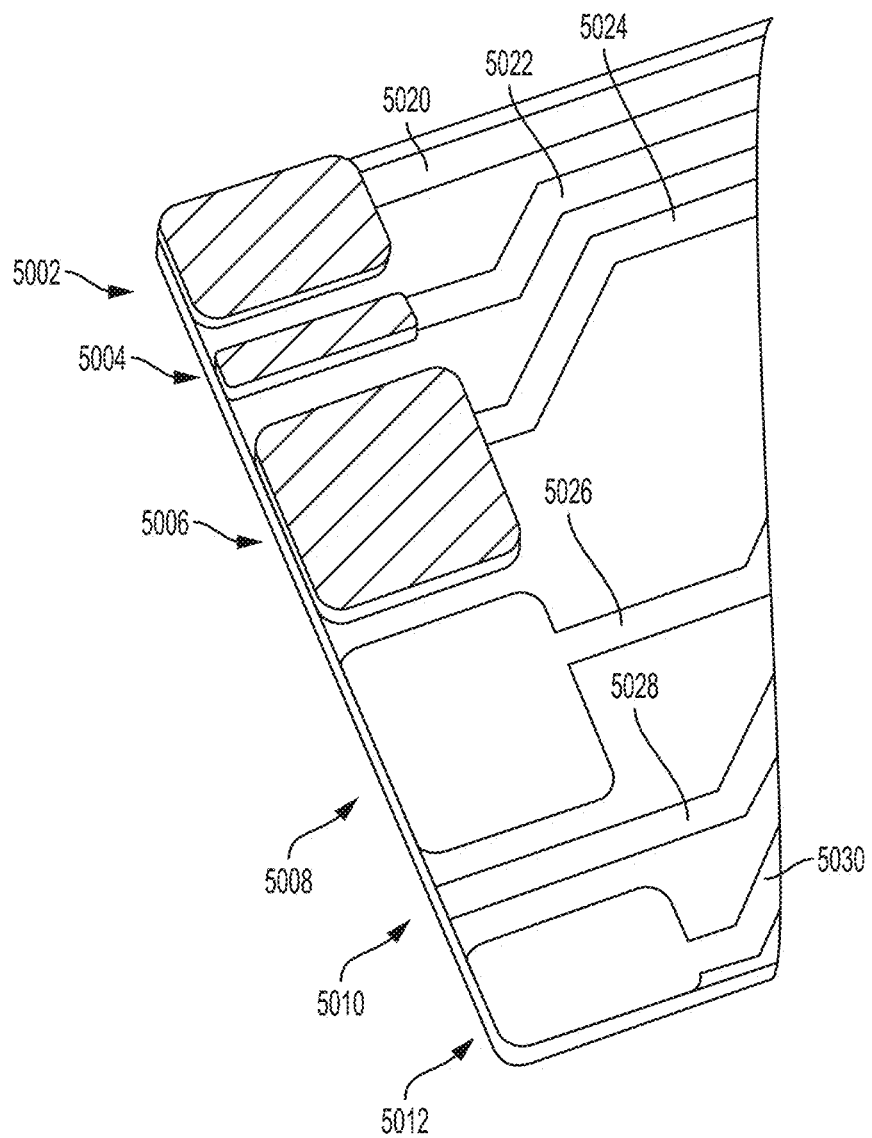

FIG. 50 shows an electrode array located at the flex circuit sensor end, under an embodiment.

Figure 51:
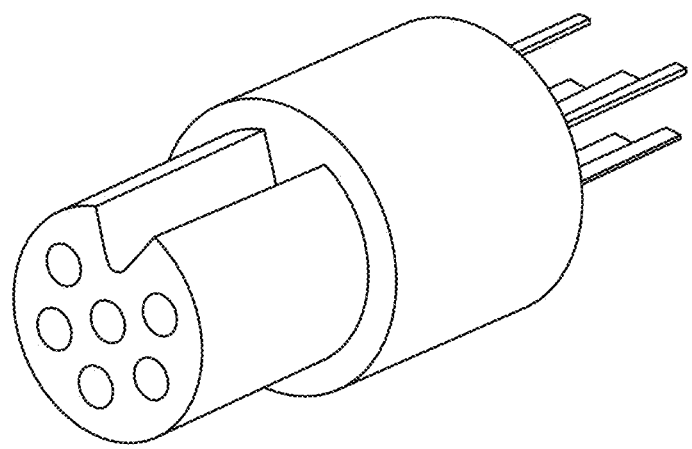

FIG. 51 shows an nano miniature circular connector, under an embodiment.

Figure 52:
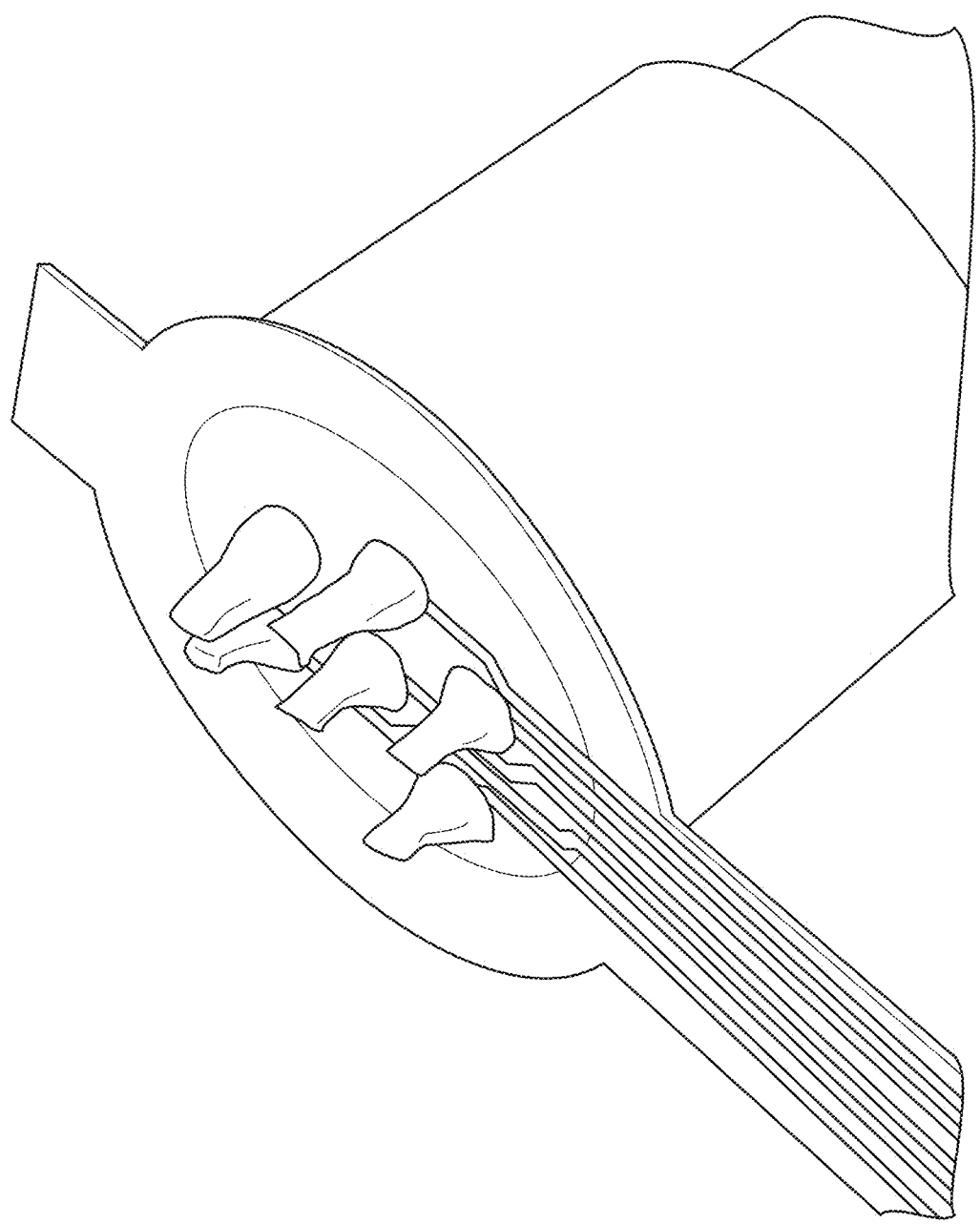

FIG. 52 shows a circular connector soldered and affixed to the surface of a flex circuit connection end, under an embodiment.

Figure 53:
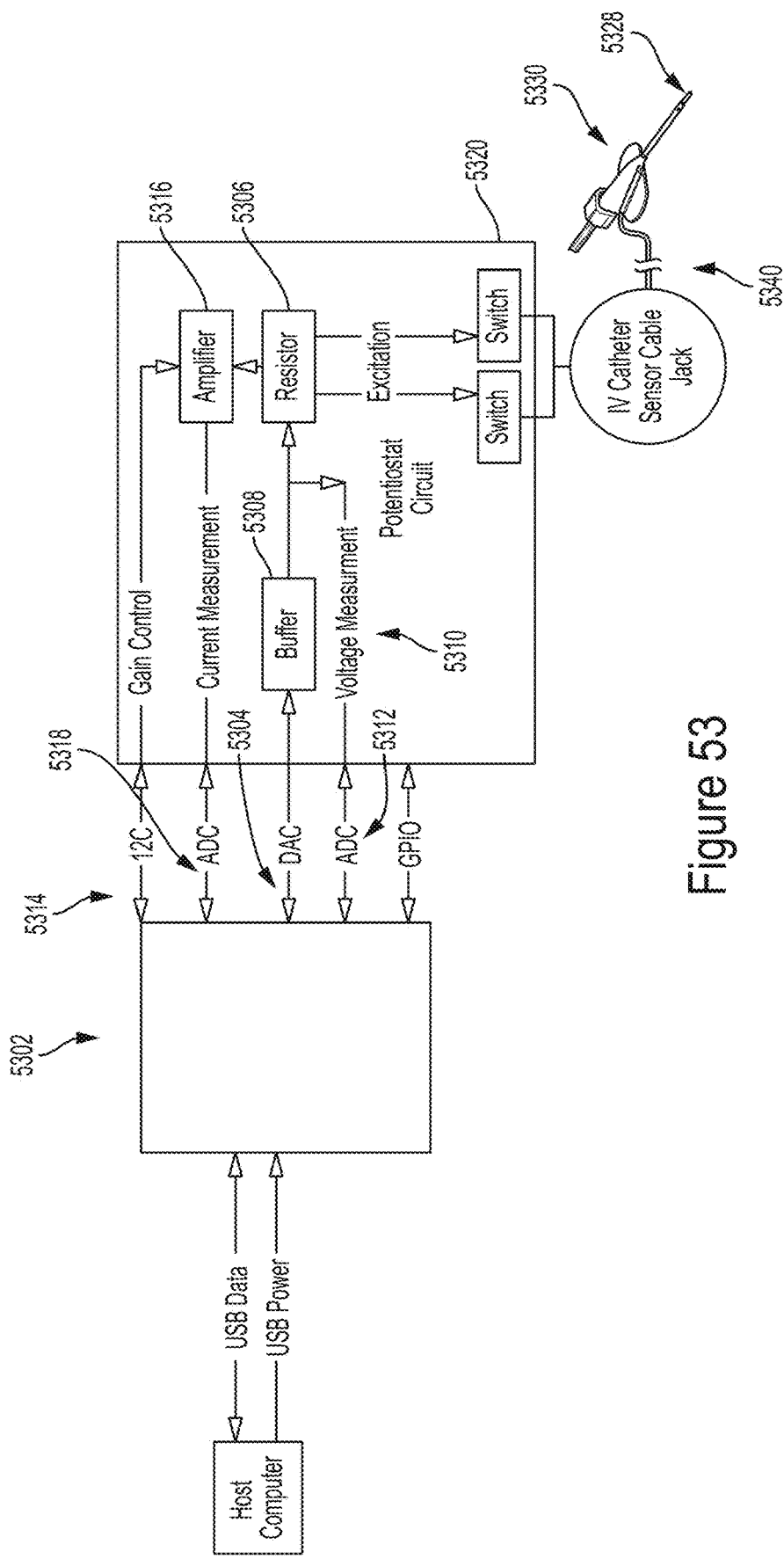

FIG. 53 shows a potentiostat circuit, under an embodiment.

Figure 54:
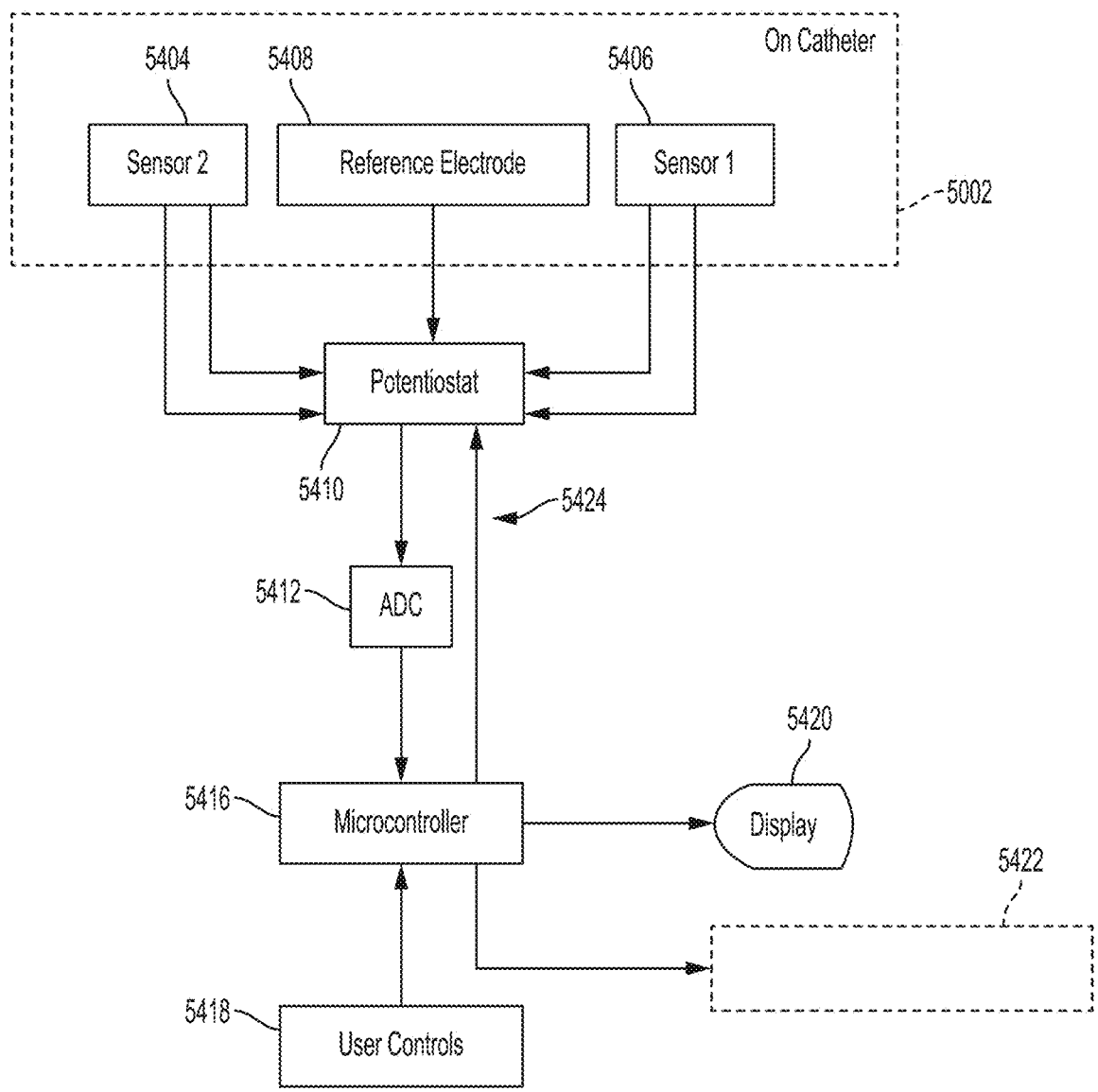

FIG. 54 shows a potentiostat circuit, under an embodiment.

Figure 55:
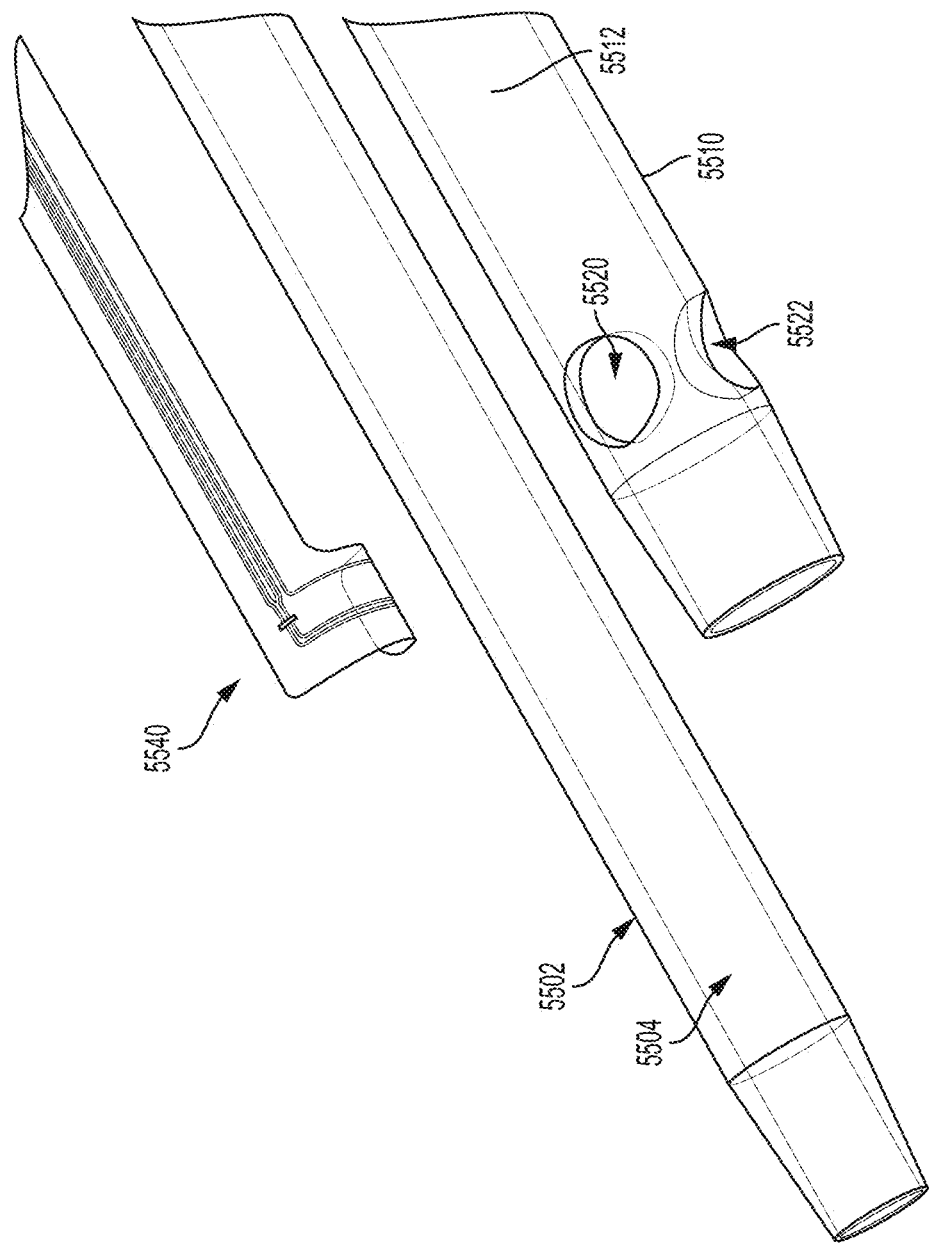

FIG. 55 shows components of a catheter, under an embodiment.

Figure 56:
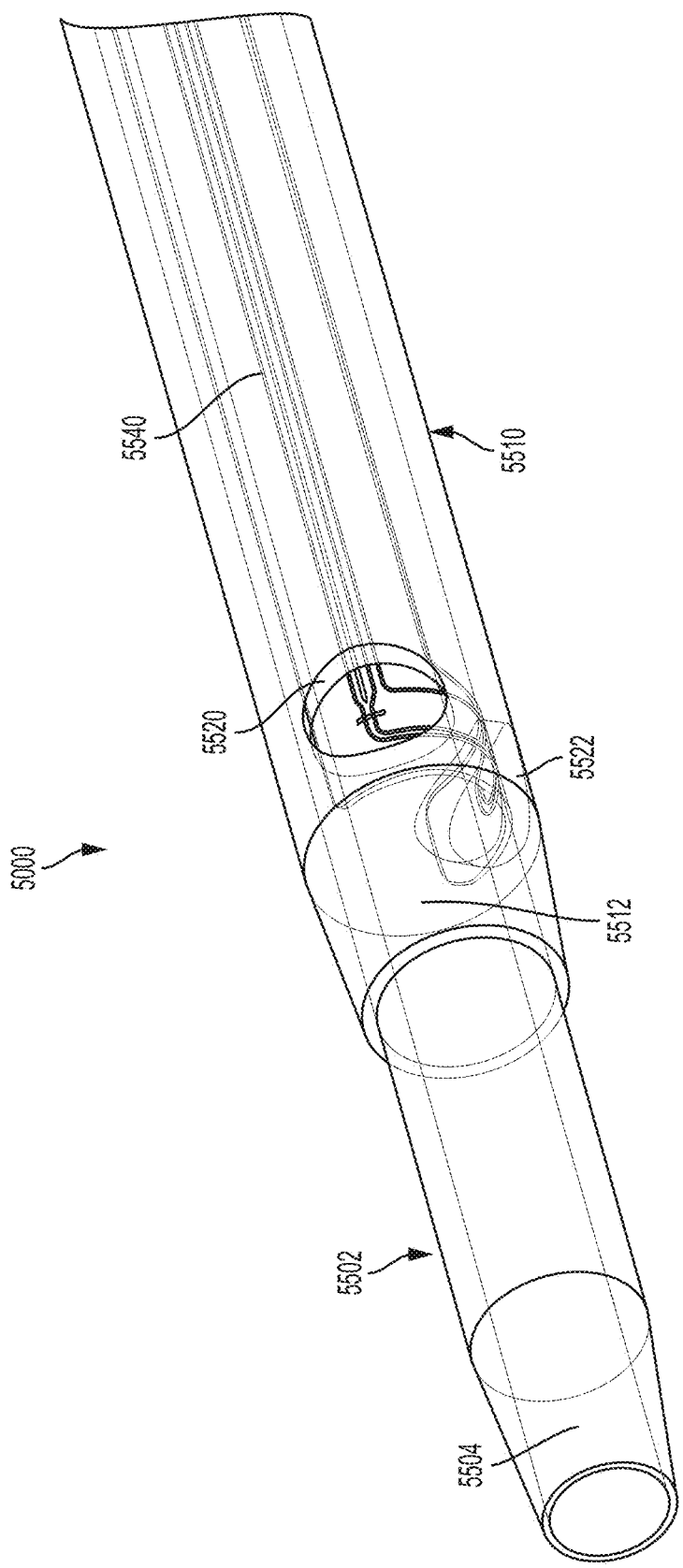

FIG. 56 shows components of a catheter, under an embodiment.

Figure 57:
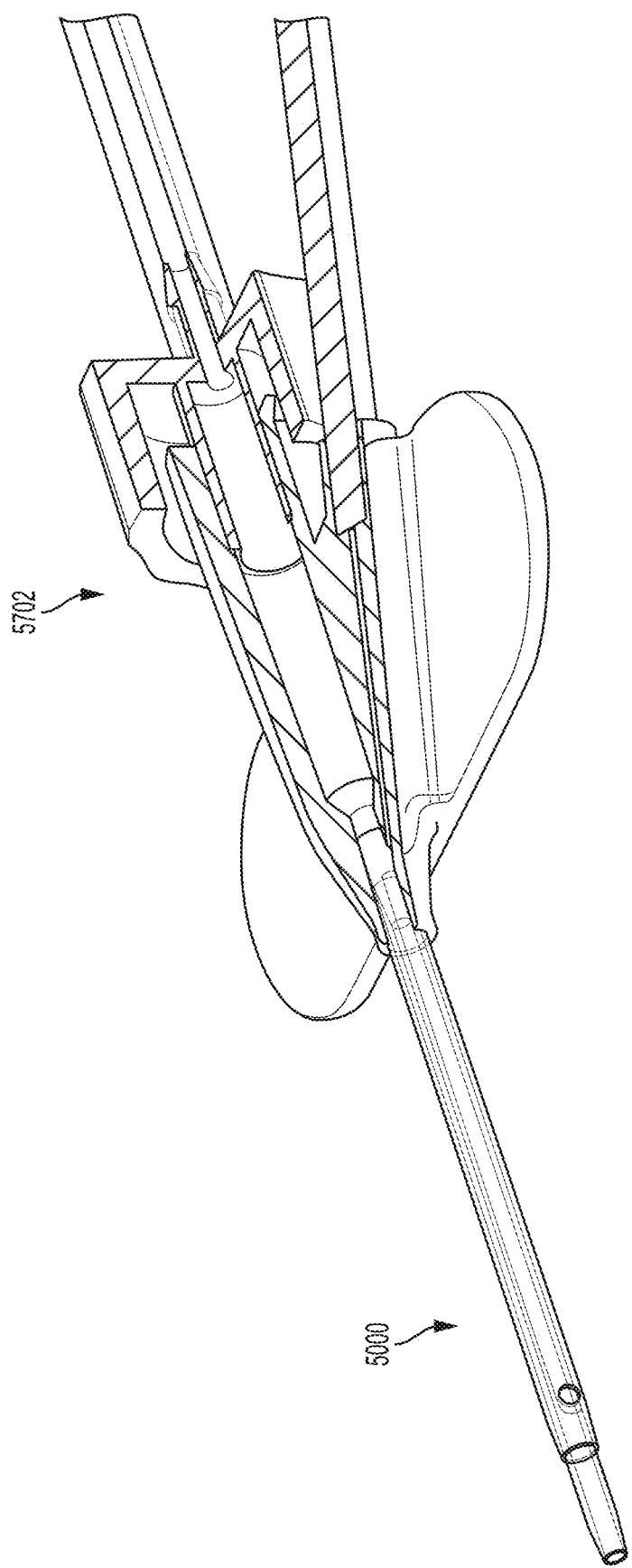

FIG. 57 shows components of a catheter apparatus connected to a docking component, under an embodiment.

Figure 58:
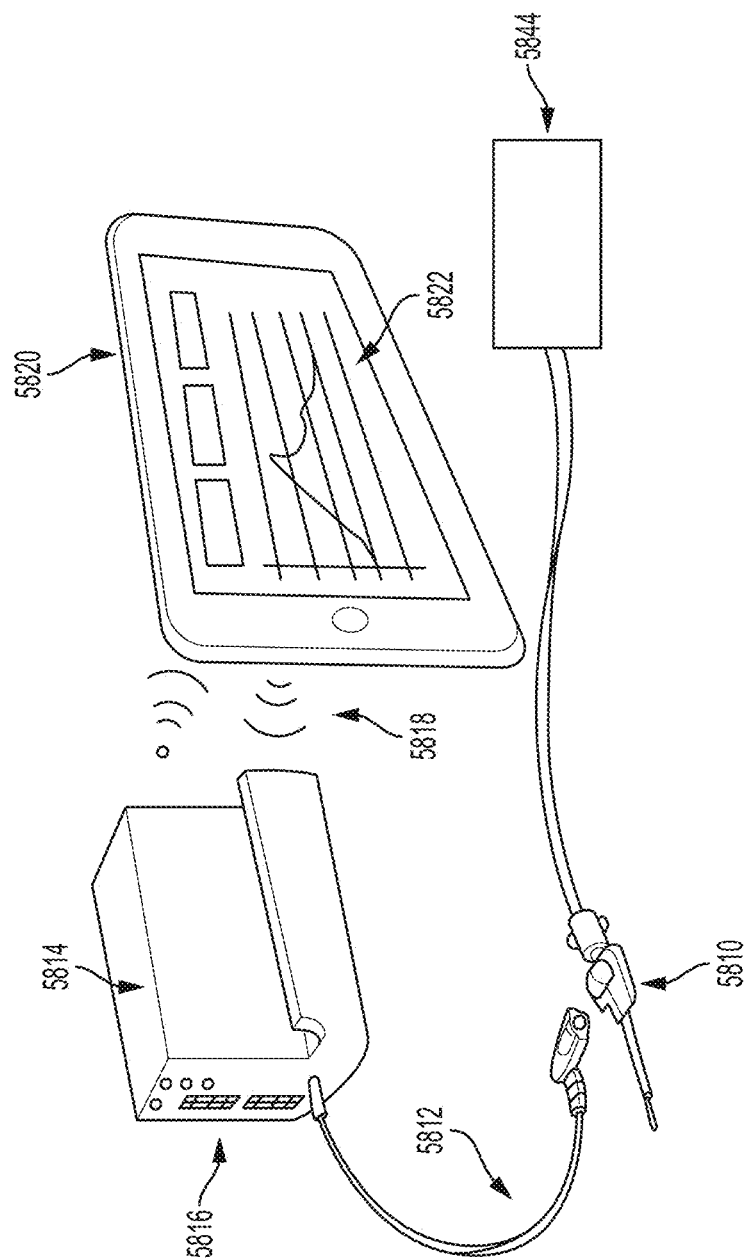

FIG. 58 shows a catheter apparatus coupled to an electronics box and mobile computing device, under an embodiment.

FIG. 59 shows a flex circuit, under an embodiment.

FIG. 60 shows a side view of the flex circuit, under an embodiment.

FIG. 61 shows a blow up side view of a connection end, under an embodiment.

Figure 62:
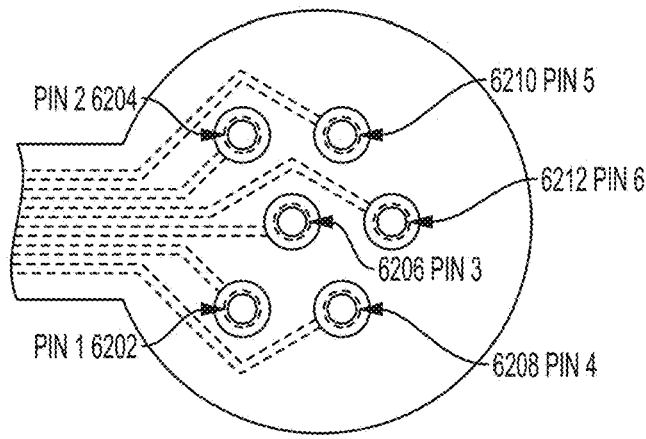

FIG. 62 shows a blow up of a flex circuit connection end, under an embodiment.

Figure 63:
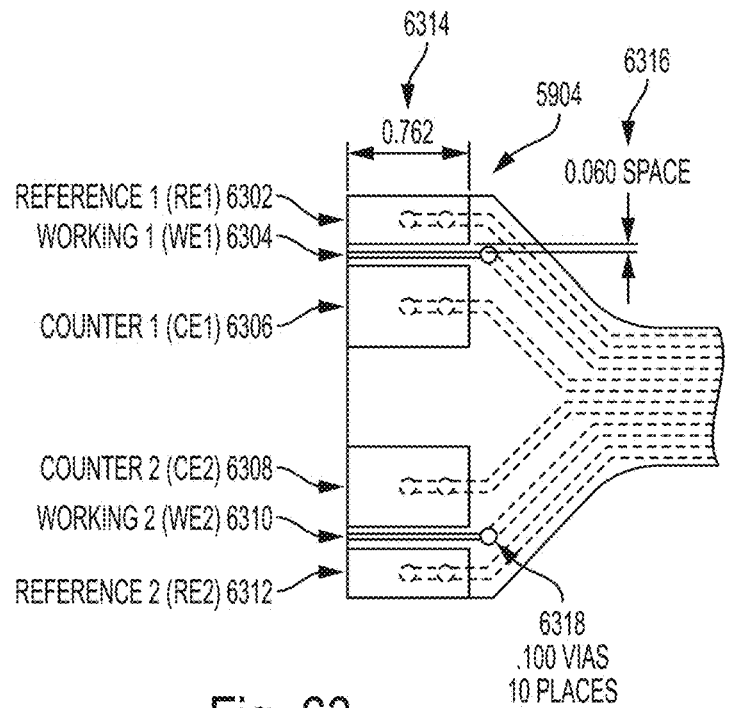

FIG. 63 shows a blow up of a flex circuit sensor end, under an embodiment.

Figure 64:
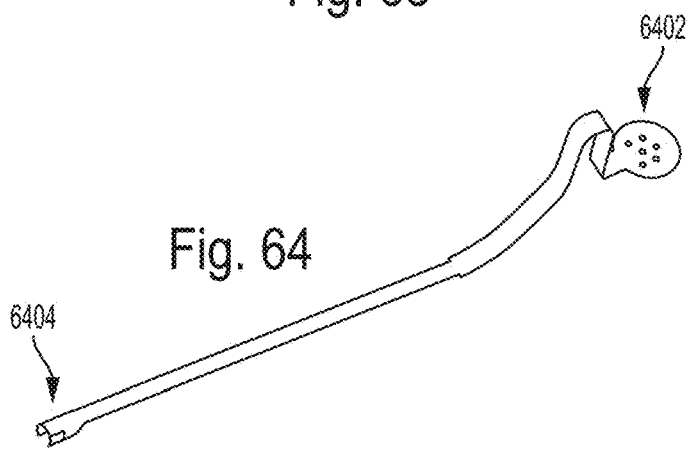

FIG. 64 shows a flex circuit, under an embodiment.

Figures 65A, 65B, 66, 67:
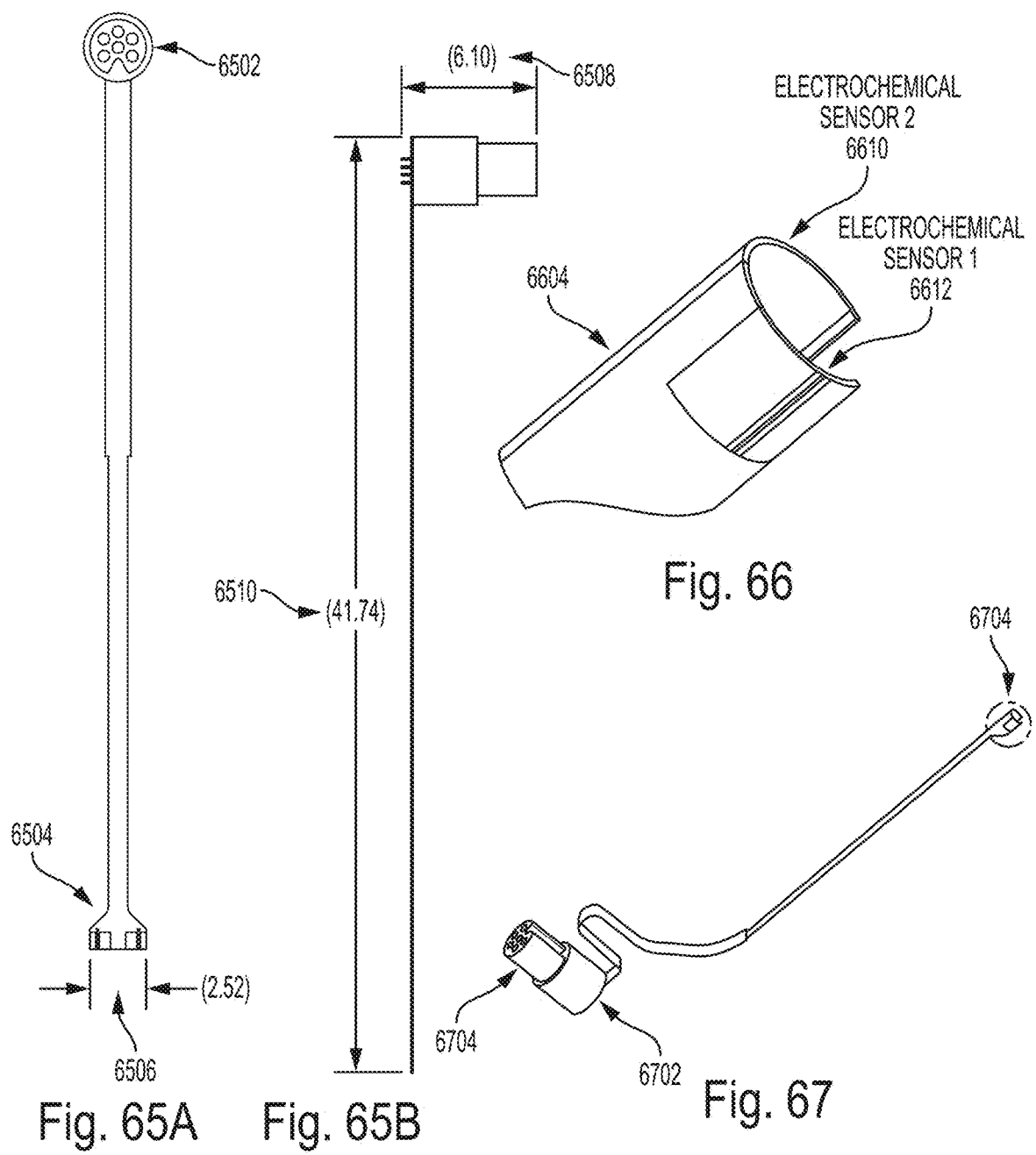

FIG. 65A shows a flex circuit with connection end soldered to a connector, under and embodiment.

FIG. 65B shows a side view of a flex circuit with connection end soldered to a connector, under and embodiment.

FIG. 66 shows a blow view of a flex circuit sensor end, under an embodiment.

FIG. 67 shows a flex circuit soldered to a connector at a connection end, under an embodiment.

Figures 68, 69:
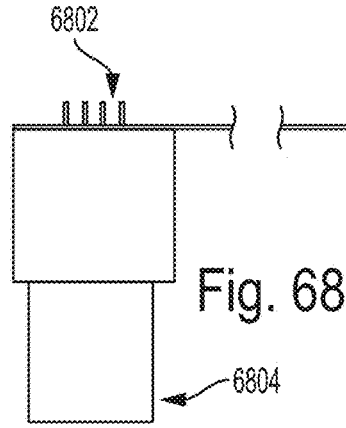

FIG. 68 shows a flex circuit connection end soldered to a connector, under an embodiment.

FIG. 69 shows a flex circuit soldered to a connector at a connection end, under an embodiment.

Figure 70:
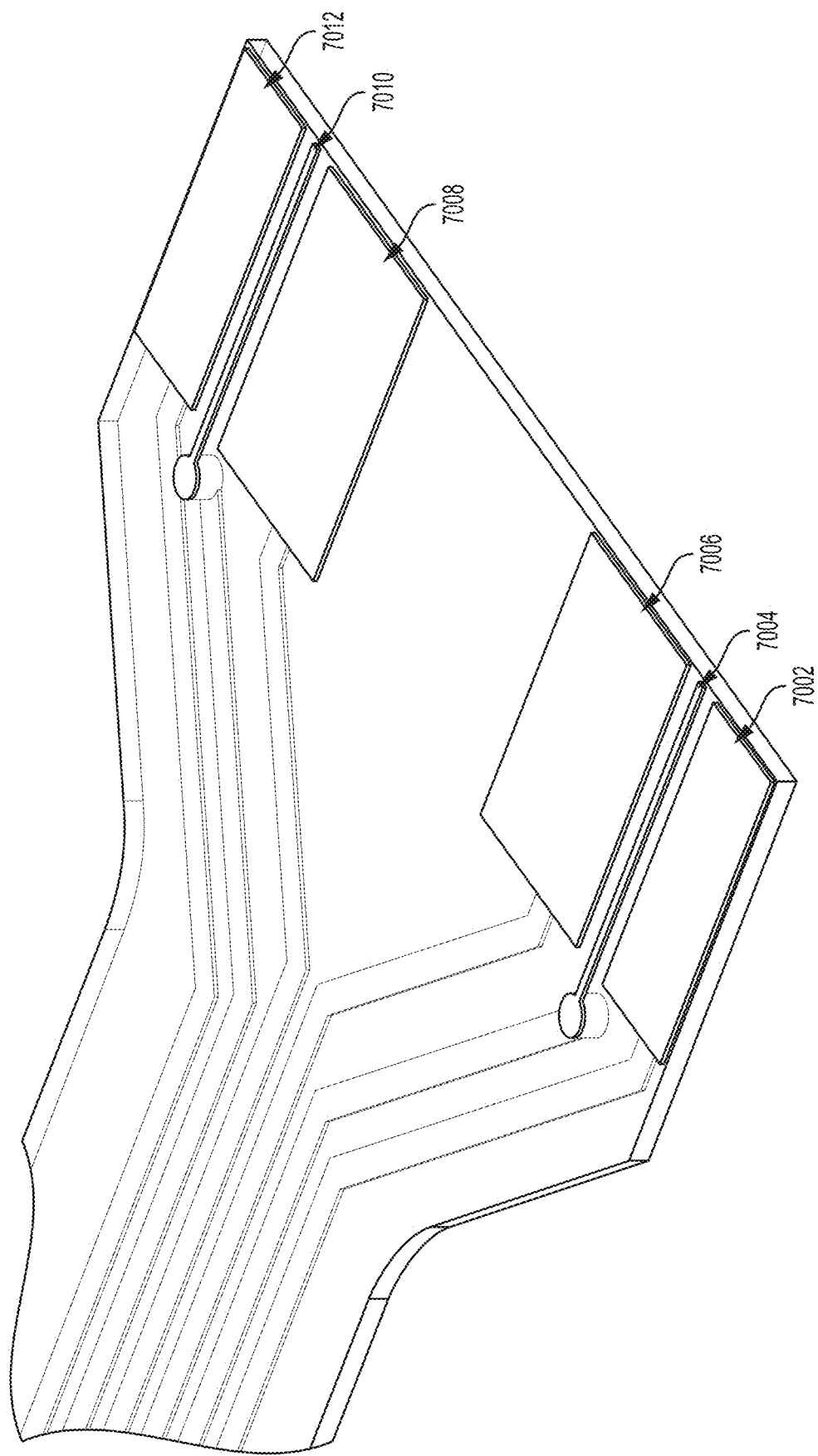

FIG. 70 shows a flex circuit sensor end, under an embodiment.

Figure 71:
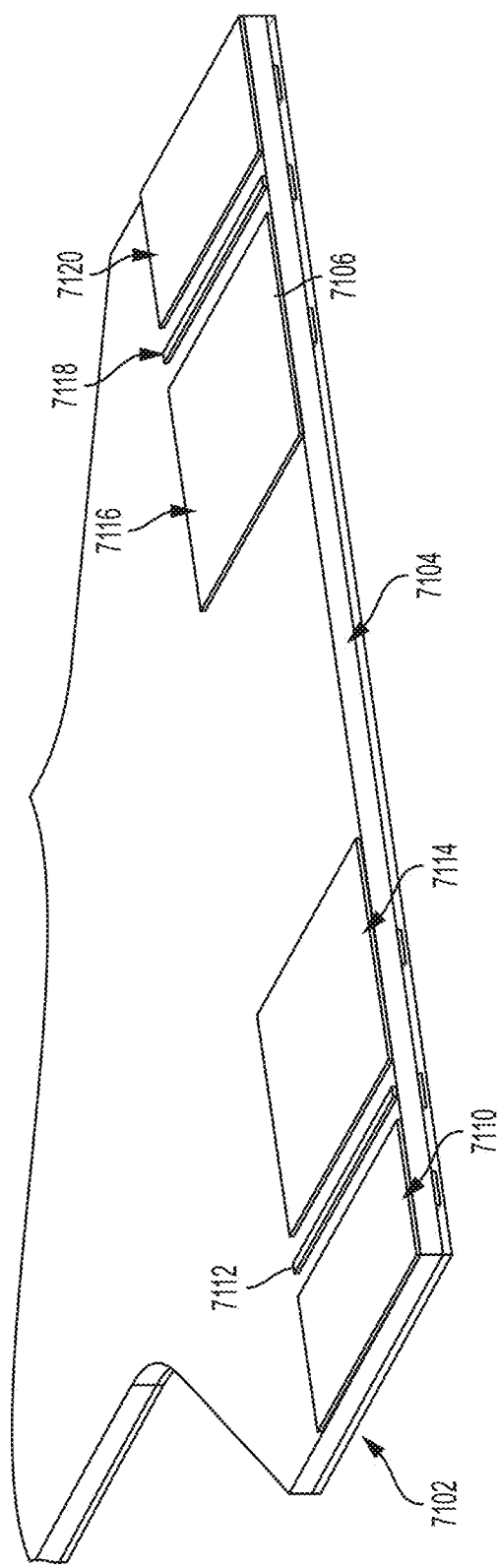

FIG. 71 shows a flex circuit sensor end, under an embodiment.

Figure 72:
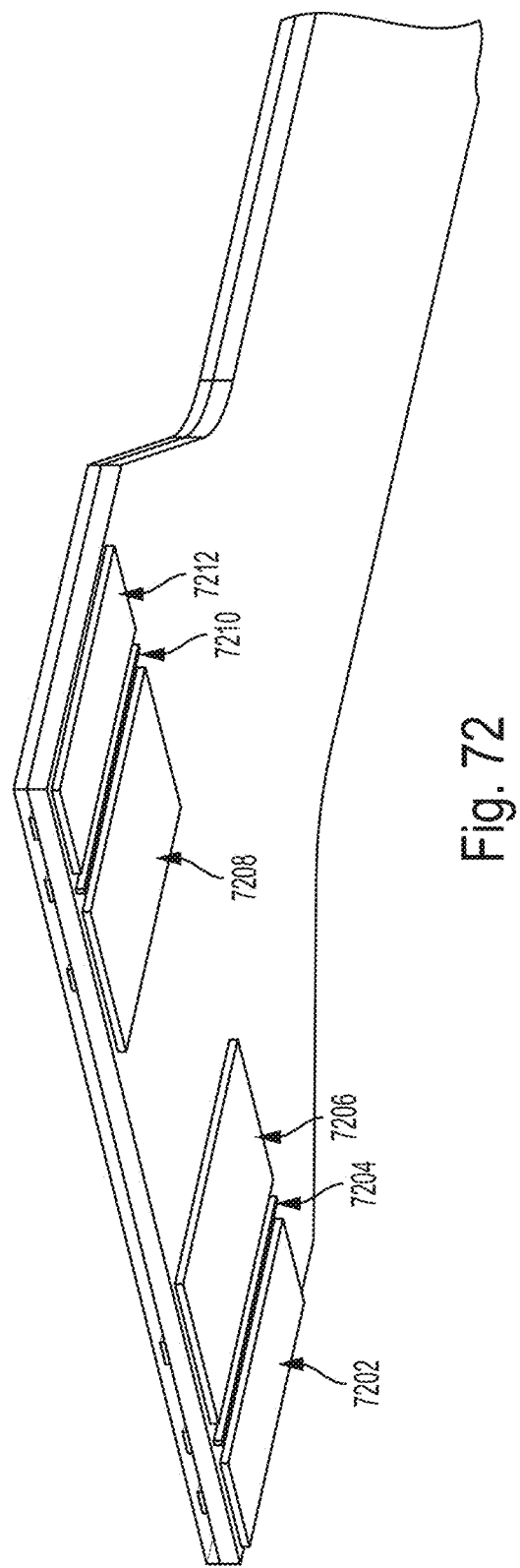

FIG. 72 shows a flex circuit sensor end, under an embodiment.

Figure 73:

FIG. 73 shows a flex circuit soldered to a connector at a connection end, under an embodiment.

Figure 74:
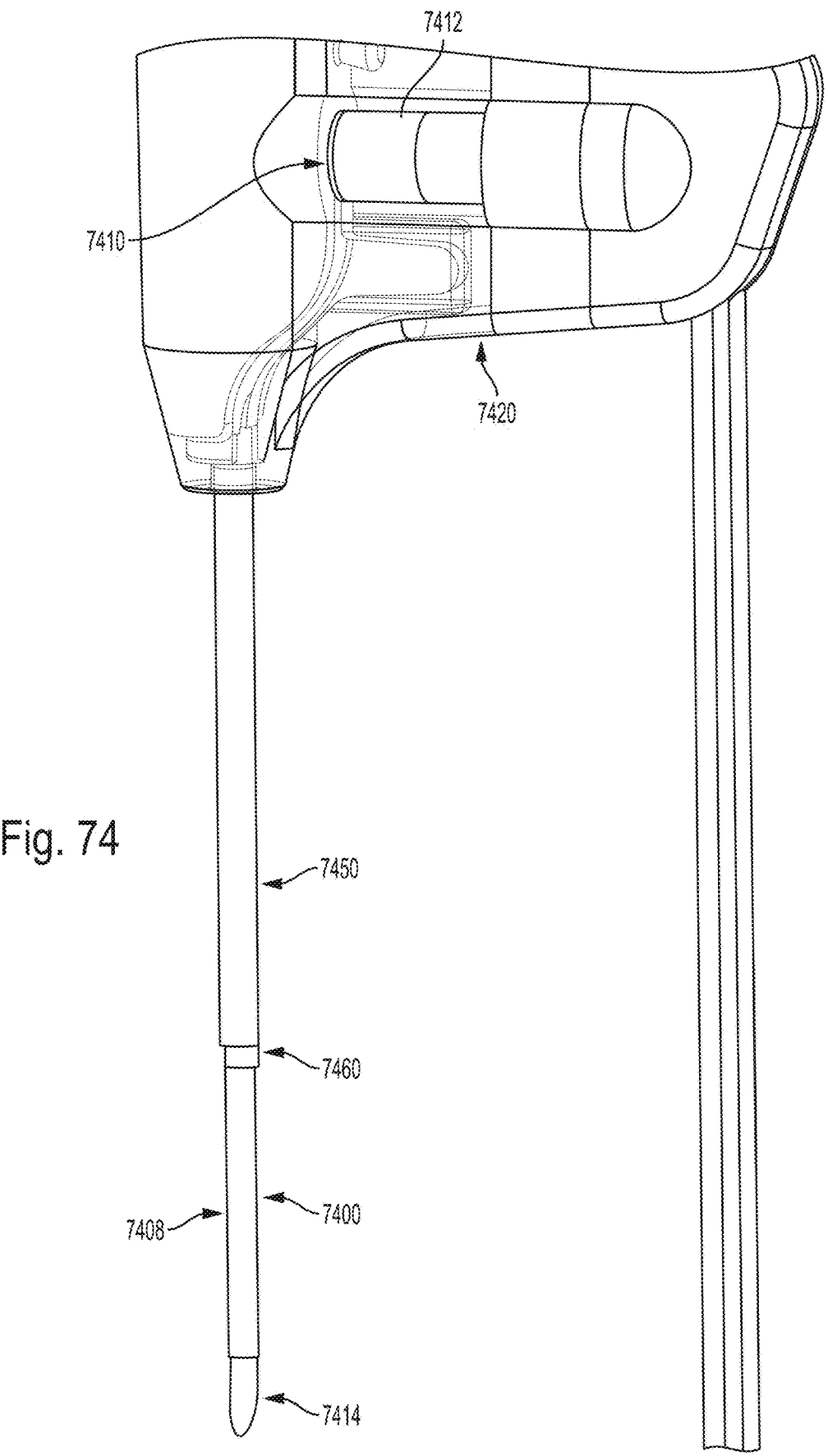

FIG. 74 shows a catheter device coupled to wiring using a flex circuit, under an embodiment.

Figure 75:
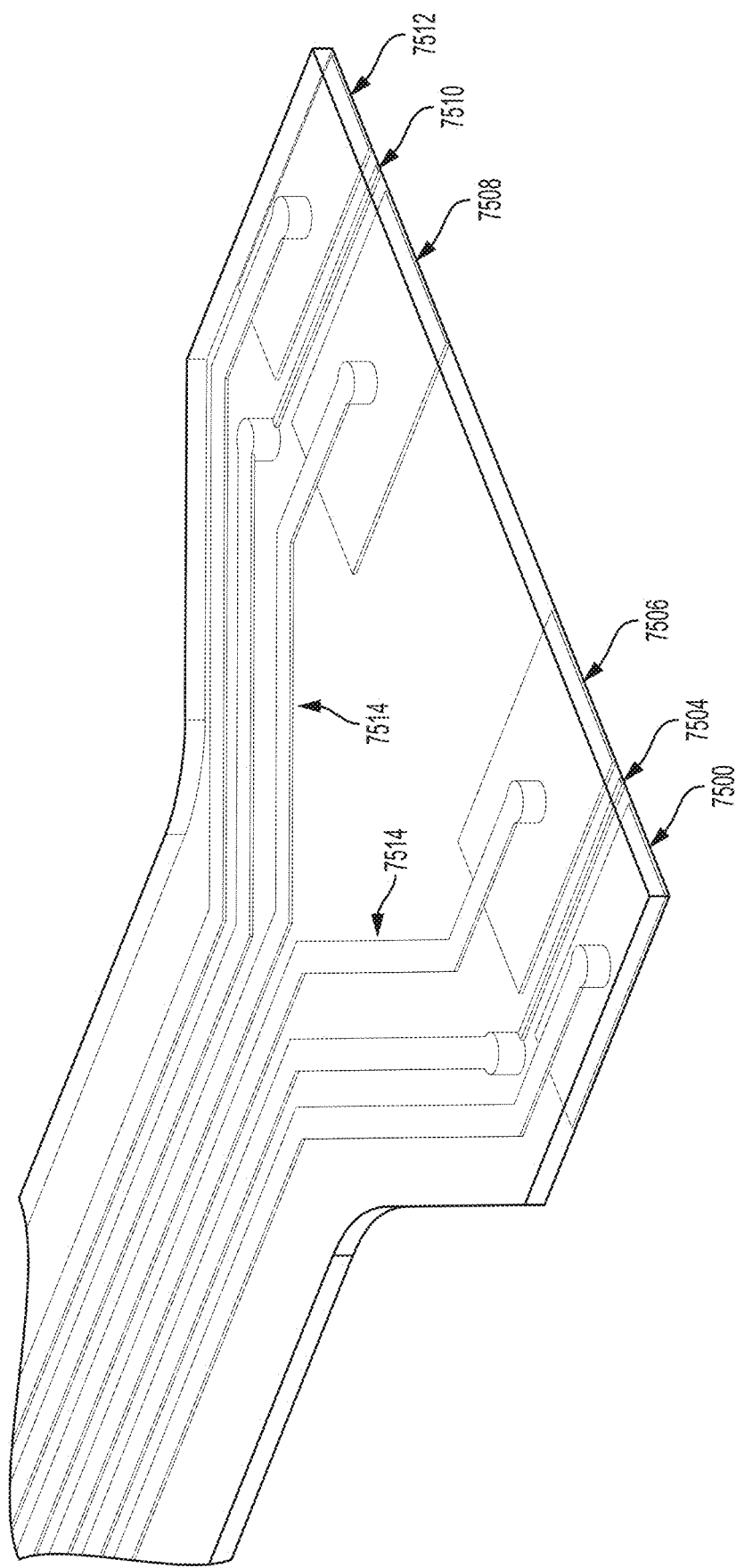

FIG. 75 shows a flex circuit sensor end, under an embodiment.

Figure 76:
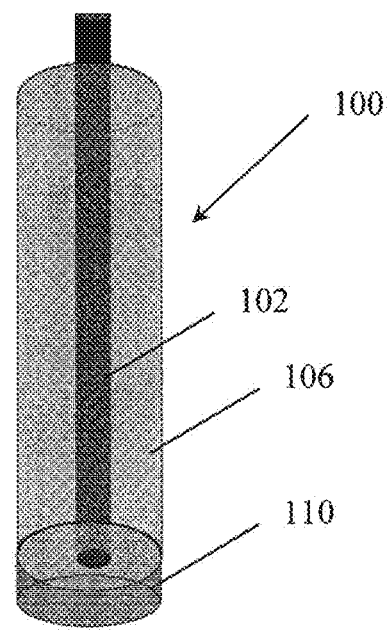

FIG. 76 shows a three dimensional representation of a single macroelectrode, where the electrode (e.g., carbon, gold, or platinum) is incorporated into an insulating matrix, e.g., glass, and the surface of the electrode is covered by a film or coating that is capable of partitioning the bioavailable drug from the sample.

Figure 77:
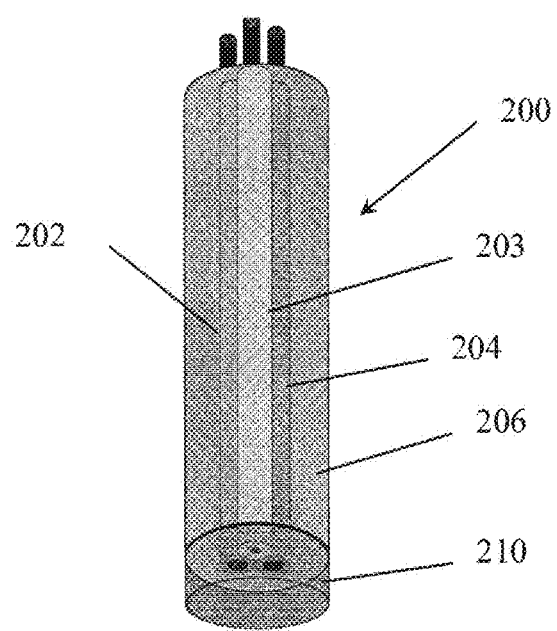

FIG. 77 shows a three dimensional representation of an electrochemical cell containing three electrodes (working, counter, and reference electrodes), where the surface of the entire electrochemical cell is coated with a film or coating that is capable of partitioning the bioavailable drug from the sample.

Figure 78:
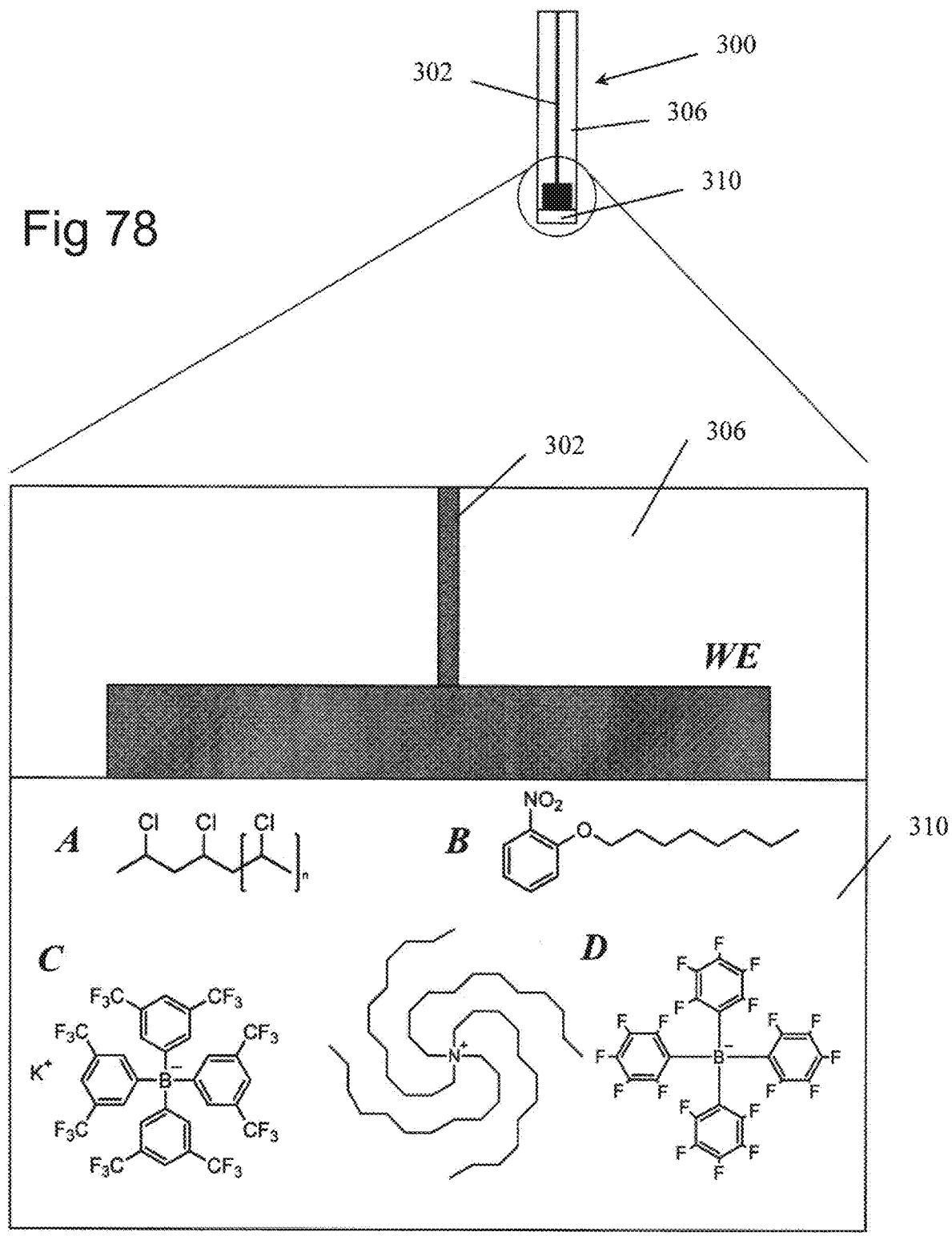

FIG. 78 shows a macroelectrode with the surface of the embedded carbon or metal disc-shaped working electrode (WE) covered by a film or coating that is capable of partitioning the bioavailable drug from the sample. In the enlarged portion of the Figure, the WE surface and coating are schematically illustrated. The graphite or metal working electrode (WE) material is embedded in an insulator matrix. The coating includes A, chemical representation of PVC, which is an example of the structural component of the membrane; B, chemical representation of 2-nitrophenyl octyl ether, an example of the water immiscible organic solvent of the membrane; C, chemical representation of potassium tetrakis [3,5,bis (trifluoromethyl) phenyl] borate as an exemplary ion exchange component of the membrane; and D, chemical representation of the exemplary resistance controlling component tetradodecylammonium tetrakis(pentafluorophenyl) borate.

Figure 79A:
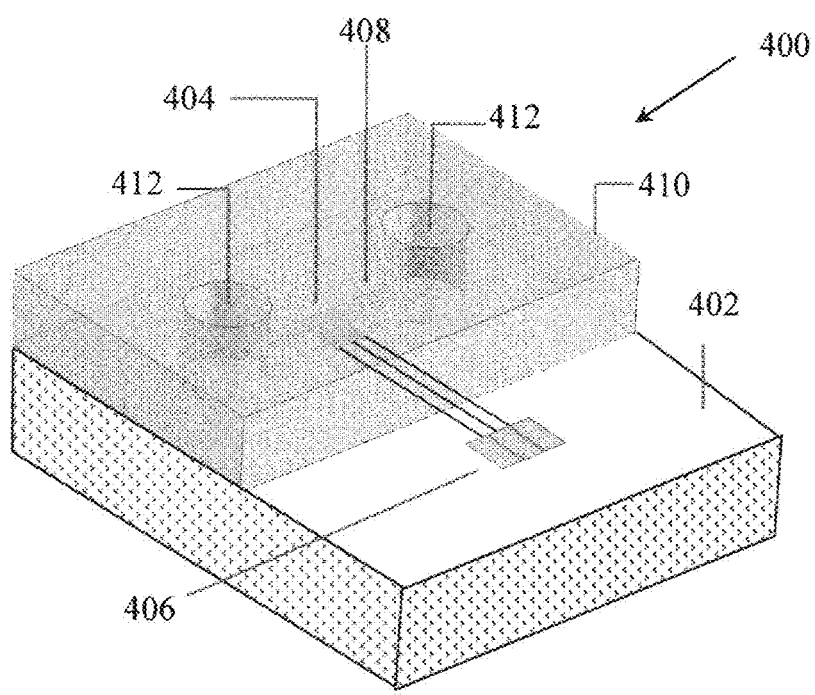

FIG. 79A is a perspective view illustrating one embodiment of a microfluidic device containing an electrochemical cell integrated into a flow channel of the microfluidic device.

Figure 79B:
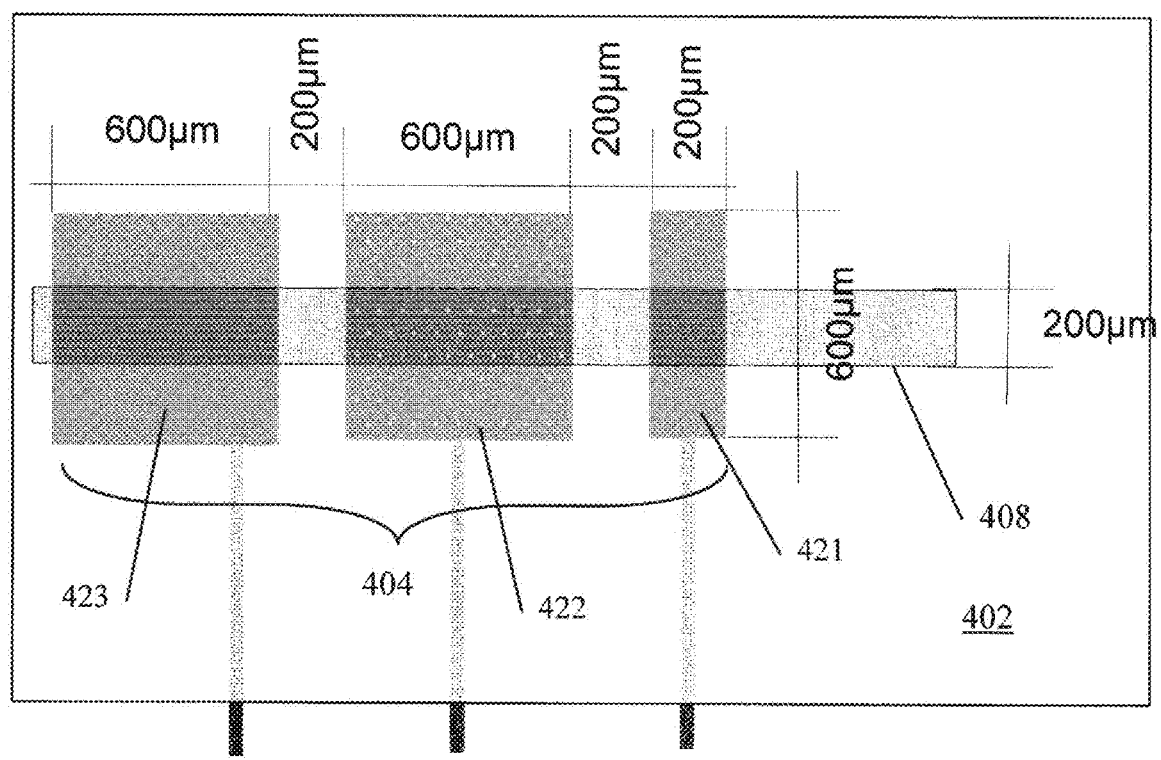

FIG. 79B illustrates the structure of a microdisc array comprising working, counter, and reference electrodes, with the working electrode covered by a coating of the present invention, and the microfluidic channel passing across each electrode of the array.

Figure 80:
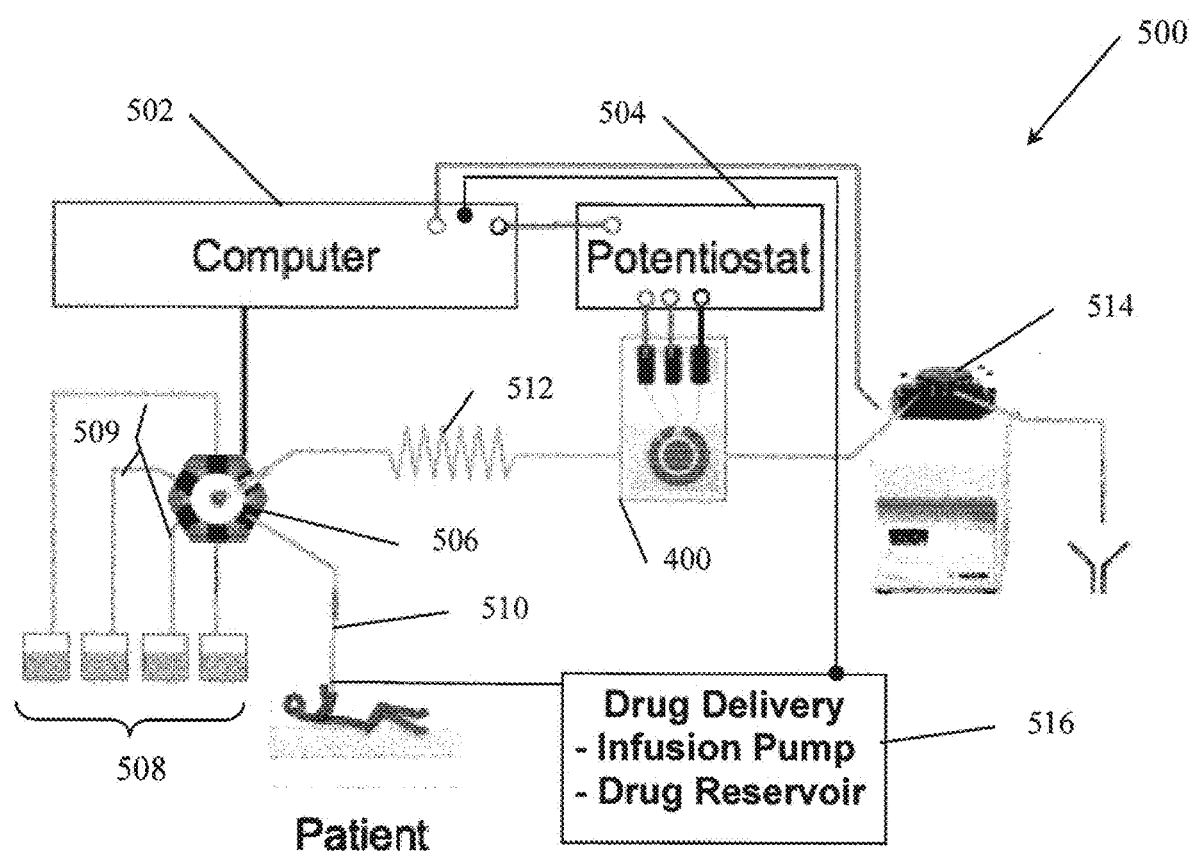

FIG. 80 illustrates one example of an ex vivo sensor device, which can be used for the feedback controlled delivery of propofol or other electrochemically active drugs or metabolites.

Figure 81:
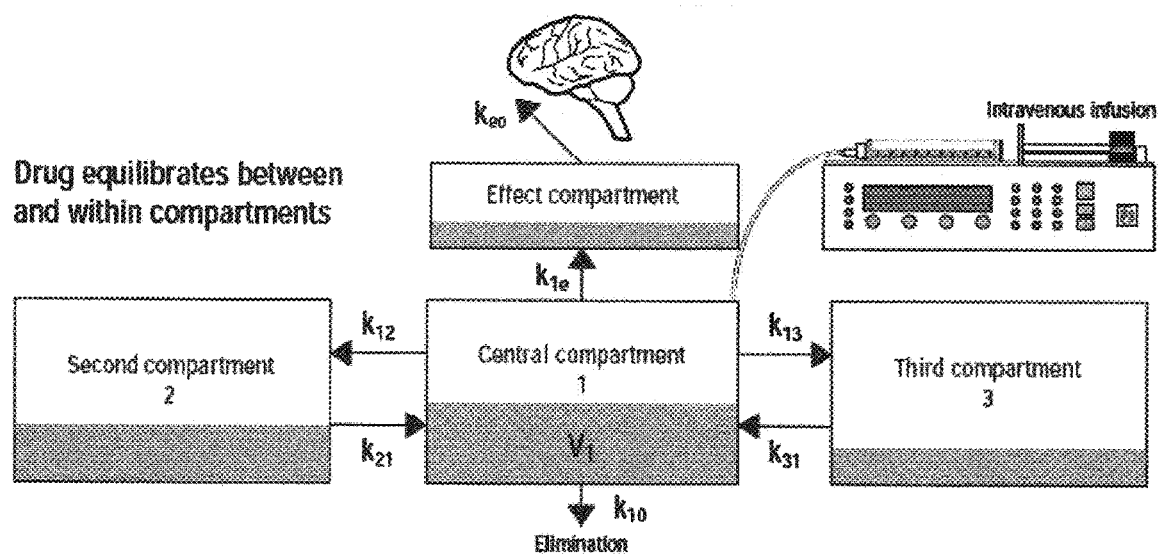

FIG. 81 illustrates that the bioavailable drug concentration can be detected in blood/lymph (central compartment), CSF (second compartment), or exhaled breath (third compartment).

Figure 82:
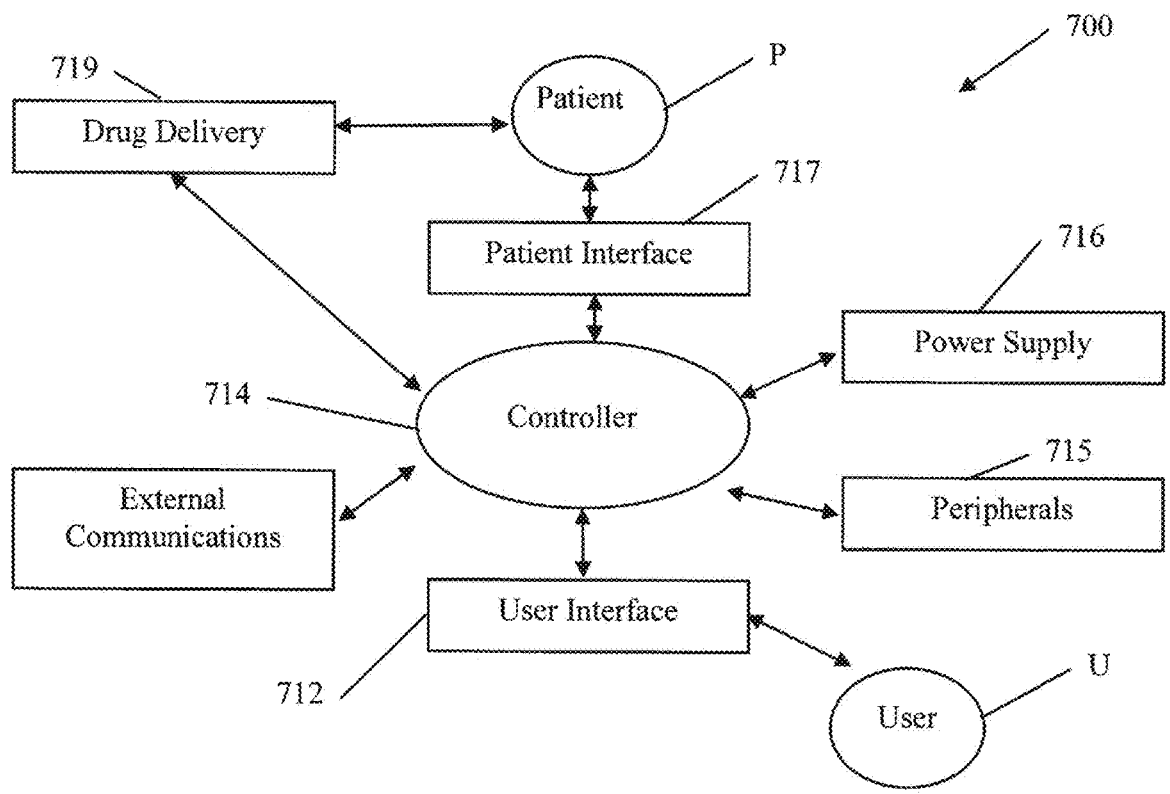

FIG. 82 illustrates a block diagram depicting one embodiment of a drug delivery system that is equipped with an electrochemical sensor of the invention.

Figure 83:
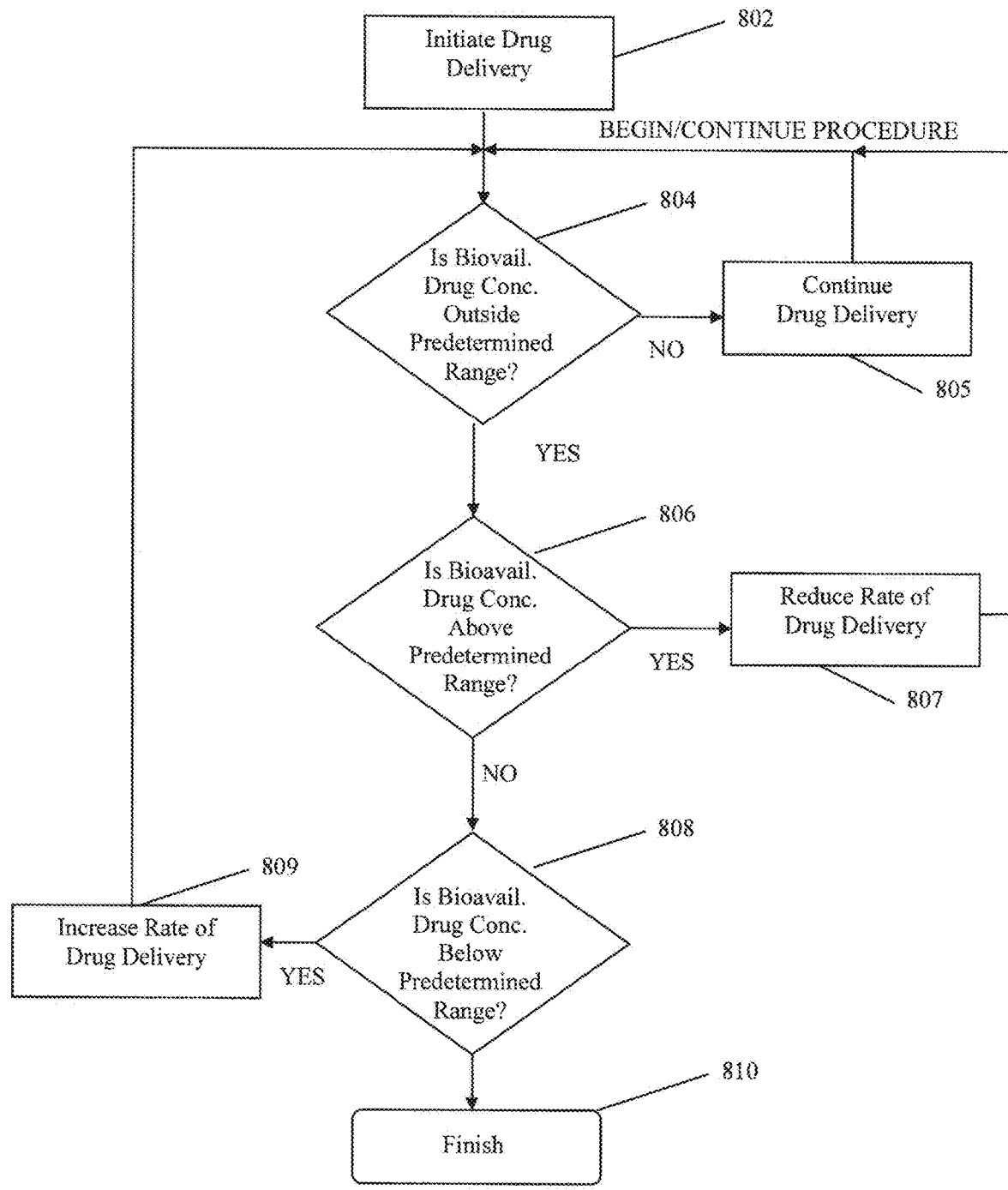

FIG. 83 is a diagram illustrating one method of modulating drug delivery.

Figure 84:
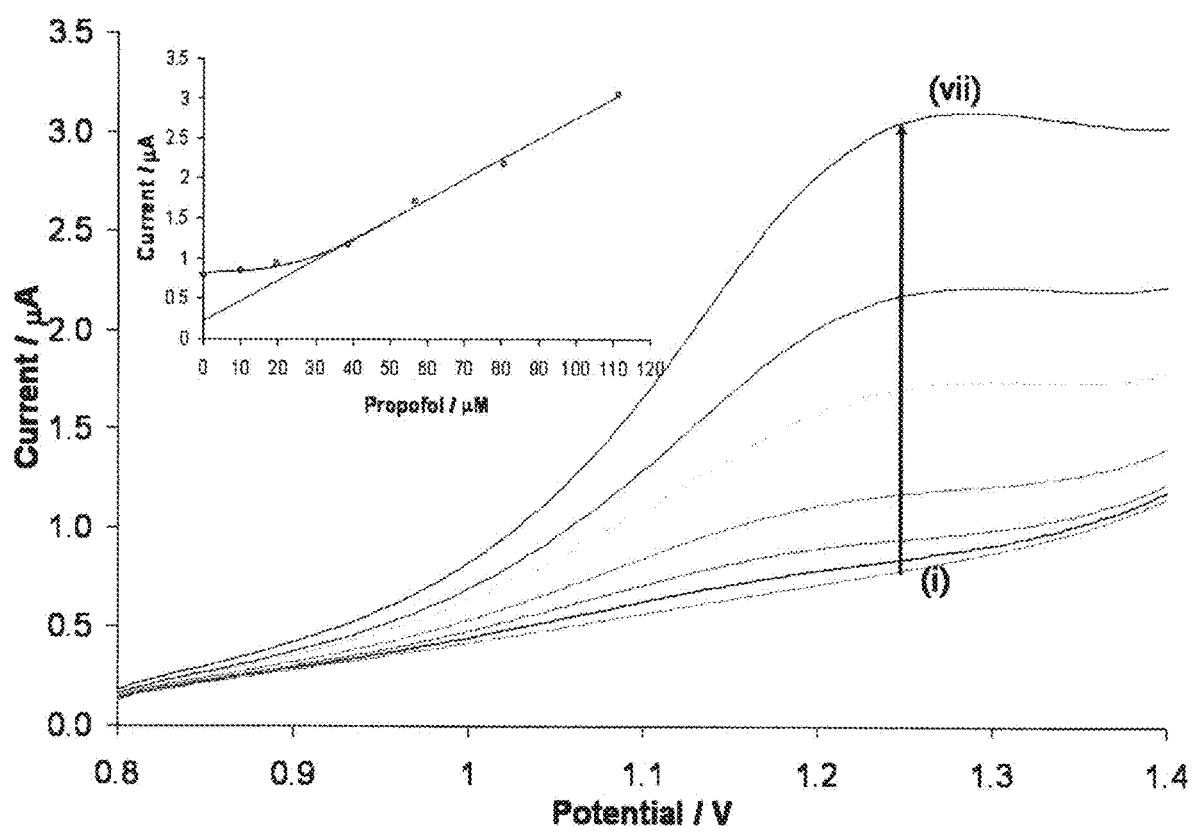

FIG. 84 shows forward CV scans recorded with a PVC-membrane coated GC electrode (Solution I), for (i)=0 $\mu$M; (ii)=9.9 $\mu$M; (iii)=19.6 $\mu$M; (iv)=38.5 $\mu$M; (v)=56.6 $\mu$M; (vi)=80.5 $\mu$M; (vii)=111.1 $\mu$M propofol in PBS. Inset: Calibration curve for propofol based on peak current measurements at 1.25 V.

Figure 85:
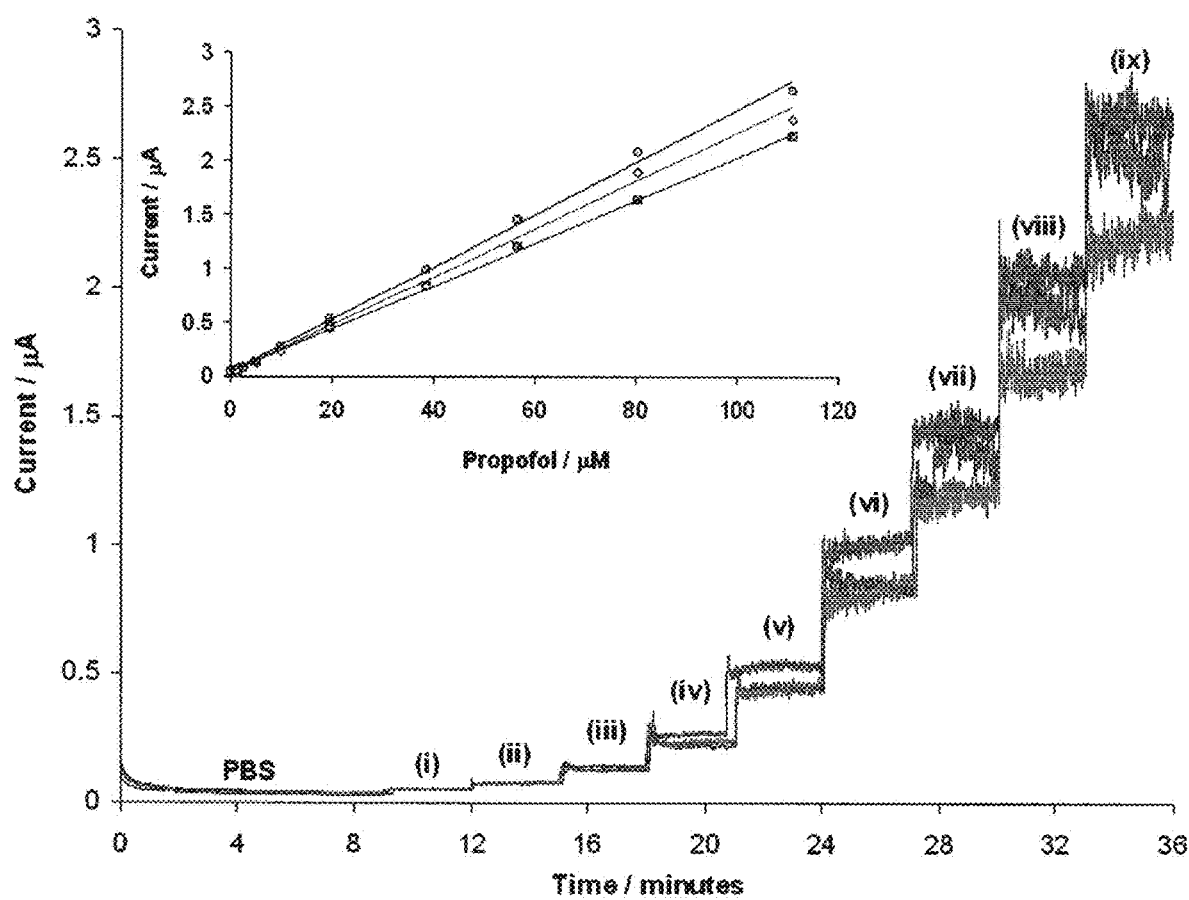

FIG. 85 shows CA response of PVC-membrane coated GC electrode (Solution I), for (i)=1.25 $\mu$M; (ii)=2.5 $\mu$M; (iii)=4.98 $\mu$M; (iv)=9.9 $\mu$M; (v)=19.6 $\mu$M; (vi)=38.4 $\mu$M; (vii)=56.6 $\mu$M; (viii)=80.5 $\mu$M; (ix) 111.1 $\mu$M propofol in PBS buffer. Top inset: Calibration curves for propofol based on current measurements after 2 minutes of each addition.

Figure 86A:
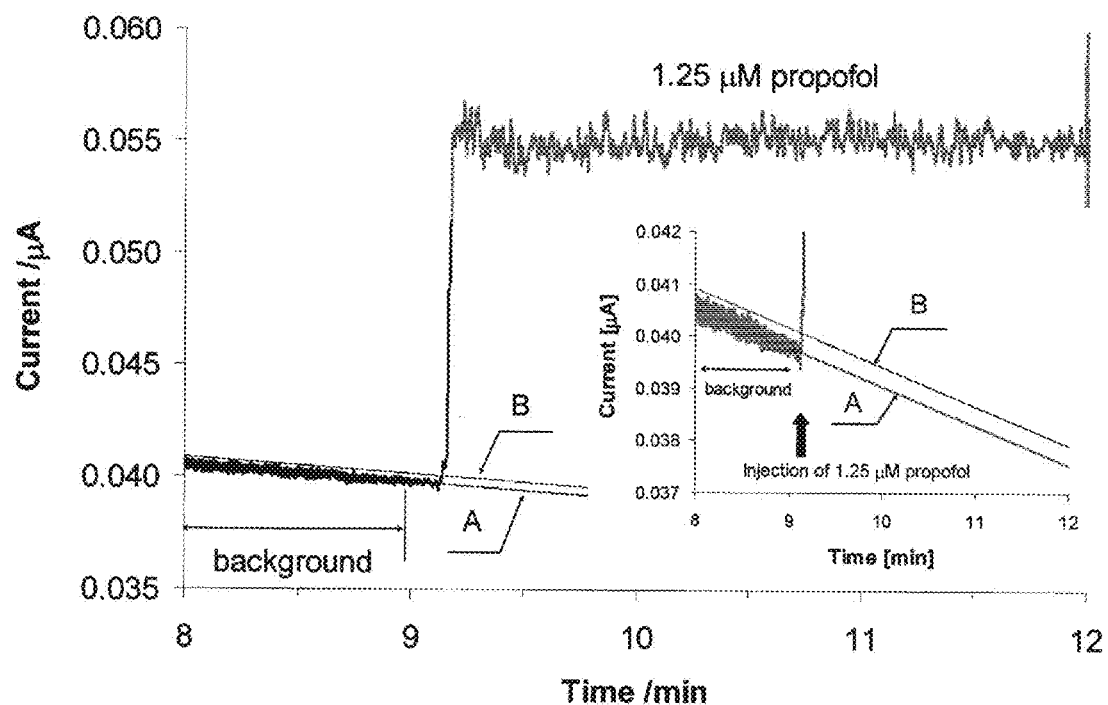
Figure 86B:
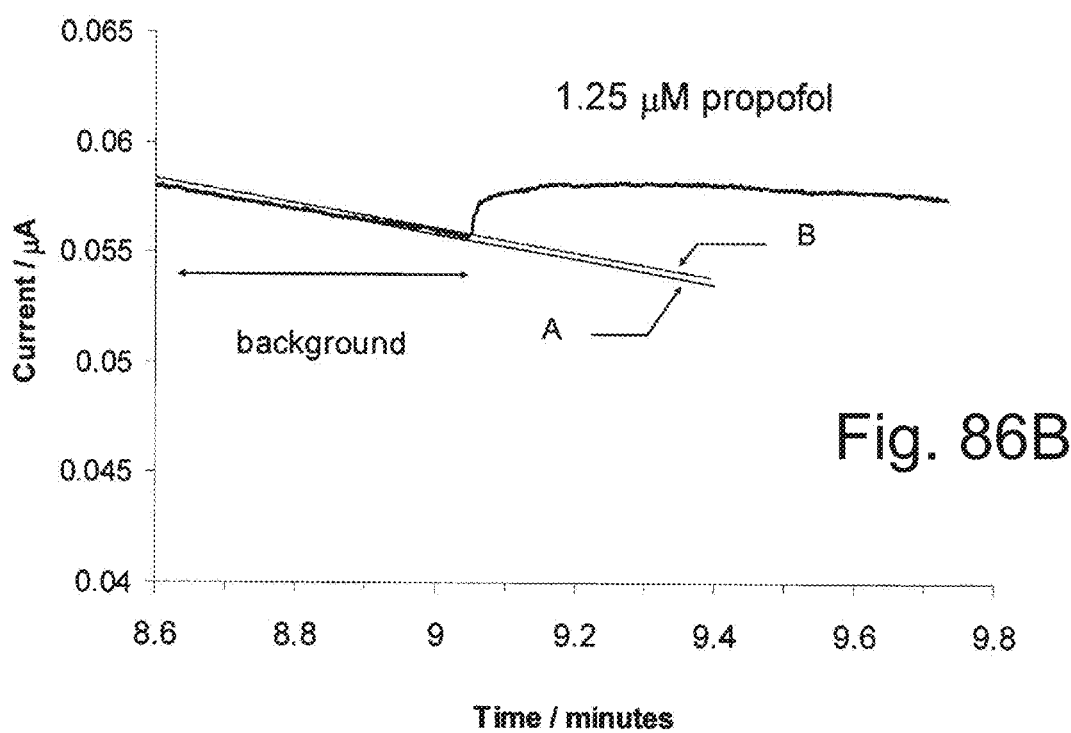

FIG. 86A and FIG. 86B illustrate the CA response of a PVC-membrane coated GC electrode in PBS (FIG. 86A) and in PBS containing 3 mM AA, 1 mM APAP and 5% BSA (FIG. 86B). In both experiments the stirred background solution was spiked with 1.25 $\mu$M of propofol at 9 minutes. In both of FIGS. 86A and 86B, (86A) is a regression line fitted to data points measured in the background one minute before spiking the background with a propofol standard, and (86B) a line with the same slope as line A but shifted parallel to line A by a value of 3 times of the RMSD of the points around line.

It represents a hypothetical average current following a concentration change corresponding to the theoretical detection limit. The inset in FIG. 86A shows a section of the background current on an expanded current scale with lines A and B.

Figure 87A:
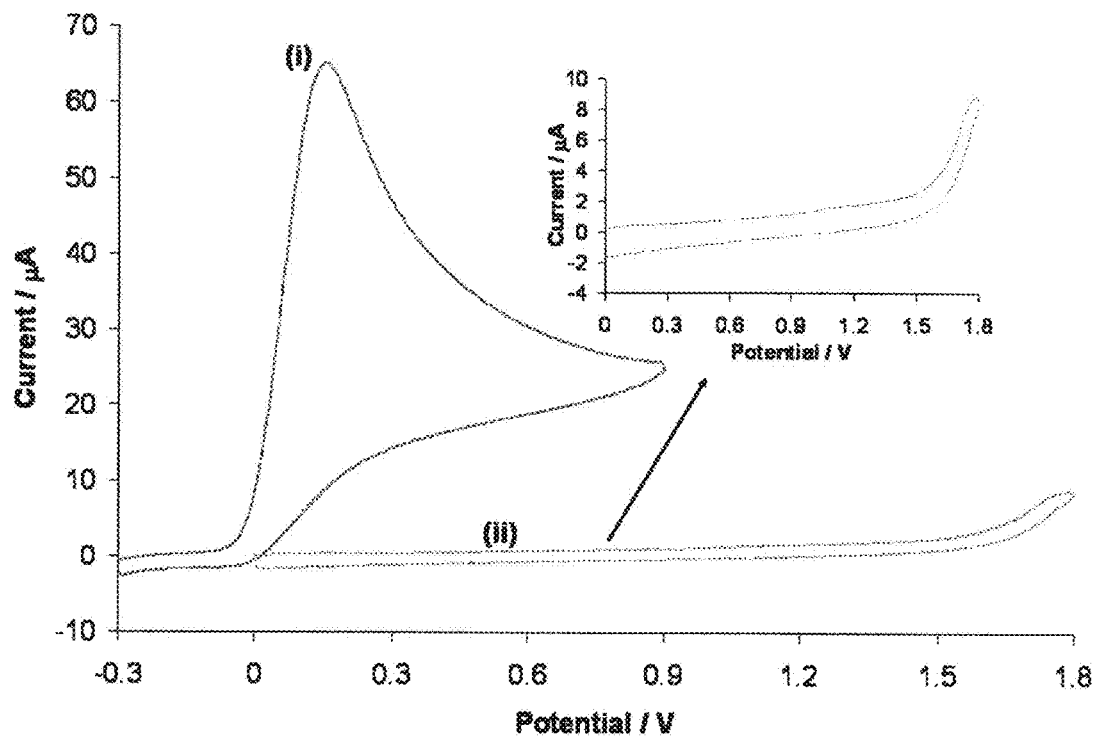

FIG. 87A shows CV scans recorded for 3.0 mM AA in PBS using a (i) bare GC electrode; and (ii) PVC-membrane coated GC electrode. Scan rate, v=0.1 vs-1.

Figure 87B:
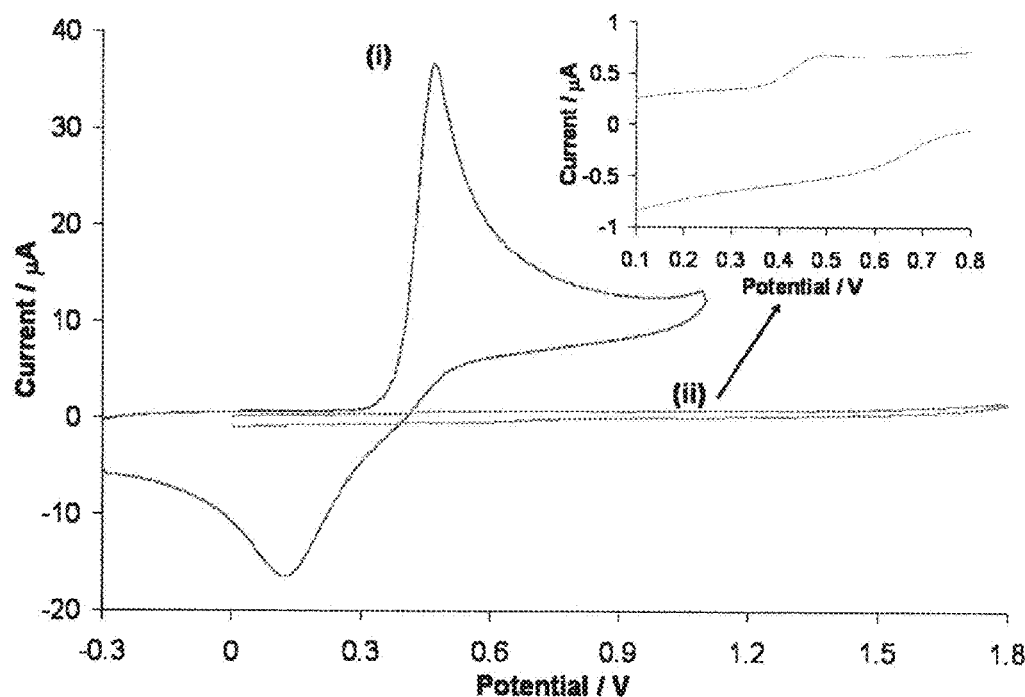

FIG. 87B shows CV scans recorded for 1.0 mM APAP in PBS using a (i) bare GC electrode; and (ii) PVC-membrane coated GC electrode. Scan rate, v=0.1 vs-1

Figure 88:
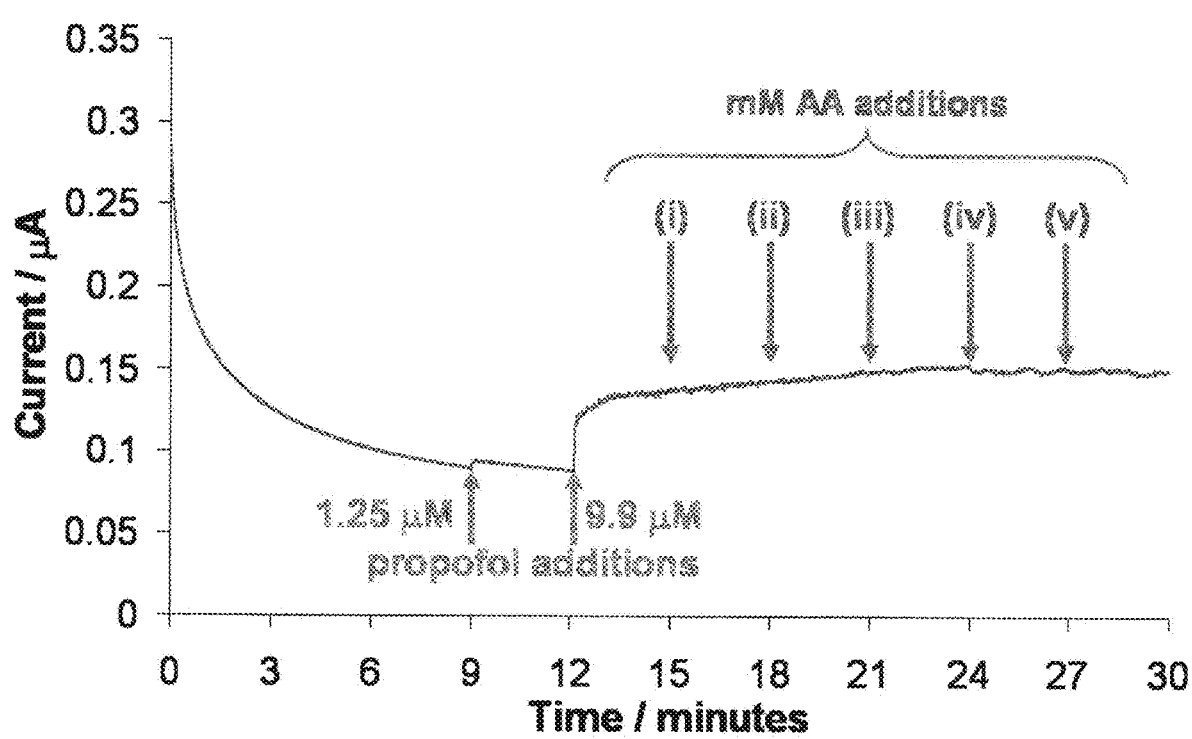

FIG. 88 shows the CA response recorded for 1.25 & 9.9 $\mu$M propofol in a PBS solution containing 5% w/v BSA, followed by additions of (i) 0.53 mM; (ii) 1.0 mM; (iii); 1.48 mM; (iv) 1.98 mM; (v) 3.08 mM AA at 3 minute intervals.

Figure 89:
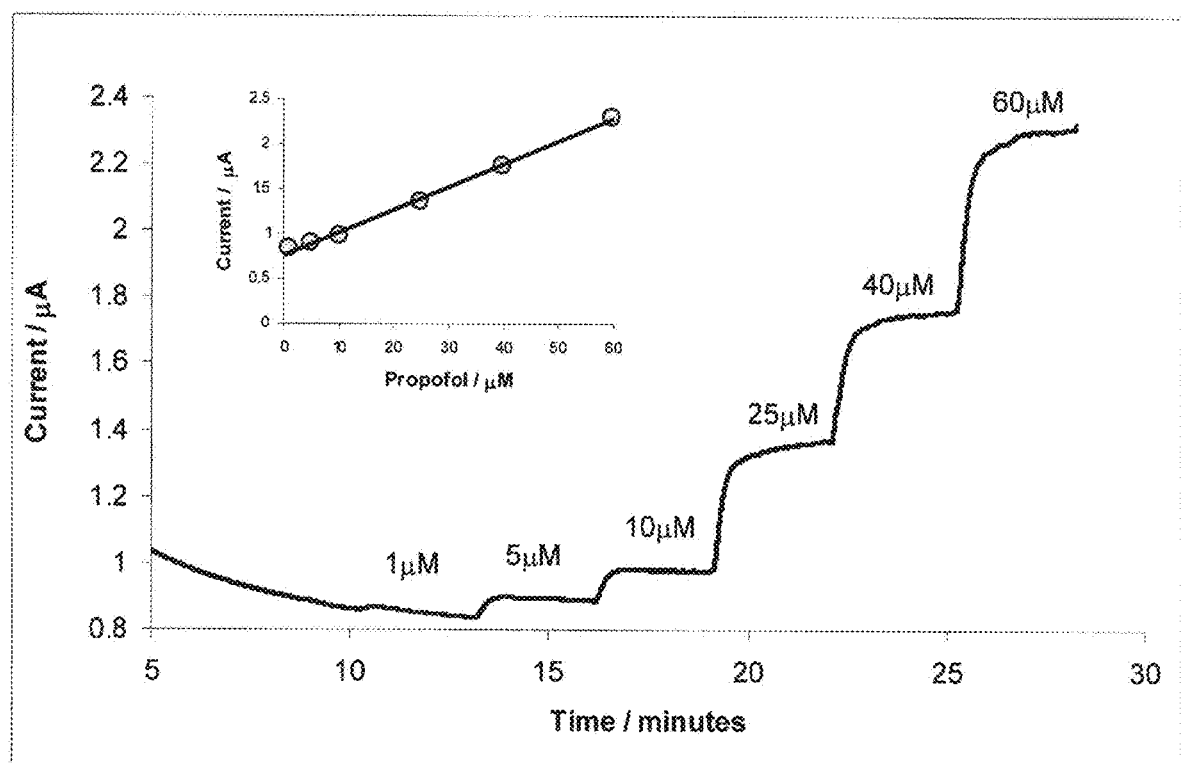

FIG. 89 shows the continuous CA monitoring of propofol. In this experiment propofol solutions with concentrations between 1 $\mu$M and 60 $\mu$M were pumped at constant flow rate through an electrochemical cell in which the working electrode was covered with the organic membrane film. Inset: A calibration curve constructed from the steady state currents measured at different concentrations of propofol.

Figure 90:
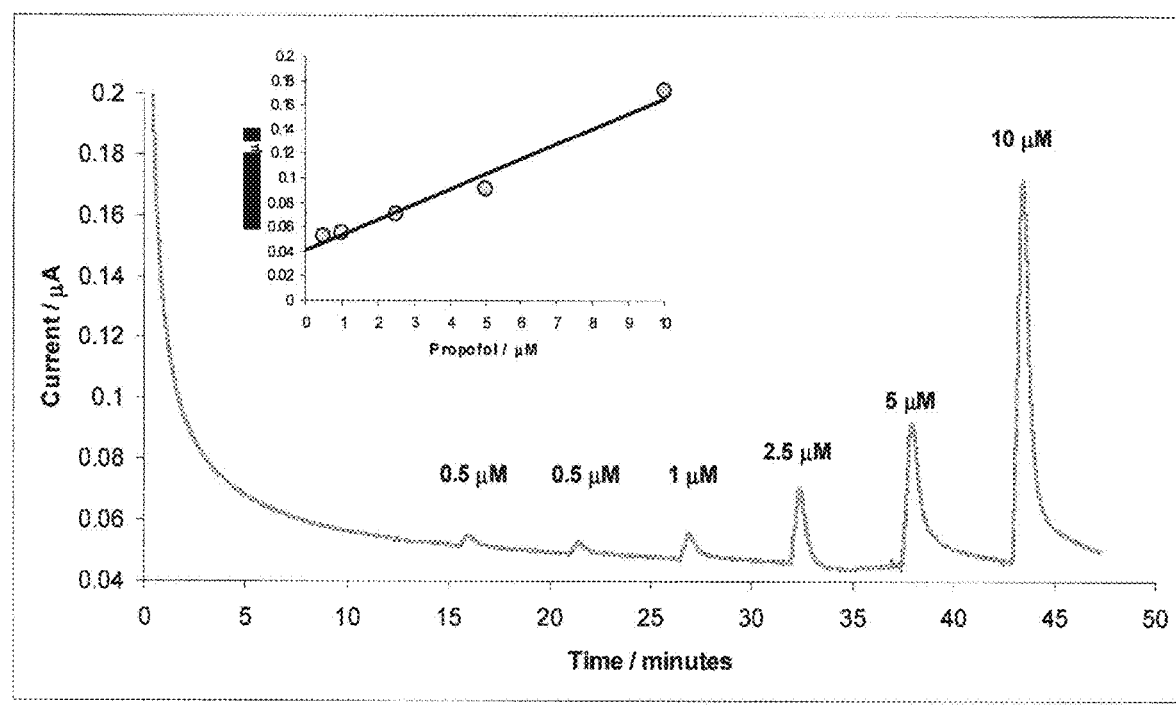

FIG. 90 illustrates the CA flow injection analysis of propofol solutions between 0.5 µM and 10 µM concentrations. In this experiment 100 µL samples of propofol solutions, with concentrations ranging between 0.5 µM and 10 µM, were injected into a continuously flowing carrier solution (PBS). As the injected sample plug passed the flow-through detector cell with the membrane coated propofol a transient signal is recorded. The peak height of these transients is directly proportional to the propofol concentrations in the injected samples. Inset: A calibration curve constructed from the peak heights as a function of the concentration of the injected samples.

Figure 91:
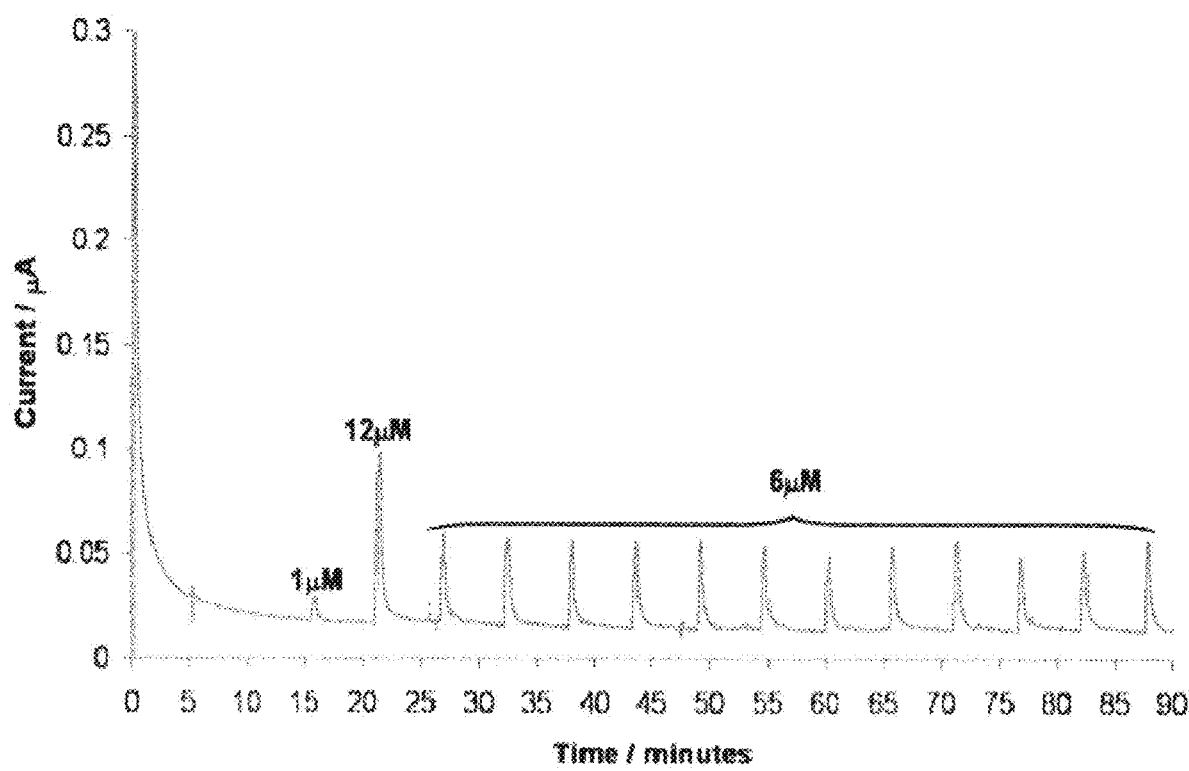

FIG. 91 illustrates the CA flow injection analysis of propofol solutions. Experimental conditions: Sample volume, 175 µL; Flow rate, 0.53 mL/min; applied potential, 1.2 V. 1 µM and 10 µM injections were used to construct a two-point calibration curve. Once the calibration was finished, the monitoring experiment started using 1 2× injections of 6 µM propofol in 5% BSA to simulate what is expected to be achievable using TCI. Injections into the carrier stream were performed at 5 minute intervals to determine the reproducibility of the propofol sensor when it is used in an automated analyzer in flow injection mode. The relative standard deviation was 15%.

Figure 92:
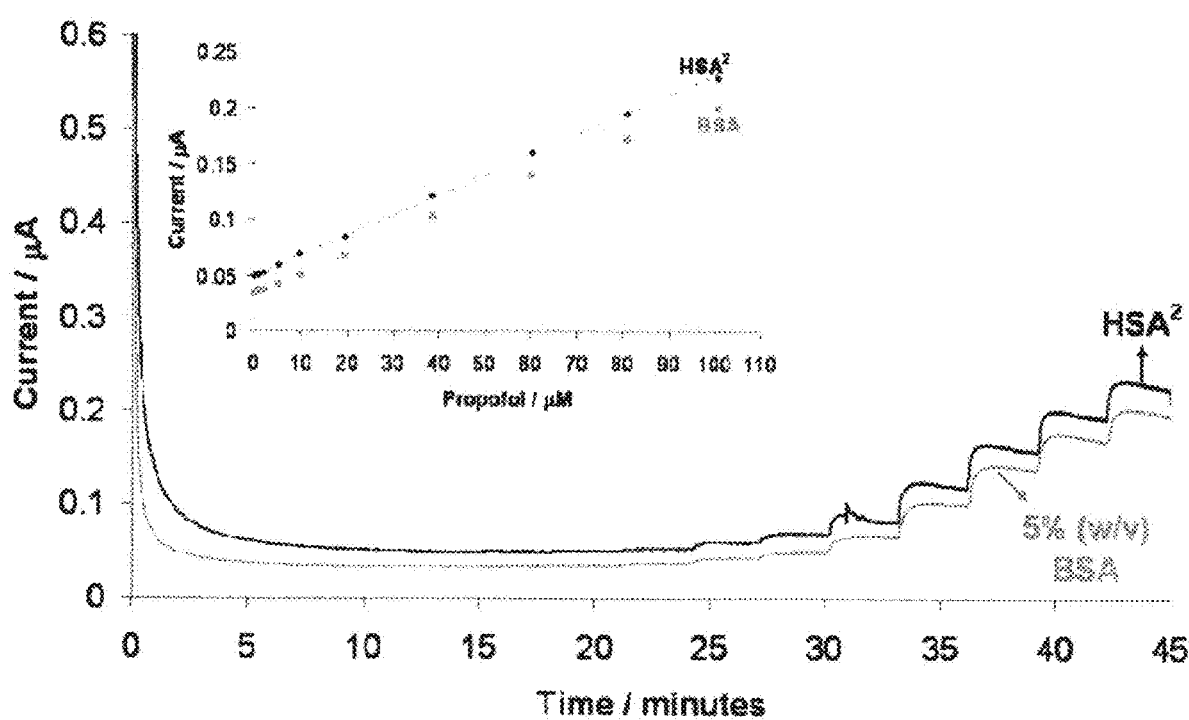

FIG. 92 illustrates continuous CA monitoring of propofol using human serum albumin (HSA) or 5% BSA containing electrolyte solution (simulating serum) with different concentrations of propofol pumped through the electrochemical flow cell. FIG. 92 confirms that the 5% BSA containing standards can be used to assess the concentration in human serum samples.

DETAILED DESCRIPTION OF THE INVENTION

The present invention relates to electrochemical sensors for the detection of bioavailable drug concentration, and devices and methods that include or utilize the electrochemical sensors for real-time control over the delivery of a drug based on the bioavailable drug concentration. In embodiments, delivery of a drug is adjusted, if necessary, in real time following a sensing event.

As used herein, the term "real-time" is intended to mean a response that it carried out within less than a minute, preferably less than 20 or 10 seconds, and most preferably within about 1 to about 5 seconds following a detection event.

As used herein, the term "fluid sample" is intended to mean a body fluid sample including, without limitation blood, plasma, cerebrospinal fluid, and other body fluids. The body fluid sample may be diluted with, e.g., buffer or other reagents that facilitate handling. As used herein, the term "vapor sample" is intended to mean a sample containing a non-liquid component and optionally entrained liquid component. A preferred vapor sample is exhaled breath, which may be diluted with additional gas prior to detection or concentrated by removing certain components of the vapor sample. Both fluid samples and vapor samples can be used to detect the drug or metabolite concentration. As used herein, the term "sample" without further description is intended to encompass both fluid samples and vapor samples.

As used herein, the term "bioavailable drug concentration" is intended to mean the concentration of a drug that exists in a fluid sample, or the drug that exists in a vapor sample, but remains unbound by plasma proteins. Any of a variety of electrochemically active drugs can be monitored in accordance with the present invention, including anesthetics, barbiturates, and sedatives. Exemplary electrochemically active drugs include, without limitation, Propofol, medasolam, methohexitol, atomedate and sufentanol. Exemplary classes of drugs, therapeutic agents, or metabolites include, without limitation, antibiotics, antifungals, antivirals, antihypertensives, antiemetics, narcotics, antimetabolites, anxiolytics, chemotherapeutics, anticoagulants, vitamins, anesthetics, barbiturates, and sedatives. Preferred drugs that are hydrophobic, polar, or amphiphilic, and therefore can be detected in accordance with the present invention include, without limitation, propofol, midazolam, methohexitol, etomidate and sufentanol.

As used herein, the term "total drug concentration" includes the sum of the bioavailable drug concentration and the concentration of drug that is complexed, e.g., bound to plasma proteins. In some embodiments, the bioavailable drug concentration may be the same as or similar to the total drug concentration (i.e., little if any of the drug is bound). In other embodiments, the total drug concentration may be detectable to the extent that the drug is adequately partitioned into the sensor coating of the present invention regardless of its status as bioavailable. Any of a variety of electrochemically active drugs or metabolites can be monitored in accordance with the present invention, particularly drugs, therapeutic agents, or metabolites that are hydrophobic, polar, or amphiphilic. Exemplary classes of drugs, therapeutic agents, or metabolites include, without limitation, antibiotics, antifungals, antivirals, antihypertensives, antiemetics, narcotics, antimetabolites, anxiolytics, chemotherapeutics, anticoagulants, vitamins, anesthetics, barbiturates, and sedatives. Preferred drugs that are hydrophobic, polar, or amphiphilic, and therefore can be detected in accordance with the present invention include, without limitation, propofol, midazolam, methohexitol, etomidate and sufentanol.

By way of example, propofol is a highly lipophilic compound with reported log P values between 3.83 (see Drugs.com Internet site (2012)) and 4.15 (Krasowski et al., J. Pharm. Exp. Therap. 297:338-351 (2001), which is hereby incorporated by reference in its entirety), where P is the octanol/water partition coefficient. The high lipophilicity of propofol offers an opportunity to enhance the voltammetric signal by using an organic-film modified working electrode. Due to its high lipophilicity, the concentration of propofol should be orders of magnitude higher in the film than in the aqueous sample. Other electrochemically active drugs or metabolites having log P values greater than −2.0 can be detected, including those identified above. In certain embodiments, the electrochemically active drugs or metabolites have a log P value that is greater than 2.0.

Accordingly, a first aspect of the present invention relates to an electrochemical sensor or sensor array that can be used to detect bioavailable drug concentration from a fluid or vapor sample.

In an embodiment, the electrochemical sensor includes an electrode and a coating that surrounds the electrode, the coating comprising a structural component, a water immiscible solvent, a resistance decreasing component, and an ion exchange component, wherein the coating selectively partitions an electrochemically active drug from a fluid or vapor sample whereby an electrochemical signal within the coating can be measured using the electrode.

Another embodiment of the electrochemical sensor includes two or more electrodes, and a coating that surrounds the two or more electrodes, where the coating is capable of selectively partitioning an electrochemically active drug directly from the fluid sample such that an oxidation/reduction current within the coating can be measured by the two or more electrodes. The coating also effectively partitions a biocompatible interface between the electrochemical sensor and a sample fluid, and/or prevents electrode fouling (because biological molecules in the fluid sample do not directly contact the electrodes in this embodiment).

By way of example, FIGS. 29A-B illustrate a microelectrode sensor 100 that includes a reference electrode 102, a counter electrode 104 and a working electrode 106, each of which have at least one end surrounded with a coating 108 through which one or more molecules of the bioavailable drug can be partitioned. The electrodes are housed in a glass capillary 110, the end of which has been removed to expose the electrodes. Alternatively, coating 108 may cover or surround more than the tip of reference electrode 102, counter electrode 104 and working electrode 106, for example, the whole of electrochemical sensor 100 could be embedded in the coating material.

In an embodiment, the coating 108 contains a structural component, a water immiscible organic solvent, and a charge transfer component. The coating 108 may optionally contain one or more further additives including, without limitation, a membrane resistance controlling component and a biocompatibility enhancing component.

In another embodiment, the film or coating that covers at least one electrode preferably includes a structural component, water immiscible solvent (or plasticizer), a resistance decreasing component, and an ion exchange component. The coating may optionally contain one or more further additives including, without limitation, adhesion enhancing and biocompatibility enhancing component, as well as any additional agents that inhibit certain biological responses, such as anti-inflammatory agents, anti-coagulants, and the like.

Any suitable structural component can be utilized in the coating 108. The structural component can be polymeric or non-polymeric. Exemplary structural components include, without limitation, polyvinylchloride (PVC), silicone rubber, polyurethane, (meth)acrylate polymer, polypyrrole, polythiophene, polyoctylthiophene, polyanaline, polyvinyl pyrrolidone, agarose, hydrogel, sol-gel materials, and combinations thereof.

In certain embodiments, the structural component can form a relatively minor portion of the coating, and in other embodiments the structural component can form a major portion of the coating.

The structural component is preferably present in an amount of about 5 to about 80 wt. percent of the total coating, more preferably about 15 to about 70 wt. percent of total coating. In certain embodiments, the structural component is present in an amount of about 20 to 30 wt. percent of the total coating. In alternative embodiments, the structural component is present in an amount of about 30 to 50 wt. percent of the total coating. In certain embodiments, the structural component can also serve as working electrode, e.g., porous three dimensional carbon materials.

Any suitable water immiscible organic solvent (or plasticizer) can be utilized in the coating 108. The organic solvent is responsible for assisting in the partitioning of the bioavailable drug from the fluid sample into the coating 108. Exemplary water immiscible organic solvents include, without limitation, 2-nitrophenyl octyl ether (o-NPOE), dioctyl sebacate (DOS), bis(2-ethylhexyl) sebacate, benzyl s-nitrophenyl ether, bis(1-butilpentyl) adipate, bis(2-ethylhexyl) adipate, bis(2-ethylhexyl) phthalate, 1-chloronaphthalene, chloroparaffin, 1-decanol, dibutyl phthalate, dibutil sebacate, dibutyl-dilaurate, dodecyl 2-nitrophenyl ether, and combinations thereof.

In certain embodiments the organic solvent can be a fluorinated liquid, e.g. without limitation perfluorooctane, perfluorononane, perfluoro(2-methyloctane), perfluorodecaline and combinations thereof. In certain embodiments where the structural component forms a minor portion of the coating, then the organic solvent can form a relatively major portion of the coating; and in other embodiments where the structural component form a major portion of the coating, then the organic solvent can form a relatively minor portion of the coating.

The organic solvent is preferably present in an amount of about 5 to about 85 wt. percent of the total coating, more preferably about 10 to about 70 wt. percent of total coating. In certain embodiments, the organic solvent is present in an amount of about 45 to about 55 wt. percent of the total coating. In one alternative embodiment, the structural component is present in an amount of about 30 to 45 wt. percent of the total coating. In another alternative embodiment, the structural component is present in an amount of about 55 to about 70 wt. percent of the total coating.

The resistance decreasing component is an organic salt that is not soluble in water and includes both a lipophilic cation and a lipophilic anion. As used herein, an organic salt that is not soluble is one that is characterized by a log P value (indeed the logarithm of the membrane water partition coefficient) that is larger than 6.1 or log D value (membrane distribution coefficient) that is larger than 6.1 at the sample solution pH at which the analysis is performed. Considered in terms of the amount of organic salt lost from the membrane to an aqueous sample solution, for two hours of monitoring the amount of organic salt lost from the membrane is about 1% of the starting amount.

The lipophilic cation is preferably an ammonium cation or phosphonium cation, more preferably a quaternary ammonium cation or a tetraarylphosphonium cation. The quaternary ammonium cations are preferably tetraalkylammonium cations where the alkyl groups are independently 1 to 48, preferably 4 to 24, carbon atoms.

Exemplary lipophilic cations include, without limitation, tetradodecylammonium, tetraphenylphosphonium, bis(triphenylphosphoranylidine) ammonium, dimethyldioctadecyl ammonium, hexadecyltrioctadecylammonium, methyltrioctadecylammonium, tetrahexadecylammonium, tetraoctadecylammonium, tetraoctylammonium, tridodecylmethylammonium, tris[(perfluorooctyl)propyl]ammonium, and combinations thereof.

The lipophilic anion is preferably a borate, sulfonate, or a carborane, including halogenated or nonhalogenated carboranes. Of these, borates and sulfonates are preferred.

Exemplary lipophilic anions include, without limitation, tetraphenylborate, tetrakis(pentafluorophenyl) borate, tetrakis(4-chlorophenyl) borate, tetrakis [3,5,bis(trifluoromethyl) phenyl] borate, tetrakis(4-fluorophenyl) borate, dinonylnaphthalene sulphonate, tetrakis [3,5-bis(perfluorohexyl) phenyl]borate, tetrakis(p-tolyl)borate, tetrakis(m-tolyl)borate, tetrakis(2,4-dimethyl)borate, tetrakis(3,5-dimethylphenyl)borate, closo-dodecacarborane, undecachlorinated carborane (UCC), hexabrominated carborane (HBC), undecaiodinated carborane (UIC), undecabromocarborane, and combinations thereof.

Thus, exemplary water insoluble organic salts of the invention include, without limitation: tetradodecylammonium tetrakis(pentafluorophenyl) borate (TDDATPFPhB), bis(triphenylphosphoranylidene)ammonium tetrakis[3,5bis(trifluoromethyl)phenyl]borate (BTPPATFPhB), tetradodecylammonium tetrakis(4-chlorophenyl)borate, tris[(perfluorooctyl)propyl]ammonium tetrakis [3,5-bis(perfluorohexyl)phenyl]borate, tetraheptylammonium tetraphenylborate, tetradodecylammonium dinonylnaphthalene sulphonate, tetraphenylphosphonium tetraphenylborate, tetraphenylphosphonium tetrakis(pentafluorophenyl)borate, tetraphenylphosphonium tetra-p-tolylborate, tetraphenylphosphonium tetra-m-tolylborate, bis(triphenylphosphoranylidene)ammonium tetraphenylborate, bis(triphenylphosphoranylidene)ammonium tetrakis(pentafluorophenyl)borate, bis(triphenylphosphoranylidene)ammonium tetrakis(4-chlorophenyl)borate, bis(triphenylphosphoranylidene)ammonium tetrakis[3,5bis(trifluoromethyl)phenyl]borate, bis(triphenylphosphoranylidene)ammonium tetrakis(4-fluorophenyl)borate, hexadecyltrioctadecylammonium tetraphenylborate, tetraoctadecylammonium tetraphenylborate, tetraoctadecylammonium tetrakis(4-chlorophenyl)borate, tetraoctadecylammonium tetraphenylborate, tetraoctadecylammonium tetrakis(4-chlorophenyl)borate, tetraoctadecylammonium tetrakis(4-fluorophenyl)borate, tetraoctylammonium tetraphenylborate, tetraoctylammonium tetrakis(pentafluorophenyl)borate, tetraoctylammonium tetrakis(4-chlorophenyl)borate, tetraoctylammonium tetrakis[3,5,bis(trifluoromethyl)phenyl]borate, tetraoctylammonium tetrakis(4-fluorophenyl)borate, tridodecylmethylammonium tetraphenylborate, tridodecylmethylammonium tetrakis(pentafluorophenyl)borate, tridodecylmethylammonium tetrakis(4-chlorophenyl)borate, tridodecylmethylammonium tetrakis [3,5,bis(trifluoromethyl)phenyl]borate, tridodecylmethylammonium tetrakis(4-fluorophenyl)borate, tridodecylmethylammonium dinonylnaphthalene sulphonate, dodecyltrimethylammonium dinonylnaphthalene sulphonate, tetrabutylammonium tetraphenylborate, tetrabutylammonium tetrakis(pentafluorophenyl)borate, tetrabutylammonium tetrakis(4-chlorophenyl)borate, tetrabutylammonium tetrakis(4-fluorophenyl)borate, tetrabutylammonium tetrakis [3,5,bis(trifluoromethyl)phenyl]borate, tetraphenylphosphonium tetraphenylborate, trimethylammonium undecabromocarborane (TMAUBC), and combinations thereof.

The resistance decreasing component is preferably present in an amount of about 1 to about 30 wt. percent of the total coating, more preferably about 5 to about 25 wt. percent of the total coating. In certain embodiments, the resistance decreasing component is present in an amount of about 5 to 10 wt. percent of the total coating. In alternative embodiments, the resistance decreasing component is present in an amount of about 10 to 20 wt. percent of the total coating. In a further embodiment, the resistance decreasing component is present in an amount of about 20 to about 25 wt. percent of the total coating.

The ion exchange component is either (i) a cation exchanger that includes a hydrophilic cation and a lipophilic anion, or (ii) an anion exchanger that includes a lipophilic cation and a hydrophilic anion.

The hydrophilic cation of the cation exchanger can be any water soluble cation. Exemplary hydrophilic cations include, without limitation, those selected from the group of alkali metal (e.g., lithium, sodium, potassium) cations, alkaline earth metal (e.g., magnesium, calcium) cations, transition metal (e.g., manganese, iron, zinc) cations, and complex (e.g., ammonium) cations.

The lipophilic anion of the cation exchanger can be any of the water insoluble borates, sulfonates, and halogenated and nonhalogenated carboranes as identified above for the resistance decreasing component.

Exemplary cation exchangers include, without limitation, sodium or potassium tetrakis[3,5bis(trifluoromethyl) phenyl] borate (NaTFPhB or KTFPhB), sodium or potassium tetrakis[pentafluorophenyl] borate (NaTPFPhB or KTPFPhB), sodium or potassium tetrakis(4-chlorophenyl) borate (NaTpClPhB or KTpClPhB), sodium or potassium tetraphenylborate, sodium or potassium tetrakis(4-fluorophenyl)borate, sodium or potassium tetrakis(p-tolyl)borate, sodium or potassium tetrakis(m-tolyl)borate, sodium or potassium tetrakis(2,4-dimethyl)borate, sodium or potassium tetrakis(3,5-dimethylphenyl)borate, sodium or potassium tetrakis[3,5-bis(1,1,1,3,3,3-hexafluoro-2-methoxy-2-propyl)phenyl]borate, sodium or potassium tetrakis[3,5-bis(perfluorohexyl)phenyl]borate, sodium or potassium tetrakis [3,5bis(trifluoromethyl) phenyl] aluminate, sodium or potassium tetrakis [pentafluorophenyl] aluminate, sodium or potassium tetrakis(4-chlorophenyl) aluminate, sodium or potassium tetraphenylaluminate, sodium or potassium tetrakis(4-fluorophenyl) aluminate, sodium or potassium tetrakis (p-tolyl) aluminate, sodium or potassium tetrakis(m-tolyl) aluminate, sodium or potassium tetrakis(2,4-dimethyl) aluminate, sodium or potassium tetrakis(3,5-dimethylphenyl) aluminate, and combinations thereof.

The lipophilic cation of the anion exchanger can be any of the water insoluble cations identified above for the for the resistance decreasing component, preferably the quaternary ammonium cations, bis(triphenylphosphoranylidene) ammonium cations, tris[(perfluorooctyl)propyl]ammonium cations, and tetraarylphosphonium cations identified above.

The hydrophilic anion of the anion exchanger can be any water soluble anion.

Exemplary anions include, without limitation, those selected from the group of halides (e.g., $F^-$, $Cl^-$, $Br^-$, $I^-$), $NO_3^-$, $SO_4^{2-}$, $SO_3^{2-}$, $HSO_3^-$, $HCO_3^-$ $HPO_4^{2-}$, $H_2PO_4^-$, and $ClO_4^-$.

Exemplary anion exchangers include, without limitation, a quaternary ammonium chlorides, bromides, or perchlorates, and bis(triphenylphosphoranylidene) ammonium chlorides or bromides. The ion exchange component is preferably present in an amount of about 0.001 to about 30 wt. percent of the total coating, more preferably about 0.5 to about 25 wt. percent of total coating, more preferably about 0.5 to about 5 wt. percent. In certain embodiments, the ion exchange component is present in an amount of about 0.5 to 10 wt. percent of the total coating. In alternative embodiments, the ion exchange component is present in an amount of about 10 to 20 wt. percent of the total coating. In a further embodiment, the ion exchange component is present in an amount of about 20 to about 30 wt. percent of the total coating.

In certain embodiments of the present invention, the coating includes about 5 to about 80 wt. percent of the structural component, about 5 to about 85 wt. percent of the water immiscible solvent, about 5 to about 30 wt. percent of the resistance decreasing component, and about 0.001 to about 30 wt. percent of the ion exchange component.

In another embodiment of the present invention, the coating includes about 15 to about 70 wt. percent of the structural component, about 10 to about 70 wt. percent of the water immiscible solvent, about 5 to about 30 wt. percent of the resistance decreasing component, and about 0.5 to about 5 wt. percent of the ion exchange component.

In certain exemplary embodiments, the coating includes about 20 to 30 wt. percent of PVC as the structural component; about 45 to 55 wt. percent of o-NPOE, DOS, or 1-octanol as the water immiscible solvent; about 20 to 25 wt. percent of TDDATPFPhB or BTPPATFPhB as the resistance decreasing component; and about 2 to about 4 wt. percent of NaTFPhB or KTPFPhB as the ion exchanger component.

Any suitable adhesion enhancing component can be utilized in the coating, when desired for preventing the formation of an aqueous layer between the coating and the working electrode surface or between the coating and the planar electrochemical cell surface.

Any suitable charge transfer agent can be utilized in the coating 108. Exemplary charge transfer components include, without limitation, tetradecylammonium tetrakis(pentofluorophenyl)borate (TDATPFPB), tetrahexylammonium perchlorate, and combinations thereof.

Any suitable membrane resistance controlling agent can be utilized in the coating 108, when desired. Exemplary membrane resistance controlling agents include, without limitation, lipophilic electrolytes, tetradodecyl ammonium-tetrakis(4-chlorophenyl) borate (ETH500), bis(triphenylphoranylidene) ammonium tetrakis[3,5-bis(trifluoromethyl)phenyl] borate (BTPPATFPB), and combinations thereof.

Any suitable biocompatibility enhancing component can be utilized in the coating 108, when desired. Exemplary biocompatibility enhancing components include, without limitation, nitric-oxide releasing sol-gel materials, N-(6-aminohexyl)aminopropyltrimethoxysilane, balanced isobutyltrimethoxysilane diazeniumdiolate, and combinations thereof. These can be used in amounts up to about 5 wt. percent, preferably between about 0.001 to about 3 wt. percent.

Any suitable anti-inflammatory agents can be utilized in the coating, when desired. These can be used in amounts up to about 5 wt. percent, preferably between about 0.001 to about 3 wt. percent. These agents should not interfere with the electrochemical signal caused by partitioning of the drug into the coating.

Any suitable anti-coagulant agents can be utilized in the coating, when desired. These can be used in amounts up to about 5 wt. percent, preferably between about 0.001 to about 3 wt. percent. These agents should not interfere with the electrochemical signal caused by partitioning of the drug into the coating.

According to one preferred embodiment, the coating 108 is formed from a composition including about 15 to about 67 wt percent PVC, about 33 to about 85 wt percent o-NPOE, and about 0.001 to about 15 wt percent TDATPFPB.

Coating 108 can be of a suitable dimension that affords effective partitioning while allowing for sufficient electrochemical signaling and/or oxidation/reduction current within coating 108. For example, and not by limitation, coating 108 is less than about 200 μm thick, more preferably less than about 100 μm thick. According to one embodiment, coating 108 has a sub-micron thickness. According to another embodiment, coating 108 is between about 1 to about 25 μm thick. According to another embodiment, the coating has a sub-micron thickness.

The sensor design and the electrochemical signal that is detected by the sensor can be according to any of a variety of known sensor formats, including without limitation a chronoamperometric sensor (measuring current as the function of time as the signal), voltammetric sensor (measuring current as the function of the applied voltage as a signal), a potentiometric sensor (measuring the phase boundary potential as the signal), a conductometric sensor (measuring resistance or conductance as the signal), or a coulometric sensor (measuring charge as the signal).

The minimum number of electrodes used for each of these sensor designs is well known in the art. A voltammetric sensor can include, without limitation, one or more working electrodes in combination with a reference electrode, or one or more working electrodes in combination with a reference electrode and a counter electrode. In voltammetry, different potential programs can be applied to the working electrode, e.g., the potential can be varied over time (linear sweep voltammetry or cyclic voltammetry), potential can also be constant (chronoamperometry) or applied as pulses with the same or changing amplitude (pulse voltammetric methods) to measure the current related to the analyte concentration with the membrane coated sensor. A chronoamperometric sensor typically utilizes one or more working electrodes in combination with a reference electrode and a counter electrode, and the potential applied to the working electrode is constant or is applied as sho11 pulses to measure the current related to the oxidation or reduction of the analyte with the membrane coated sensor. Chronoamperometry typically yields a better signal to noise ratio in comparison to other amperometric techniques. A conductometric sensor can include two or four electrodes, which measure the impedance of the coating with the sample solution. A potentiometric cell can include two electrodes, in which the potential of the indicator electrode is measured at zero current. A coulometric sensor can include two or more electrodes and measures the charge related to the oxidation or reduction of the analyte in the membrane coating. The design and principles surrounding these types of electrochemical sensors are described in Bard and Falkner, Electrochemical Methods, John Wiley and Sons, New York (2001); and Toth et al., "Electrochemical Detection in liquid Flow Analytical Techniques: Characterization and Classification," Pure Appl. Chem. 76(6): 1119-1138 (2004), each of which is hereby incorporated by reference in its entirety.

Reference electrode 102, counter electrode 104 and working electrode 106 can be formed out of a suitable conductive material including, without limitation, carbon, silver, mercury, gold, platinum, palladium, ruthenium, rhodium or combinations thereof. Although only three microelectrodes—reference electrode 102, counter electrode 104 and working electrode 106 are described with respect to FIG. 29B, according to certain embodiments four electrodes can be present. Further, various aspects of the invention are not limited by specific arrangement and structure of reference electrode 102, counter electrode 104 and working electrode 106 shown in FIG. 29B, and one skilled in the art after reading this disclosure may devise other arrangements and structures. The particular function and number of electrodes will depend upon the type of electrochemical sensor that is employed, and aspects of the present invention are not limited by specific formation(s) of the electrochemical sensor illustrated herein. At least the working electrode is covered by the coating. Exemplary electrode functions include, working electrode, auxiliary or counter electrode, and reference electrode. The particular function and number of electrodes will depend upon the type of electrochemical sensor 100 that is employed, and aspects of the present invention are not limited by specific formation(s) of electrochemical sensor 100.

Exemplary sensor formats include, without limitation, voltammetric sensors, potentiometric sensors, conductometric sensors, and coulometric sensors. A voltammetric sensor can include, without limitation, one or more working electrodes in combination with a reference electrode, or one or more working electrodes in combination with a reference electrode and a counter electrode. In voltammetry, the potential applied to the working electrode is varied over time to measure the current through either the coating (i.e., for the coated sensor embodiment) or in the fluid sample (i.e., for the uncoated sensor array embodiment). A conductometric sensor can include two or four electrodes, which measure the impedance of either the coating or the fluid sample. A potentiometric cell can include two electrodes, in which the potential of the indicator electrode is measured at zero current. A coulometric sensor can include two or more electrodes. The design and principles surrounding these types of electrochemical sensors are described in Toth et al., "Electrochemical Detection in liquid Flow Analytical Techniques: Characterization and Classification," *Pure Appl. Chem.* 76(6):1119-1138 (2004), which is hereby incorporated by reference in its entirety.

Application of the coating over the electrode can be carried out by first forming a mixture of the component ingredients, which are dissolved in a suitable solvent such as THF, and then applying the dissolved solution using any of a variety of means including, without limitation, spray-coating, spin-coating, dip-coating, roller-coating, blade-coating, etc. The particular choice of coating technique will depend on its compatibility with the structure of the electrochemical cell that forms part of the sensing device of the present invention. During and subsequent to application the solvent used to disperse the components is removed, leaving the coating applied to a surface of the electrode(s).

By way of example, one embodiment of the electrochemical sensor is illustrated in FIG. 78. In this figure, a macroelectrode 300 encapsulated in glass matrix 306 is shown with the surface of the single, embedded carbon or metal disc-shaped working electrode (WE) 302 embedded in the coating 310. In the enlarged portion of this figure, the WE surface and coating are schematically illustrated. The graphite or metal working electrode (WE) material embedded in an insulator matrix. The coating components include: A, chemical representation of PVC, which is an example of the structural component of the membrane; B, chemical representation of 2-nitrophenyl octyl ether, the water immiscible organic solvent of the membrane; C, chemical representation of the ion exchange component potassium tetrakis [3,5,bis (trifluoromethyl) phenyl] borate; and D, chemical representation of the resistance controlling component tetradodecylammonium tetrakis(pentafluorophenyl) borate.

Three dimensional representations of a single macroelectrodes where the one or more electrodes (e.g., carbon, gold, or platinum) is incorporated into an insulating matrix, e.g., glass, and the surface of the electrode or the surface of the entire electrochemical cell is coated with a film or coating that is capable of partitioning the bioavailable drug from the sample are shown in FIG. 76 and FIG. 77. In FIG. 76, macroelectrode 100 contains a single electrode 102 encapsulated by glass matrix 106, and the surface of the electrode is shown embedded in the film or coating 110. In FIG. 77, electrochemical cell 200 containing three electrodes (working, 202; counter, 203; and reference, 204; electrodes) encapsulated by glass matrix 206, and the surfaces of the electrodes are shown embedded in the film or coating 210.

As demonstrated in the accompanying examples, electrochemical sensors of the present invention are capable of detecting propofol levels in a fluid sample which are well below the therapeutic target steady state concentration for blood/serum levels thereof. In particular, the lower limit of detection for propofol is shown to be at submicromolar concentrations, which is about 1-2 orders of magnitude below the therapeutic range for this drug.

Another preferred embodiment of the electrochemical sensor includes two or more electrodes in an electrode array. One form of construction includes a plurality of working electrodes, which are used in series such that each working electrode is used, preferably, only one or twice, more preferably only once. This has the benefit of providing a new working electrode during each sensing process, and therefore biofouling of a working electrode (via proteins and other biomolecules in the fluid sample) is immaterial. The sensor according to this embodiment may include one or both of an auxiliary or counter electrode, and a reference electrode. An exemplary construction of this embodiment is illustrated in FIG. 40, and its use is described in herein, such as in Example 3 infra.

Another form of construction includes a plurality of sensor arrays, where each array includes the two or more electrodes required for the sensing format of choice, e.g., one or more working electrodes in combination with a reference electrode and a counter electrode for voltammetry. FIG. 40 illustrates a microfluidic device 200 that includes a microfluidic channel 202 and a plurality of carbon nanofiber sensors 204 in array within the channel 202. One or more sensor arrays can be provided in each of a plurality of microfluidic channels.

Carbon nanofibers are compatible with a large number of microfabrication techniques including lithographic processing, material lift-off techniques, wet and dry etching, and chemical/mechanical polishing. As such, standard microfabrication techniques may be employed to incorporate into functional nanoscale electroanalytical platforms. Single CNFs can be synthesized on electrical interconnects and implemented as electrochemical electrodes with individual addressability down to ~1-2 micron interfiber spacing (Arumugam et al., "Wafer-scale fabrication of patterned carbon nanofiber nanoelectrode arrays: A route for development of multiplexed, ultrasensitive disposable biosensors," *Biosensors Bioelectronics* 24(9): 2818-2824 (2009); Melechko et al., "Vertically aligned carbon nanofibers and related structures: Controlled synthesis and directed assembly," *J. Appl. Phys.* 97(4):041301 (2005), each of which is hereby incorporated by reference in its entirety). Alternatively, the carbon nanofiber array can be prepared on a flexible substrate and then introduced to the interconnect (Fletcher et al., "Transfer of Flexible Arrays of Vertically Aligned Carbon Nanofiber Electrodes to Temperature-Sensitive Substrates," *Adv. Mat.* 18(13):1689-1694 (2006), which is hereby incorporated by reference in its entirety). Moreover, fabrication techniques allow only the nanoscale tip of these fibers to be electrochemically active (Huang et al., "Microelectrode Arrays for Electrochemistry: Approaches to Fabrication," *Small* 5(7):776-788 (2009); Potje-Kamloth et al., "Electrochemically Prepared Insulation for Carbon Fiber Microelectrodes," *Berichte der Bunsengesellschaft für Physikalische Chemie* 93(12):1480-1485 (1989), each of which is hereby incorporated by reference in its entirety). Thus, the nanofiber serves both to elevate the electroanalytical measurement volume above the planar substrate and to electrically bridge between the nanoscale dimensions of the fiber tip and the microscale dimensions of the electrical interconnects of the substrate. The electroactive tips of these vertically-oriented devices enable electroanalytical probing of extremely small volumes (<500 zeptoliter). This enables both the quantification of electroactive species as well as the direct manipulation of the local environment (oxidation, reduction, pH variation, field application, thermal modulation). These CNF probes can also be integrated with an active matrix thin film transistor array to significantly improve functionality and significantly increase the number of electrochemically active probes (400 probes in a 20×20 array, 1 mm$^2$ footprint). This adds significant parallelism, offering high device density, large dynamic driving range, high temporal and electrophysiological signal sensitivity, and simpler driving electronics.

As illustrated in FIG. 40, the electrical circuitry can be formed on the SiO$_2$ substrate of a bulk silicon wafer using standard procedures. Thereafter, the carbon nanofiber array can be prepared such that each nanofiber is in electrical contact with the appropriate interconnect (see, e.g., Arumugam et al., "Wafer-scale fabrication of patterned carbon nanofiber nanoelectrode arrays: A route for development of multiplexed, ultrasensitive disposable biosensors," *Biosensors Bioelectronics* 24(9): 2818-2824 (2009); Melechko et al., "Vertically aligned carbon nanofibers and related structures: Controlled synthesis and directed assembly," *J. Appl. Phys.* 97(4):041301 (2005), each of which is hereby incorporated by reference in its entirety). Thereafter, SU-8 photoresist can be applied to the SiO$_2$ surface and the surface of the carbon nanofibers (with the exception of the very tip of each nanofiber) (Huang et al., "Microelectrode Arrays for Electrochemistry: Approaches to Fabrication," *Small* 5(7): 776-788 (2009); Potje-Kamloth et al., "Electrochemically Prepared Insulation for Carbon Fiber Microelectrodes," *Berichte der Bunsengesellschaft für Physikalische Chemie* 93 (12): 1480-1485 (1989), each of which is hereby incorporated by reference in its entirety). Finally, SU-8 material in bulk can be adhered to the applied SU-8 coating to form the microfluidic channel.

A further embodiment is a microfluidic sensor array that does not contain carbon nanofibers. This array includes (i) the one or more electrodes in communication with a microfluidic channel through which the fluid sample passes during the detection procedure. The one or more electrodes in each array can optionally be coated with the coating 108 described above in connection with sensor 100 (FIG. 29B). Regardless, the coated electrodes are positioned with their coating in communication with the microfluidic channel through which the fluid sample passes during the detection procedure.

In one embodiment, illustrated in FIG. 37, a microfluidic biosensor 300 is formed using a polyimide insulation 302 and three microelectrochemical grid array sensors 304 in series in a microfluidic channel 306 formed in a polydimethylsiloxane ("PDMS") block 308. Each array includes a reference electrode, counter electrode, and working electrode. The working electrodes are formed as microdisc arrays with 5 micron diameter gold discs positioned 50 μm center-to-center in a hexagonal arrangement. The channel 306 is provided with an inlet and outlet for moving the sample through the microchannel and across the sensor array.

In another embodiment, illustrated in FIG. 38, a microfluidic biosensor 400 with polyimide insulation 402 utilizes individually addressable gold microband arrays (only the electrode at the center of 404) as working electrodes. The widths of the individual bands are between 2 and 10 microns. A complete biosensor 404 includes the microband array working electrode, reference electrode, and counter electrode in a microfluidic channel 406 formed in a PDMS block 408. The working electrodes. is in the form of 5 μm wide individually addressable bands that are spaced 100 μm center-to-center. The sensors can optionally be interconnected with a single lead wire. The channel is provided with an inlet and outlet for moving the sample through the microchannel and across the sensor array.

In a further embodiment, illustrated in FIG. 39, a microfluidic biosensor 500 is formed with polyimide insulation 502 and three interdigitated array 504 electrochemical sensors in series in a microfluidic channel 506 formed in a PDMS block 508. Each array includes a reference electrode, counter electrode, and working electrode. The working electrode is in the form of an interdigitated electrode array that includes 5 μm wide fingers and 5 μm wide gaps between the fingers. The channel is provided with an inlet and outlet for moving the sample through the microchannel and across the sensor array.

The embodiments illustrated in FIGS. 37-39 are exemplary, and the array electrodes can have varying dimensions ranging between, e.g., about 1 to 15 microns, preferably about 2 to 10 microns. The 2 micron disc arrays have been fabricated with 20 microns center to center distance, 5 micron disc arrays have been fabricated with 50 microns center to center distance, and 10 micron disc arrays have been fabricated with 100 microns center to center distance. The interdigitated electrodes have been fabricated with 2 microns, 5 microns and 10 micron fingers in combination with 2 microns, 5 microns and 10 micron gaps, respectively. Finally, individually addressable microband arrays have been fabricated with 2, 5 and 10 micron wide bands spaced 40, 100, and 200 microns apart.

A further embodiment is a microfluidic sensor that includes one or more electrochemical sensors of the invention in communication with a microfluidic channel through which the fluid sample passes during the detection procedure. The coated electrodes are positioned with their coating in communication with the microfluidic channel through which the fluid sample passes during the detection procedure.

Regardless of the array format and/or of the format of the planar electrochemical cell, microfluidic devices are preferably fabricated from materials that are biocompatible and resistant to biofouling. Several existing materials, widely used for the fabrication of fluidic channels, can address these basic needs. Two categories can be distinguished among them: those based on glasses, such as glass, Pyrex, quartz, etc. (Ymeti et al., "Integration of Microfluidics with a Four-channel Integrated Optical Young Interferometer Immunosensor," *Biosens. Bioelectron.* 20:1417-1421 (2005), which is hereby incorporated by reference in its entirety); and those based on polymers such as polyimide, photoresist, SU-8 negative photoresist, PDMS, and silicone elastomer PDMS (McDonald et al., "Fabrication of Microfluidic Systems in poly(dimethylsiloxane)," *Electrophoresis* 21:27-40 (2000), which is hereby incorporated by reference in its entirety), liquid crystal polymer, Teflon, etc. While the glass materials have great chemical and mechanical resiliency, their high cost and delicate processing make them less frequently used for this kind of application. In contrast, polymers have gained wide acceptance as the materials of choice for fluidics applications. Moreover, structuring technologies involved in their use, such as bonding, molding, embossing, melt processing, and imprinting technologies, are now well developed (Mijatovic et al., "Technologies for Nanofluidic Systems: Top-down vs. Bottom-up—A Review," *Lab on a Chip* 5:492-500 (2005), which is hereby incorporated by reference in its entirety). An additional advantage of polymer-based microfluidic systems is that valves and pumps made with the same material are readily integrated (Unger et al., "Monolithic Microfabricated Valves and Pumps by Multilayer Soft Lithography," *Science* 288: 113-116 (2000), which is hereby incorporated by reference in its entirety).

PDMS and SU-8 resist are particularly well studied as raw materials for the construction of microfluidic systems. Their mechanical and chemical comportment are strongly disparate: SU-8 is stiffer (Blanco et al., "Microfluidic-optical Integrated CMOS Compatible Devices for Label-free Biochemical Sensing," *J Micromechanics Microengineering* 16:1006-1016 (2006), which is hereby incorporated by reference in its entirety) than PDMS, and so the structuring techniques of these two materials are different. PDMS is also subject to wall collapse, depending on the aspect ratios of the channels (Delamarche et al., "Stability of Molded polydimethylsiloxane," *Adv. Materials* 9:741-746 (1997), which is hereby incorporated by reference in its entirety). Their chemical properties are an important aspect for the wanted application. They both have a hydrophobic surface after polymerization, which can lead to an attachment of the proteins onto the PDMS walls, and can fill the channel in case of small cross-section. Both the surface of PDMS and of SU-8 can be treated with a surfactant or by plasma to become hydrophilic (Nordstrom et al., "Rendering SU-8 Hydrophilic to Facilitate use in Micro Channel Fabrication," *J Micromechanics Microengineering* 14:1614-1617 (2004), which is hereby incorporated by reference in its entirety). The composition of SU-8 can also be modified before its structuring to become hydrophilic after polymerization (Chen and Lee, "A Bonding Technique using Hydrophilic SU-8," *J Micromechanics Microengineering* 17:1978-1984 (2007), which is hereby incorporated by reference in its entirety). Fouling of the channel surface via nonspecific binding is an obvious concern for any microfluidic application. Anecdotal evidence suggests that SU-8 is less prone to this, but it is important to note that chemical treatment methods are also available for improving the performance of PDMS (Lee and Vörös, "An Aqueous-based Surface Modification of poly(dimethylsiloxane) with poly(ethylene glycol) to Prevent Biofouling," *Langmuir* 21:11957-11962 (2004), which is hereby incorporated by reference in its entirety).

FIG. 79A illustrates a PDMS-based microfluidic sensor 400. The bottom of the channel is a microfabricated chip 402 with a planar electrochemical cell 404 patterned on its surface. The electrodes formed on the surface of the chip are connected to bonding pads 406, and the electrodes are coated with a film of the present invention. A microchannel 408 is defined by the chip surface 402 and a PDMS slab 410 that is adhered to the surface of the chip using standard procedures. A sample port 412 and a reservoir port 414 are also defined by the PDMS slab, allowing for the sample to flow over the surface of the electrochemical cell. The sample transport is provided by, e.g., passive pumping (see Chen et al., "Computation of Transient Flow Rates in Passive Pumping Micro-fluidic Systems," *Lab. Chip.* 9:107-114 (2009); Chen et al., "Lab-on-Chip Flow Injection Analysis System without an External Pump and Valves and Integrated with an In Line Electrochemical Detector," *Anal. Chem.* 81:9955-9960 (2009), each of which is hereby incorporated by reference in its entirety).

FIG. 79B illustrates the structure of the planar electrochemical cell 404 formed in the microfluidic sensor 400. The electrochemical cell 404 includes a microdisc array working electrode 422, counter electrode 423, and reference electrode 421. The working electrode 422 is covered with a coating of the present invention, and the microfluidic channel 408 is formed across all three electrodes of the array. As an alternative to a microdisc array, a microarray band or interdigitated array can be used.

As noted above, the electrochemical sensor or sensor array is intended to be in contact with a fluid sample. As such, during use, the electrochemical sensor is intended to be exposed to a fluid sample. To facilitate exposure to the fluid sample, a fluid sample can be drawn from the patient and then exposed ex vivo to the sensor or sensor array. The sensor or sensor array according to any embodiment described herein is suitable for ex vivo detection of bioavailable drug concentration.

FIG. 80 illustrates one example of an ex vivo sensor device 500. Any computer or microprocessor controlled analyzer equipped with a flow-through electrochemical cell that incorporates the membrane coated electrochemical sensor can be used for the feedback controlled delivery of propofol or other electrochemically active drugs. In FIG. 80, a computer or microprocessor 502 controls a sampling valve 506 and peristaltic pump 514 for sampling blood from a patient via lines 510, 512 and for sampling standards and carrier solution (collectively, 508) via lines 509, 512. A potentiostat 504 is also controlled by computer/microprocessor 502 for the electrochemical measurements of the electrochemically active drug in blood samples and in the calibration standards using the microfluidic sensor 400. Depending on the measured concentration of the electrochemically active drug in the blood sample, a drug delivery device 516 under control of the computer/microprocessor 502 adjusts dosing of the electrochemically active drug to the patient based on the measurements. Although the microfluidic sensor as shown includes a three-electrode microarray, as described above, it should be appreciated that the electrochemical cell can contain any desired number of electrodes depending on the type of measurement operation performed.

Alternatively, during use, the sensor or sensor array may reside in a device that is retained in fluid communication with the fluid sample in vivo. Examples of this type of sensor construction include, without limitation, indwelling solid fibers with electrochemical sensor(s), collinear catheters (that is, a cylinder or fiber inside another) equipped with electrochemical sensor(s), and catheters having different proximal and distal sensors. This type of device, because it is in constant exposure to the fluid sample during use, is preferably the electrochemical sensor having the coating over the electrodes as described above (which prevents biofouling of the working electrode during use) or a sensor array (containing a plurality of working electrodes) as described above.

One example of an in vivo device is a catheter of the type illustrated in FIG. 41. A catheter 600 includes a body and a lumen, and one or more electrochemical sensors 601 secured in the body with at least a portion of the sensor being in communication with either the lumen or externally of the body (such that the sensor(s) are exposed to the interior of a blood vessel). Preferably, the catheter 600 is an in-dwelling catheter. The catheter 600 can include a plurality of the electrochemical sensors 601 located at various positions along the body. During use, the catheter can be inserted into a blood vessel of a patient so that sensing of a bioavailable drug can be performed in vivo.

Other types of suitable catheters include, without limitation, indwelling solid fibers with electrochemical sensor(s), collinear catheters (that is, a cylinder or fiber inside another) equipped with electrochemical sensor(s), and catheters having different proximal and distal sensors.

The electrochemical sensor or sensor array of the present invention is particularly useful in combination with a target-controlled infusion drug delivery device. The design and construction of such drug delivery devices are well known in the art. The present invention involves modifying these known devices to include an electrochemical sensor or sensor array of the invention as a component in a feedback mechanism that is designed to control drug delivery (to the patient) based, at least in part, on the bioavailable drug concentration in a fluid sample from the patient (FIG. 42). Thus, rather than relying solely on pharmacodynamic models or physiological feedback mechanisms, the drug delivery device of the present invention also relies on the bioavailable drug concentration from the patient. As shown in FIG. 81, the bioavailable drug concentration can be detected in blood/lymph (central compartment), CSF (first compartment), or exhaled breath (third compartment).

Exemplary drug delivery devices that can be modified include those described in U.S. Pat. No. 7,220,240 to Struys et al., U.S. Patent Publ. Nos. 2007/0118075 to Kimmo et al. and 2006/0167722 to Struys et al., J. Glen et al., "The Development of 'Diprifusor': A TCI System for Propofol," *Anesthesia*, 53, Supplement 1, pp. 13-21 (1998); J. Gray et al., "Development of the Tehcnology for 'Diprifusor' TCI Systems," *Anesthesia*, 53, Suppl. 1, pp. 22-27 (1998), each of which is hereby incorporated by reference in its entirety.

With reference to FIG. 43, a block diagram depicting one embodiment of a drug delivery system 700 that is equipped with an electrochemical sensor of the invention is illustrated. The system 700 includes user interface 712, software controlled controller 714, peripherals 715, power supply 716, external communications 710, patient interface 717, and drug delivery 719, where sedation and analgesia system 700 is operated by user U to provide drug delivery (e.g., sedation and/or analgesia) to patient P. The basic structure of this sedation and analgesia system 700 is disclosed by U.S. Pat. No. 6,745,764 to Hickle, which is hereby incorporated by reference in its entirety; but the system is modified such that the patient interface 717 includes an electrochemical sensor of the present invention.

Briefly, the drug delivery 719 includes a drug reservoir (which preferably, during use, includes an electrochemically active drug of the type described above), and a pump in communication with the drug reservoir.

The patient interface 717 includes an electrochemical sensor or sensor array of the present invention, which produces an output current from a reduction-oxidation (redox) reaction at electrochemical sensor in the presence of the bioavailable drug. As noted above, the electrochemical sensor or sensor array of the present invention can be located ex vivo or in vivo. Regardless of its position with respect to the patient, the amount of output current produced is in direct correlation to an amount of bioavailable drug detected during a measuring event (i.e., within a patient fluid sample). The output current from electrochemical sensor is coupled to a current/voltage detector which can be configured to convert the detected current output from electrochemical sensor into a corresponding calibrated value.

Using the sensor or sensor array of the present invention in combination with fluid samples containing known concentrations of a bioavailable form of a drug, it is possible to generate empirical data that correlates the detected conditioned current/voltage levels with the bioavailable drug concentration. This empirical data can be used to form a model, which can be stored in memory.

The controller 714 can include an input/output (I/O) card coupled through a data bus into a processor. The conditioned current at the output of current/voltage detector is provided to an analog to digital converter (ADC) inside controller 714. The ADC converts the analog output of current/voltage detector to a corresponding digital value for processing by controller 714. The digital value of the detected current is provided to central processing unit (CPU)/processor via an internal bus. By way of example only, the ADC can be an 8-bit ADC, although other types of ADCs may also be used as known to those skilled in the art.

CPU/processor receives and processes the digital current from ADC. CPU/processor can be in the form of a single board computer which includes one or more microprocessors or CPUs. Controller 714 may be conveniently implemented using one or more general purpose computer systems, microprocessors, digital signal processors, and microcontrollers, programmed according to the teachings described and illustrated herein. For example, CPU/processor can be an Intel Core Duo® processor provided by Intel Corporation of Santa Clara, Calif. Alternatively, CPU/processor may be a special purpose processor designed and fabricated to carry out various aspects of this invention. For example, CPU/processor may be an application specific integrated circuit (ASIC) chip.

CPU/processor is coupled to a memory that stores various settings for the delivery system 700. For example, memory stores one or more threshold values of the output current from electrochemical sensor, which threshold values represent the target range for the bioavailable drug concentration, i.e., minimum and maximum bioavailable drug concentrations. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a computer programming language or software package for carrying out one or more aspects of the present invention as described and illustrated herein, although some or all of the programmed instructions could be stored and/or executed elsewhere. For example, instructions for executing steps outlined in FIG. 44 can be stored in a distributed storage environment where memory is shared between one or more controllers similar to controller 714.

Controller 714 can include an input/output (I/O) device (e.g., an I/O card) coupled to CPU/processor. The user interface 714 (e.g., display with keypad), external communications 710, peripherals 715, patient interface 717, and drug delivery 719 can be coupled to the controller 714 via and internal bus. The I/O device includes a bi-directional port for communication to/from other computing and/or electronic devices via a link. The port can also be used for charging the device via power supply 716, which can be a battery. By way of example only, the port can be a Universal Synchronous Bus (USB) port, although other types of communication and input/output ports may also be used, as known to those skilled in the art.

The internal bus is designed to carry data, power and ground signals, as known to one skilled in the art. By way of example only, internal bus can be a Peripheral Component Interconnect (PCI) bus, although other types of local buses (e.g., Small Computer System Interface or "SCSI") may also be used, as known to those skilled in the art.

User interface 712 can be a suitable display panel on which instructions and data are presented to a user in both textual and graphic format. In addition, display 712 can include a touch screen also coupled to the I/O device for accepting input from a user (e.g., a medical professional). The display can display the concentration of the bioavailable drug concentration based on the output current or voltage that is generated by the electrochemical sensor. Further, the display can be substituted by or used in conjunction with an audio device (e.g., a speaker, a buzzer, or a beeper alarm) controlled by CPU/processor to indicate whether the bioavailable drug concentration is too high or too low.

The controller 714 receives power from a power supply 716. Power supply 716 can be a battery or a direct pluggable outlet to a main power-line. Alternatively, power supply 716 may be a switched mode power supply (SMPS) commonly used in computer systems, although other forms for powering controller 714 using power supply may also be used, as known to those skilled in the art.

The controller 714 preferably carries out a PID controller algorithm using the input from the electrochemical sensor. The PID controller involves three separate parameters: the Proportional, the Integral and Derivative values. The Proportional value determines the reaction to the sensed bioavailable drug concentration, the Integral value determines the reaction based on the average bioavailable drug concentration, and the Derivative value determines the reaction to the rate at which the bioavailable drug concentration has been changing. In the context of the present invention, any one of these parameters or the weighted sum of any two (or all three) of these parameters can be used to adjust the rate of drug discharge by the drug delivery 719.

From the foregoing, it should be appreciated that the present invention also relates to a method for electrochemical detection of bioavailable drug concentration in a fluid sample, which includes the steps of: exposing a fluid sample to an electrochemical sensor comprising one or more electrodes and a coating that surrounds the one or more electrodes, which coating is capable of partitioning the bioavailable drug directly from the fluid sample; and detecting an oxidation/reduction current during said exposing, wherein the detected current relates to the concentration of bioavailable drug in the fluid sample.

This system and method can also be utilized in detecting the concentration of bioavailable drug in a vapor sample such as exhaled breath. In this embodiment, the sensor is positioned within the exhalation side of a ventilation/respiratory circuit.

The present invention also relates to a method of modulating drug delivery that includes the steps of: exposing a fluid or vapor sample obtained from a patient to an electrochemical sensor of the present invention, the electrochemical sensor capable of detecting an electrochemical signal in the coating that relates to a concentration of bioavailable drug in the fluid or vapor sample, and then modulating delivery of the drug into a patient based on the concentration of the bioavailable drug in the fluid or vapor sample.

Because the patient receiving the drug is monitored continuously during the procedure for which the drug is being administered, the detection of bioavailable drug concentration is preferably performed repeatedly during a surgical procedure such that appropriate feedback control is provided to maintain the bioavailable drug concentration within an optimal range. While the frequency of the detection step can vary depending on the pharmacokinetics of a particular drug, it is generally desirable to repeat the detection procedure at least every 5 minutes, more preferably at least every 2 to 3 minutes. More frequent detection procedures can also be carried out.

As a consequence of the frequent monitoring of bioavailable drug concentration, the output from the electrochemical sensor can be used to modify operation of the drug pump in real time (as noted above). Preferably, adjustments in drug delivery, if any, are made instantaneously following the detection event (i.e., within the capacity of the processor control system). The method of modulating drug delivery can include the embodiment illustrated in FIG. 44.

Upon initiation of drug delivery at step 802, either via bolus or predetermined delivery rate, drug delivery begins. This step may occur at a predetermined time prior to surgery. Prior to beginning the surgical procedure and periodically during the course of the surgical procedure, the query at step 804 initiates measurement of the bioavailable drug concentration using the electrochemical sensor of the present invention. If the bioavailable drug concentration remains with the predetermined range (e.g., about 3 to about 8 µg/ml for Propofol as an anesthetic, or about 1 to about 2 µg/ml for Propofol as a sedative), then at step 806 the existing drug delivery rate is maintained. (If this is the first measurement with the bioavailable drug concentration within the target range, the surgical procedure can begin at this time.) If the bioavailable drug concentration is outside the predetermined range, then the output of the electrochemical sensor is assessed at steps 806 and 808, respectively, to determine whether the detected bioavailable drug concentration is above or below the predetermined range. If the bioavailable drug concentration detected during a single detection step is above an acceptable range, then the rate of drug delivery can be reduced or entirely withdrawn for a short duration at step 807. A reduction can be automated via the PID controller. If the bioavailable drug concentration detected during a single detection step falls below an acceptable range, then an immediate change in the rate of drug delivery can be made, a single bolus can be administered, or both, at step 809. An increase can be automated via the PID controller. These steps can be carried out using a suitable software algorithm, and they can be repeated at periodic intervals during the surgical procedure. Upon completion of the surgical procedure, the drug delivery protocol can be withdrawn at step 810.

As is known in the art, the software algorithm (PID controller) used to adjust drug delivery rate can also rely on one or more patient physiological response parameters, including blood pressure, heart rate, temperature, and EEG parameters. See Wang et al., "New Target Controlled Infusion Using a Hybrid Physiology Based Pharmacokinetic Model," *IEEE* 1822-1824 (2008) (ISBN: 978-1-4244-1747-6), which is hereby incorporated by reference in its entirety. In addition to the foregoing, it should be appreciated by persons of skill in the art that drug administration is not limited to surgical procedures, but can also be effectively used in other settings, e.g., during intensive care or post-operative care.

EXAMPLES

The Examples set forth below are for illustrative purposes only and are not intended to limit, in any way, the scope of the present invention.

Example 1—Macroelectrode Design and Use for Propofol Detection 2,6-Diisopropylphenol (Propofol, DIPP) was purchased from Aldrich (D126608, St. Louis, Mo.) and used as received for preparation of stock solution 0.01M in 0.1 M NaOH or 0.1M in 3:7 mixture of water to methanol. All other aqueous solutions were prepared with Milli-Q Gradient A10 purified water.

Voltammetric measurements were performed using the Autolab/PGSTAT12 system equipped with the GPES Version 4.8 (Eco Chemie, Urtrecht, NL) in a standard three-electrode cell setup, i.e., with the platinum (2 mm diam.) or glassy carbon (BAS, 3 mm d.) disks macroelectrodes serving as working electrodes and the double junction (with 10% KNO3) Ag/AgCl Model 90-02 (Orion Research, Beverly, Mass.) and Pt-wire as reference and counter electrodes, respectively. Working macroelectrodes were always polished (using 0.3 µm particle size alumina) prior to use. The carbon microelectrodes were manufactured by standard lithography methods (Guillorn et al., "Individually Addressable Vertically Aligned Carbon Nanofiber-based Electrochemical Probes," *J. Appl. Phys.* 91:3824 (2002), which is hereby incorporated by reference in its entirety).

Cyclic voltammetry on a platinum working electrode in the potential range of −0.3 to 1.4V in $10^{-2}$M $H_2SO_4$ did not demonstrate an electrochemical signal for DIPP at concentrations up to $4 \times 10^{-4}$M. Rather, the significant oxidation current signal seen only marks the electrode passivation in platinum oxide region, where observed. Voltammetry in the potential range of −0.7 to 1V in $10^{-2}$M NaOH also failed to demonstrate a signal for the same concentration of DIPP.

Figure 1:
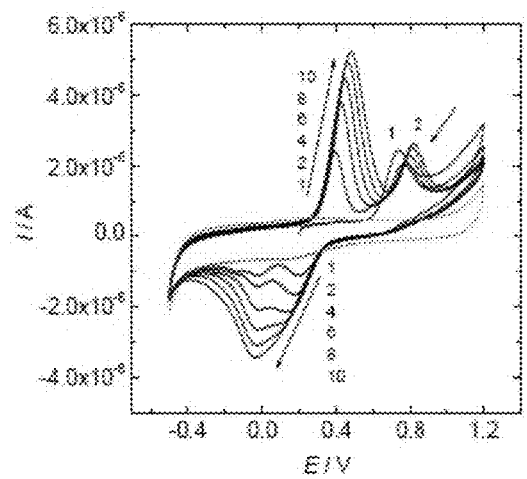
FIG. 1 is a cyclic voltammogram of $10^{-4}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

Conversely, cyclic voltammetry on a glassy carbon electrode in the potential range of −0.5 to 1.2V in $10^{-2}$M $H_2SO_4$ for a concentration of $10^{-4}$M DIPP demonstrated an increasing current signal with repeated cycles (FIG. 1). Starting the cycling at 0.2V in the positive potential direction, the first oxidation mark in shape of current peak was observed at around 0.7V. On the negative scan, there appeared two reduction peaks at the start of cycling, which grew with continual cycling and merged later into one with peak potential around 0V. On the positive scan direction, the growth of an additional oxidation peak at 0.4V was observed. The latter two growing peaks may be attributed to the development of an electrochemically active biofilm layer on carbon surface with the peak at 0.7V growing apparently at much slower rate. The slightly positive shifted can be correlated exclusively with direct DIPP oxidation—slower growth reflecting most likely an increase of effective electrode surface.

Figure 2:
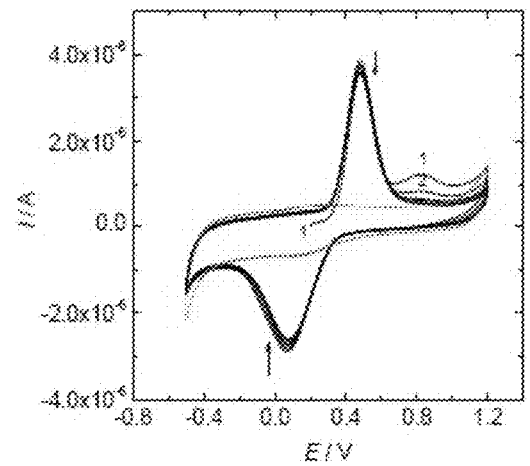
FIG. 2 is a cyclic voltammogram of $10^{-2}$M $H_2SO_4$ only, using 100 mV/s scan, 10 cycles; this was carried out after 10 cycles following DIPP introduction. Working electrode=glassy carbon; counter electrode=Pt; and reference electrode=Ag/AgCl. The DIPP peak disappeared by the third cycle shown.

These statements can be supported by voltammetry of developed layer in background electrolyte in the absence of DIPP (FIG. 2). As can be seen, with continuous cycling, only two peaks corresponding to the electrochemically active layer remained and the direct oxidation peak of DIPP rapidly disappeared after oxidation of adsorbed traces of (see $3^{rd}$ cycle, FIG. 2). The overall reaction resulting in the electrochemically active layer (FIG. 2 arrow, biofilm) formed on the surface of the glassy carbon electrode is of uncertain origin.

Figure 3:
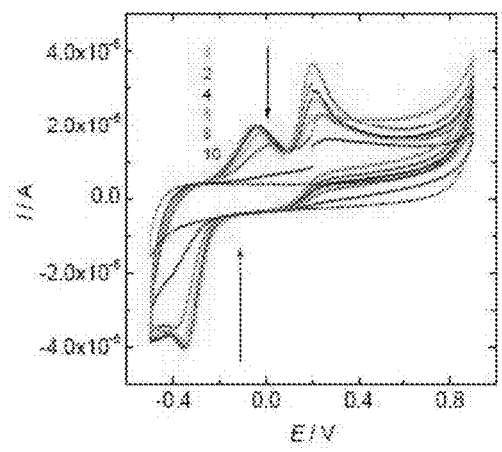
FIG. 3 is a cyclic voltammogram of $2 \times 10^{-4}$M DIPP in $10^{-2}$M NaOH using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 4:
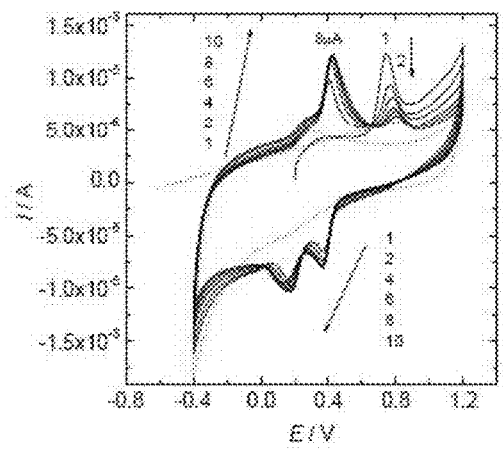
FIG. 4 is a cyclic voltammogram of $10^{-4}$M DIPP in $10^{-2}$M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.

Similar EC behavior can be expected from a polymerized conducting polymer layer or from deposited and still electrochemically active but insoluble DIPP oxidation product. A roughly similar shape of voltammogram was obtained in $10^{-2}$M NaOH (−0.5 to 0.9V), but with significant difference, all developed peaks decreased with continuous cycling (FIG. 3). The minimally active formed passivation layer when further cycled in $10^{-2}$M NaOH disappeared immediately after immersion into solution, thus showing its high solubility. The consequences that follow from these observations therefore suggest the importance of protons in overall reaction scheme and demonstrate that analysis in acidic media is required. It's also noteworthy the effect of methanol in stock solution on the shape and rate of the growing current. FIGS. 1-3 depict curves measured without presence of methanol in sample. Same experiment in FIG. 1 was performed with methanol in the sample solution and is shown in FIG. 4. The differences in the curves, including those obtained for background electrolytes are hypothesized to result from methanol co-adsorption on carbon surface.

Figure 5:
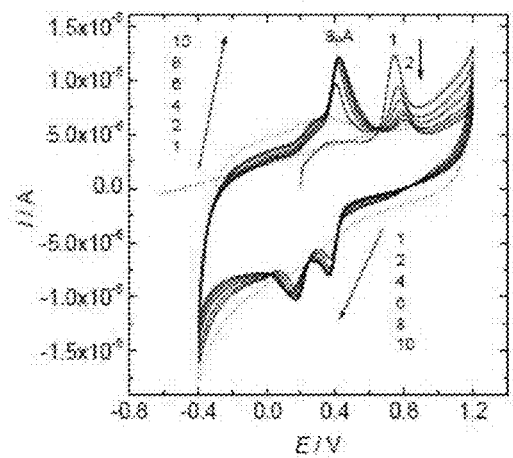
FIG. 5 is a cyclic voltammogram of $10^{-4}$M DIPP in $10^{-1}$M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.
Figure 6:
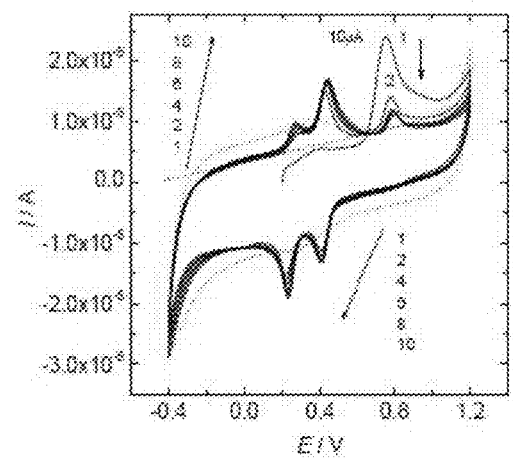
FIG. 6 is a cyclic voltammogram of $10^{-4}$M DIPP in 1M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.
Figure 7:
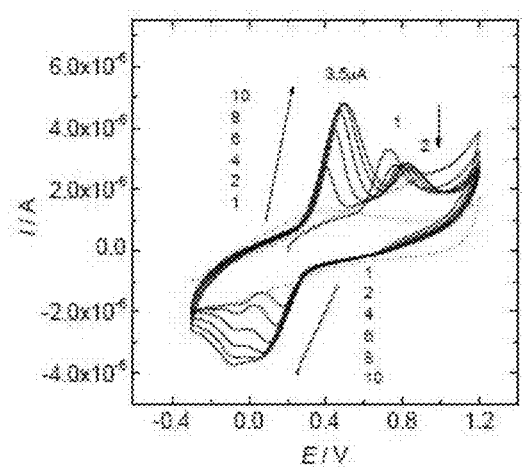
FIG. 7 is a cyclic voltammogram of $10^{-4}$M DIPP in $10^{-3}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

The concentration effects of the $H_2SO_4$ solute in presence of methanol are shown in FIGS. 5-6. The greater the concentration of $H_2SO_4$ in solution, the sooner the non-growing stable shape of curves is reached.

Figure 8:
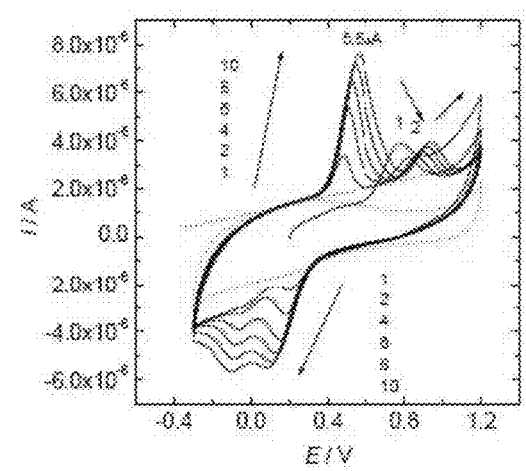
FIG. 8 is a cyclic voltammogram of $10^{-4}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 9:
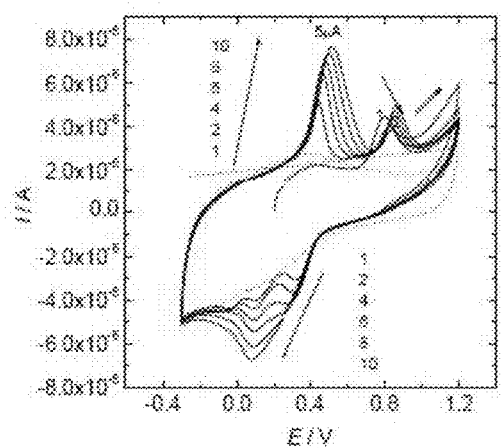
FIG. 9 is a cyclic voltammogram of $10^{-4}$M DIPP in $10^{-1}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 10:
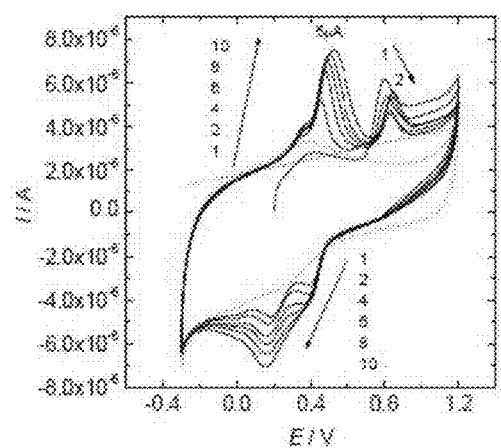
FIG. 10 is a cyclic voltammogram of $10^{-4}$M DIPP in 1M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

Similar pH dependence with aqueous samples is presented in FIGS. 7-10. These show maximum peak currents and the greatest growth at a concentration of $10^{-2}$M $H_2SO_4$ (FIG. 8 replicates the experiment in FIG. 1). Higher concentrations of protons in the solution do not increase the signal intensity or current peak height. Rather, there is an increase in the system noise demonstrated by the broadening of the redox curves in FIGS. 9-10.

Figure 11:
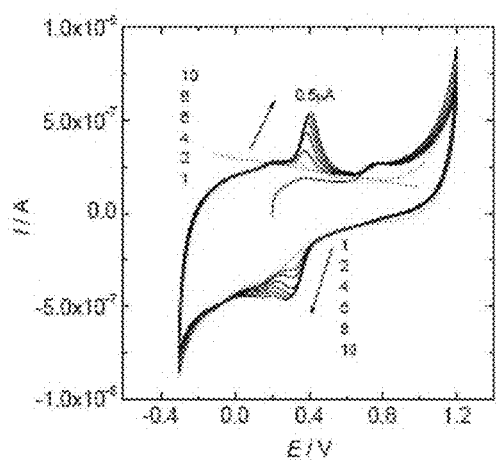
FIG. 11 is a cyclic voltammogram of $10^{-5}$M DIPP in $10^{-2}$M $H_2SO_4$ using 10 mV/s scan, 10 cycles. The DIPP was introduced from a 0.01M solution in 0.1M NaOH water. Working electrode=glassy carbon; counter electrode=Pt; and reference electrode=Ag/AgCl.
Figure 12:
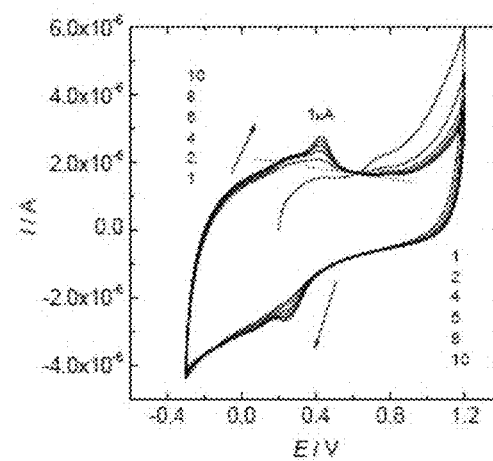
FIG. 12 is a cyclic voltammogram of $10^{-5}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

The potential effects of the cycling rate on the DIPP signal were examined in FIGS. 11-12. These show the effects of different voltage cycling scan rates on the growing DIPP signal peaks at lower concentrations, e.g. $10^{-5}$M DIPP. A slower cycling rate generates a larger signal peak in identical solutions, indicating that the sensitivity of the DIPP signal can be optimized by the voltammetry method used (see also FIG. 23, infra). Importantly, the concentration of DIPP used in this set of experiments is in the therapeutic range of clinical use.

Figure 13:
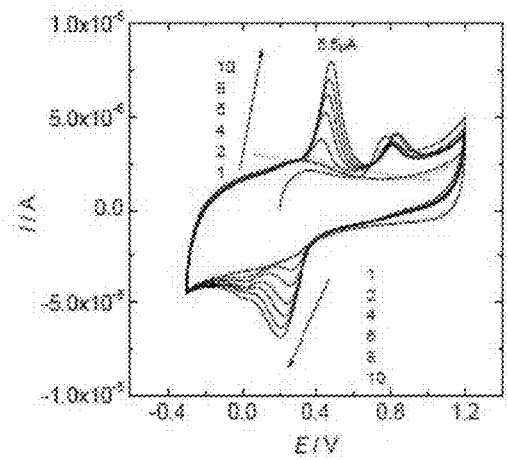
FIG. 13 is a cyclic voltammogram of $10^{-4}$M DIPP in $10^{-2}$M $H_2SO_4$+0.05% Tween20 using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 14:
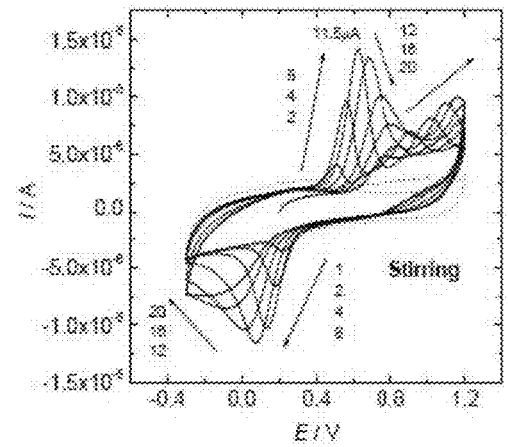
FIG. 14 is a cyclic voltammogram of $10^{-4}$M DIPP in $10^{-2}$M $H_2SO_4$+0.05% Tween20 using 100 mV/s scan, 20 cycles with stirring. The DIPP was introduced from a 0.01M solution in 0.1M NaOH water. Working electrode=glassy carbon; counter electrode=Pt; and reference electrode=Ag/AgCl.

Some of the biophysical characteristics of the DIPP biofilm were investigated using a series of studies to determine whether the DIPP signal could be modified or enhanced by the presence of various detergents in the solution (FIGS. 13-14). These studies depict the effect of the surfactant Tween-20 on the regularity of surface layer growth and the additional effects on growth by stirring of the solution.

Figure 15:
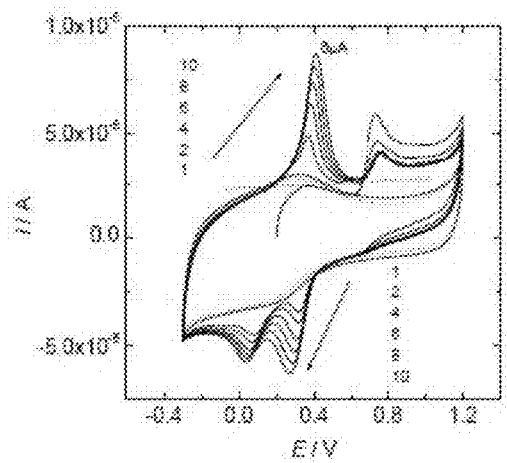
FIG. 15 is a cyclic voltammogram of $10^{-4}$M DIPP in $10^{-2}$M $H_2SO_4$+$10^{-3}$M sodium lauryl sulfate using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 16:
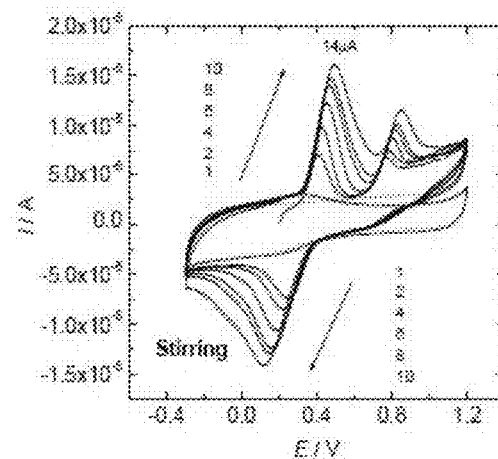
FIG. 16 is a cyclic voltammogram of $10^{-4}$M DIPP in $10^{-2}$M $H_2SO_4$+$10^{-3}$M sodium lauryl sulfate using 100 mV/s scan, 10 cycles with stirring. The DIPP was introduced from a 0.01M solution in 0.1M NaOH water. Working electrode=glassy carbon; counter electrode=Pt; and reference electrode=Ag/AgCl.

Similar studies were performed using $10^{-3}$M sodium lauryl sulfate (SDS detergent) and are shown in FIGS. 15-16. These studies show an increasing DIPP signal in the presence of SDS both with and without stirring of the solution. This was evident both in the accumulation times and stripping current peak with or without SDS.

Figure 17:
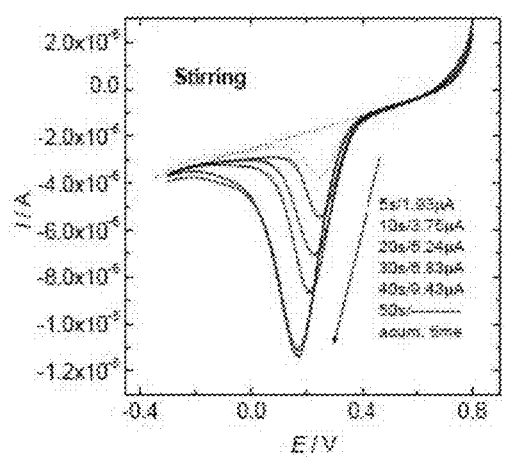
FIG. 17 is a stripping voltammogram of $10^{-4}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.
Figure 18:
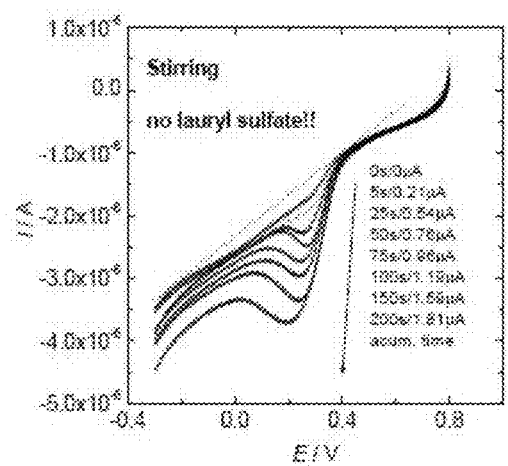
FIG. 18 is a stripping voltammogram of $10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

The studies in FIGS. 17-18 also clearly demonstrate that the maximal EC signal is obtained within 30 seconds when the solution is stirred in the presence of SDS. Stirring alone does not optimize the signal acquisition as is shown in FIG. 18. Here, the maximal signal was not been reached even after 200 seconds in the absence of SDS in the solution. Thus, the presence of SDS detergent is important (but not critical, see FIG. 19, below) for the rapid determination of the DIPP electrochemical signal.

Figure 19:
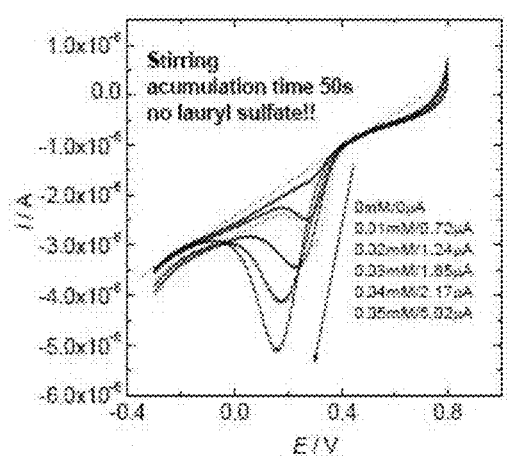
FIG. 19 is a stripping voltammogram of 1, 2, 3, 4, $5 \times 10^{-5}$M DIPP in $10^{-2}$M $H_2SO_4$ without sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.
Figure 20:
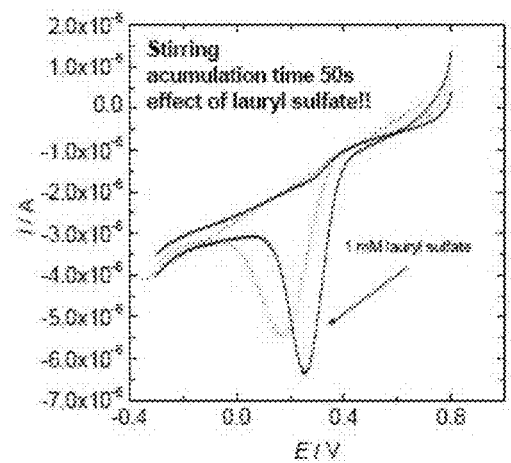
FIG. 20 is a stripping voltammogram of $6 \times 10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

The studies in FIGS. 19-20 demonstrate that the DIPP signal is clearly concentration dependent (accumulation time 50 s) even in the absence of SDS for concentrations of DIPP>$1 \times 10^{-5}$M. The signal intensity (current) is increased in the presence of SDS, thus enhancing the potential to more accurately quantify the level of the drug in the presence of SDS detergent.

The relationship between the SDS concentration and the DIPP signal intensity is shown in FIG. 21. The optimal SDS concentration which maximizes the DIPP signal under stirring conditions is $10^{-3}$M (1 mM). Under these conditions, a robust DIPP signal is seen at concentrations above $3 \times 10^{-5}$M (FIG. 22). Finally FIG. 23 shows the relationship between the charge under the DIPP stripping peak and the voltage scan rate. See also FIGS. 11-12 supra.

Example 2—Microelectrode Design and Use for Propofol Detection

To develop a simple and faster "in-line" analytical technique for small sample volumes, the glassy carbon macroelectrode of Example 1 was replaced by a carbon microelectrode having the structure illustrated in FIG. 24.

The carbon microelectrode was prepared by the Oak Ridge National Laboratory using microfabrication technologies as previously described in the literature, (Guillorn et al., "Individually Addressable Vertically Aligned Carbon Nanofiber-based Electrochemical Probes," *J. Appl. Phys.* 91: 3824 (2002); McKnight et al., "Effects of Microfabrication Processing on the Electrochemistry of Carbon Nanofiber Electrodes," *J Phys Chem B* 107(39):10722-10728 (2003), each of which is hereby incorporated by reference in its entirety).

Having fabricated the carbon microelectrode, additional experiments were performed to the include a broad pH range (acidic, neutral, and basic solutions). These results are illustrated in FIG. 25. FIG. 25 shows cyclic voltammograms of Propofol using a 25-µm-diameter carbon microelectrode obtained in acidic (pH1, blue curve), physiologic (pH7; dashed line for 1st cycle, red line for 2nd cycle), and alkaline (pH11, green curve) solutions.

The steady-state current of oxidized Propofol measured in acidic solution is two times greater than in alkaline solution (FIG. 25, ~1.8 vs. ~3.5 i/nA). This implies that the mechanism of electrochemical oxidation of Propofol is different between acidic and alkaline solutions. Either i) the number of electrons involved in the electrode reaction at acidic pH is twice the number of electrons involved at alkaline pH, or ii) there are two successive one-electron transfer reactions at electrode surface in acidic solution. Previous reports on the electrochemical oxidation of other phenol molecules support the latter interpretation of sequential one-electron transfer (Lund and Hammerich, *Organic Electrochemistry*, $4^{th}$ Revised and Expanded Revision, Marcel Dekker, Inc, New York, 2001), which is hereby incorporated by reference in its entirety). In physiological solution (pH 7), no oxidation wave was observed in the first forward scan (FIG. 25, dashed line). However, a reduction peak appeared in the reverse scan, indicating the formation of an electrochemically active film on the electrode surface (lower dashed line −0.1 i/µA). In the second scan (red curve), an oxidation peak of the reduced film was observed (0.1 i/nA), and the reverse scan presents an increasing reduction peak.

Based on these mechanistic studies on the oxidation of DIPP on graphite microelectrode surfaces, new protocols were developed for its electrochemical quantification in acidic and physiologic solutions. Both methods have an order of magnitude better (lower) detection limit than the method of Example 1 ($1 \times 10^{-6}$M), which should permit the quantitative measurement of Propofol over the entire therapeutic and sub-therapeutic range of the drug. In addition, the microelectrode method is simpler and faster.

To evaluate the feasibility of detecting Propofol in a physiological environment using the carbon fiber microdisc electrode, Propofol was detected in 0.01 M pH 7.0 HEPES solution by stripping analysis. In this assay, the potential was held at 0.8V for 30 s to accumulate the conductive components, and then the potential was switch to −0.4V for 10 s to reduce the conductive film. The potential was scanned from −0.4 V to 0.65 V at 0.1V/s right after the reduction. 1 µM Propofol can be detected by this method, which is ~1 magnitude lower than the target therapeutic concentration in the blood (FIG. 26).

Measurement of DIPP in acidic solutions is relatively simple and fast. Electrode fouling does occur as was observed in Example 1, but multiple measurements can be made using a single microelectrode. DIPP can be measured in neutral solutions, but requires a "stripping" measurement. First, the electrode potential is set to a certain value for a short period of time (e.g., 2-3 minutes). During this time an oxidation product is collected on the electrode surface. Next, the electrode potential is set to the value at which the accumulated film is stripped off. It is somewhat slower, but the detection limit can be improved if the collection time is increased.

DIPP can also be measured in alkaline solutions; however, the electrode fouling is greater under alkaline conditions. In repeated experiments, the measured signal declines rapidly from its original value and the electrode surface must be renewed after each experiment. Due to the large mass transfer rate on the carbon microelectrode, problems related to the electrode fouling during the electrochemical measurement of DIPP significantly decreased relative to the macroelectrode. However, the decreasing current values indicate changes in the electrode surface properties, which make the method inadequate for the continuous in-line monitoring of DIPP levels for extended periods of time. Instead of continuous monitoring, serial measurements can be performed using individually addressable electrode arrays. By integrating such array sensors into a small volume flow through manifold the DIPP concentrations could be measured semi-continuously. Since each measurement will be performed on a different, single-use electrode, biofouling should not influence the analytical results.

Example 3—Carbon Nanofiber Sensor Array and Use for Propofol Detection

A prototype carbon nanofiber (CNF) array containing a chambered carbon nanofiber electrochemical sensor arrays with 40 individually addressable fibers was obtained from Oak Ridge National Laboratory. The array was prepared using known techniques (Guillorn et al., "Individually Addressable Vertically Aligned Carbon Nanofiber-based Electrochemical Probes," *J Appl. Phys.* 91: 3824 (2002); McKnight et al., "Effects of Microfabrication Processing on the Electrochemistry of Carbon Nanofiber Electrodes," *J Phys Chem B* 107(39):10722-10728 (2003), each of which is hereby incorporated by reference in its entirety). Each fiber in the array can be individually queried and the electrochemical signal assessed. The reproducibility and performance of selected fibers within the array was tested in ferrocene methanol solution. Signals obtained from selected CNFs were similar and summed appropriately when the currents were added together.

The reproducibility and performance of selected fibers within the array was tested in ferrocene methanol solution (FIG. 27). Signals obtained from selected CNFs were similar and summed appropriately when the currents were added together. Some variance between CNFs was present within the array and represented differences in the final surface areas of the fibers, which are grown using a carbon sputtering method. The variances within the array demonstrate the need for measuring the signal of each CNF fiber relative to a reference electrode for calibration.

$Cl^-$ ion and bovine serum albumin ("BSA") interfere the voltammetric response of DIPP in pH 7 solutions at their blood concentrations. Unlike Cl⁻ which alters the current response in a small range, BSA forms nonconductive polymers with the oxidation product of DIPP on the electrode surface and totally blocks the electrode. The fouling of electrodes and the interference from Cl⁻ ion and BSA are obstacles to achieve a continuous monitor of the concentration of DIPP in plasma, serum or blood. A few solutions are considered. One of them is to extract and detect DIPP in organic solvent.

This idea is based on the facts that DIPP and its oxidation product have higher solubility in organic solvents, and even the mechanism of redox reaction can be different to that in aqueous solution. The fouling of electrodes may be avoidable in organic solvents. By extracting and detecting DIPP in organic solvent, Cl⁻ ion and BSA interference in aqueous solution will also be eliminated. To check the feasibility of this idea, voltammetric response of DIPP has been investigated in acetonitrile, the most frequently used organic solvent in electrochemistry study.

On carbon fiber microelectrode, the electrode fouling still happened in a $10^{-4}$M DIPP acetonitrile solution containing 0.1 M TBAClO4 as supporting electrolyte. But the glassy carbon macroelectrode gave excellent results. Red and blue lines are the first and eighteenth scans, respectively (FIG. 28). A diffusive oxidation peak was observed, and the peak current decay seen after eighteen scans is very small (~7%). The comparison of diffusive peak in acetonitrile solution and surface-confined peak in aqueous solution suggest a different reaction mechanism.

Example 4—Glassy Carbon PVC-Coated Electrode and Use for Propofol Detection

The carbon microelectrodes currently in use were manufactured by lithography methods and by hand fabrication of an electrochemical cell for this purpose. In this design, three microelectrodes were sealed into three glass capillaries and combined into a 3-electrode array. The tip of the microelectrode array and the microfabricated alternative are shown (FIG. 29). The non-aqueous phase is a highly plasticized PVC film on the top of a three electrode electrochemical cell. The large surface Pt and Ag electrodes serve as counter and reference electrodes below the PVC membrane.

A PVC-oNPOE liquid membrane was used to coat the carbon electrode for an in situ extraction and detection phase. Briefly a thin PVC membrane containing o-NPOE and supporting electrolyte was spin-coated onto the top of a glassy carbon electrode. Measurements of DIPP were made in aqueous samples. The data from these studies strongly indicate that the PVC membrane actively partitions the organic DIPP molecule from solution and can be used to partition free (bioactive) drug from more complex solutions, without requiring an acidic environment. Based upon these findings, several EC sensor designs employing organic PVC-coated membranes were pursued.

The PVC cocktail, containing 18.0% PVC, 72.1% o-NPOE, and 9.9% tetradodecylammonium tetrakis(pentofluorophenyl)borate was prepared and drop cast on the GC electrode surface including the electrode site and insulator. The calculated thickness of the PVC membrane was ~3 microns. The electrode was first characterized in an aqueous solution contained 0.5 mM ferrocene methanol, 8 mM TBAClO4 pH 7.2 PBS. The CV recorded shows a behavior similar to a thin-layer cell (FIG. 30). Considering the diffusion coefficient difference between the PVC membrane and the aqueous solution, the high peak current indicated that the partition coefficient between these two phases is very high. The reverse peak is smaller than the forward peak, which may be caused by the ferrocinium ion transfer at the PVC/water interface during the oxidation of ferrocene methanol.

Similar to its solubilized behavior in ferrocene methanol, hydrophobic Propofol is extracted from the aqueous phase into the PVCoNPOE organic layer on the PVC-coated EC sensor and is detected. FIG. 31 shows the CV of Propofol on a 3 μm-thick organic film-covered GC electrode. The aqueous solution contained $10^{-4}$ M DIPP and 8 mM TBAClO4 and 0.1M phosphate buffer (pH 7.2). CV of DIPP (red line) was recorded on the GC electrode. The blue line is the background CV for the control experiment. The calibration curve from a DIPP concentration of $10^{-6}$M to $10^{-4}$M is shown in the inset and demonstrates a linear concentration/signal relationship.

Example 5—Glassy Carbon PVC-Coated Electrode and Effect of Interfering Agents on Propofol Detection Previous work detecting DIPP in aqueous solutions showed that in the presence of 0.12M NaCl, the anodic peak currents of the conductive film are much lower than those which is were used to determine DIPP concentration. This shows that Cl⁻ ion interfering for the detection of DIPP in pH 7.0 solutions. In addition, in the presence of 4% bovine serum albumin (BSA) in vitro, the anodic current is smaller, and the cathodic and anodic currents of the conductive film were not observed. This implied that the oxidation product may react with the albumin and form a passive film on the electrode surface, which eventually blocks the electrode surface.

Based on these prior results with uncoated sensors, the PVC-coated EC sensors was screened to assess the effect of these interfering agents on sensor function for Propofol detection.

Significant chloride ion interference was observed in the assay with a bare GC electrode in aqueous solution, where Cl⁻ oxidation current appears in the same potential range where DIPP is detected. In the presence of the organic film (PVC-covered GC electrode), DIPP is extracted into the interference is not observed. The CV of DIPP on thin PVC film-covered GC electrodes in the presence of 0.12 M NaCl (red line) and the absence of chloride ion (blue line) are compared in FIG. 32. Other components in the solution are indicated above. These data demonstrate that by employing the thin organic film-covered GC electrodes, the chloride ion interference is essentially eliminated.

Bovine serum albumin (BSA) was found to react with the oxidation product of Propofol and form a passivation layer on the GC electrode in aqueous solution. This passivation layer hindered the successive heterogeneous electron transfer reaction at the electrode/solution interface, and no faraday current for DIPP oxidation was observed. A form of BSA interference was also detected during DIPP detection using thin PVC-o-NPOE film-covered GC electrodes (FIG. 33). Specifically, a decrease in the peak current seen in CV was observed with $10^{-4}$M DIPP solution containing 4% BSA.

In FIG. 34, the time presents the mixing time of BSA and DIPP, and the data at t=0 are from a solution without BSA. The electrode for the measurements of the red points was kept in the stirred solution, while for the blue points a freshly prepared PVC-covered GC electrode was put into the stirred solution 12 min prior to the measurements. The comparison demonstrates that the decreasing current is caused by the adsorption of BSA at the organic/water interface, instead of the binding of DIPP to BSA in aqueous solution. To maintain the oxidation current at GC/organic interface, an anion transfer from the aqueous to organic phase or a cation transfer from organic to aqueous phase is required. In this system, perchlorate ions transfer across the organic/water interface. The adsorbed BSA layer, which is negatively charged at pH 7.2, can hinder the anion transfer, resulting in a reduced current.

To verify the mechanism of BSA interference, the CVs of ferrocenemethanol (FcMeOH) on a PVC-o-NPOE-covered GC electrode were compared in the presence (FIG. 35, red line) and in the absence of 4% BSA (FIG. 35, blue line), after 12 min stirring. In the absence of BSA, FcMeOH is oxidized at GC electrode surface and generated a cation product methanol-ferrocenium, which is relatively hydrophilic, and can diffuse to the organic/water interface and transfer into aqueous phase. The much smaller reverse peak confirms the loss of ferrocenium ions from the organic phase. In this case, the electronic current at GC/organic interface was compensated by the ionic current from perchlorate ions transfer from aqueous phase to organic phase and ferrocenium ions transfer from organic phase to aqueous phase. In the presence of BSA, the absorbed BSA layer hinders the anion transfer, so that the ferrocenium ions contribute more in the ionic current competition. As a consequence, the reduction peak of ferrocenium ion almost disappears.

There are several solutions to the BSA interference problem based on this mechanism. One approach is to apply a size-exclusion layer with negligible BSA adsorption on top of PVC membrane to diminish the BSA adsorption. An alternative to this is eliminating the need for an ionic current across the organic/water interface. This can be achieved when the entire electrochemical cell is arranged within the organic phase. In the current system, the working electrode was in the organic phase, but the reference and counter electrodes were in the aqueous phase. If all the three electrodes are arranged in the organic phase, there is no requirement of ionic current at organic/water interface to maintain the electronic current at GC/organic interface. By using an electrochemical cell in which all three electrodes are in the organic phase, it will not be necessary to add perchlorate ions in the sample solution as in the experiments with the PVC membrane coated GC electrode.

Due to the similarity in molecular structure between Propofol and the commonly used vitamin ascorbate (Vitamin C) and the pain reliever Tylenol® (N-acetyl-p-aminophenol, acetaminophen,) in clinical medicine, the potential for these compounds to interfere with the detection of free Propofol in solution was determined using CV methods. The interference from Vitamin C and Tylenol® were evaluated by adding 0.1 mM ascorbate or 0.1 mM N-acetyl-p-aminophenol to the sample solution with 0.1 mM DIPP, respectively. The presence of these two compounds slightly decreased (−10%) the anodic current of Propofol (FIG. 36). However, this does not create a practical problem in the application of EC Propofol sensing in the clinical environment where Tylenol®, in particular, is commonly used.

Example 6—Construction of Microfluidic Sensor Array

An ex-vivo glass slide biosensor with incorporated measuring and reference electrodes was fabricated using electrode patterning techniques followed by a covering formed with a polyimide insulation. Polydimethylsiloxane (PDMS) based microfluidic channels were then formed over sections of the chip, creating three distinct sampling stations on a single chip. The electrodes are larger than the channel defined by the PDMS covering, making the alignment of the channel easier.

According to one design, the electrode assembly is in the form of a microelectrode array (MEA) that includes 5 µm diameter gold discs that are spaced 50 µm center-to-center and hexagonally arranged (FIG. 37). This microfluidic array device has been fabricated and is suitable for detection of bioavailable Propofol.

According to another design, the electrode assembly is in the form of a microband electrode array that includes 5 µm wide individually addressable bands, 100 µm center-to-center distance (FIG. 38). The bands can optionally be interconnected with a single lead wire like the MEAs. This microfluidic array device has been fabricated and is suitable for detection of bioavailable Propofol.

According to another design, the electrode assembly is in the form of an interdigitated electrode array with 5 µm wide fingers and 5 µm wide gaps (FIG. 39). This microfluidic array device has been fabricated and is suitable for detection of bioavailable Propofol.

The glass slide design can be further optimized by converting to a silicone wafer-based platform. Such chip-based EC platforms can be produced in a cost effective manner and cast with microfluidic manifolds. An example of the wafer being used to fabricate our chip-based designs will permit fabrication of 9 sensors from each wafer.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

An alternative embodiment of an electrochemical sensor places electrode sensors in a flex circuit. FIG. 45A shows a perspective view of a flex circuit 4500. FIG. 45A shows a proximal connection end 4502 and a distal sensor end 4504. FIG. 45B shows a top down view of the flex circuit. FIG. 45C shows a bottom up view of the flex circuit. The connection end 4502 may comprise a radius of 0.073 inches. The flex circuit may comprise an end to end length 4506 of 1.815 inches. Embodiments are not so limited.

FIG. 46A shows a side view of the flex circuit while FIG. 46B provides a blow up illustration of the flex circuit's layered disposition. The flex circuit comprises a first layer 4604 of polyamide film followed by a layer 4606 of adhesive and traces followed by another layer 4608 of polyamide film. The polyamide layers comprise a thickness of 0.002 inches while the adhesive and trace layer comprise a thickness of 0.001 inches. Embodiments are not limited to such dimensions.

FIG. 47 provides a blow up view of the connection end 4502. Note that the connection end features six copper plated through hole vias. Each via may comprise a diameter of 0.10 inches but embodiments are not so limited. Of course, the through hole vias may comprise alternative conductive materials.

FIG. 48A provides a schematized blow up view of a flex circuit connection end 4502 featuring six vias 4802, 4804, 8406, 4808, 4810, 4812. Note that each via is electrically connected to a corresponding conductive trace. The traces run parallel along the length of the flex circuit until such point as they diverge toward respective terminal endpoints at the sensor end 4504 (see FIG. 48B). Each trace may comprise a width (4814) of 0.003 inches, and the width between traces (4816) may comprise 0.005 inches but embodiments are not so limited. The traces may comprise gold or alternative conductive materials.

FIG. 48B shows a schematized blow up of sensor end 4504. The traces terminate at reference electrode 1 4820, working electrode 1 4822, and counter electrode 4824; and at reference electrode 2 4826, working electrode 2 4828, and counter electrode 4824. The sensor end 4504 extends beyond the body of the flex circuit for 0.080 inches and comprises a width of 0.117 inches but embodiments are not so limited.

FIG. 49 shows an embodiment of an electrode array located at the flex circuit sensor end. A first portion of the sensor end 4504 comprises a first working electrode 4902 at the terminal end of trace 4920, a first reference electrode 4906 at the terminal end of trace 4922, and first counter electrode 4904 at the terminal end of trace 4924. A second portion of the sensor end 4504 comprises a second working electrode 4908 at the terminal end of trace 4930, a second reference electrode 4912 at the terminal end of trace 4928, and second counter electrode 4910 at the terminal end of trace 4926.

FIG. 50 shows an embodiment of another electrode array located at the flex circuit sensor end. A first portion of the sensor end comprises a first reference electrode 5002 at the terminal end of trace 5020, a first working electrode 5004 at the terminal end of trace 5022, and first counter electrode 5006 at the terminal end of trace 5024. A second portion of the sensor end comprises a second reference electrode 5012 at the terminal end of trace 5030, a second working electrode 5010 at the terminal end of trace 5028, and a second counter electrode 5008 at the terminal end of trace 5026. Reference, working, and counter electrodes may comprise surface areas of 0.00051, 0.00015, and 0.00096 square inches respectively but embodiments are not so limited.

The connection end 4502 of the flex circuit may couple with a mating connector. FIG. 51 shows an A79108-001 6 Position Male Nano Miniature Circular Connector. The pins of the connector may pass through corresponding vias of the flex circuit connection end 4502. The pins may then be soldered in place. FIG. 52 shows the circular connector soldered and affixed to the surface of a flex circuit connection end. The opposing end of the connector may then be further connected or coupled to wiring. As just one example, a six (6) pin male connector nano circular connector may further connect the mating connector (which is itself soldered on its pin-out side to the flex circuit connection end) to 32 AWG wire surrounded by Polytetrafluoroethylene (PTFE) insulation. The wiring comprises separate conductive pathways corresponding to each pin connection and conductive trace.

The electrical coupling configuration described above couples electrode arrays (shown in FIGS. 49 and 50) to a potentiostat circuit as seen in the block diagram of FIG. 53. Under an embodiment, a Freescale Kinetis Microcontroller Development Board pn FRDM KL05Z 5302 drives the potentiostat circuit. The microcontroller provides a digital to analog converter (DAC) 5304 for supplying current to the electrodes. The DAC supplies current through a 100 kohm resistor 5306 under one embodiment. A buffer component 5308 provides voltage measurements 5310 which are returned to the microcontroller though an analog to digital converter (ADC) 5312. An I2C pin 5314 is connected to an amplifier 5316 for monitoring and controlling the gain of amplifier 5316. The microcontroller provides an analog to digital converter 5318 which connects to the amplifier for measuring current in the potentiostat circuit. FIG. 53 shows switches 5320 for routing current to different electrode locations positioned on the flex circuit and located at tip 5328 of catheter device 5330. The potentiostat is coupled to the catheter device through an IV catheter sensor cable jack 5340.

FIG. 54 shows sensor 1 5406, sensor 2 5404, and reference electrode 5408 under an embodiment. The first sensor 5406 may correspond to a working or counter electrode under an embodiment. The second sensor 5408 may also correspond to a working or counter electrode under an embodiment. The on device electrode array 5002 is coupled to a potentiostat circuit 5410. As seen in FIG. 54, microcontroller 5416 drives 5424 the potentiostat circuit. The ADC component 5412 functions in a manner already described above with respect to the circuit shown in FIG. 53. User controls 5418 may provide a user an interface for setting or altering parameters of the potentiostat circuit. Microcontroller 5416 may also control operation of a controlled infusion pump. Microcontroller may communicate with infusion pump via RS-232 communications on RJ45 connections. Microcontroller 5416 may also deliver data to display interface 5420.

Under an embodiment, a potentiostat circuit is designed to deliver a triangle wave excitation signal to electrodes within a catheter, and measure current delivered. The excitation signal may generated by a digital-analog converter within a Freescale Kinetis KL05 microcontroller. This signal is under one embodiment buffered on the potentiostat board, and routed to the electrodes through a 100 kohm measurement resistor. The potentiostat may also contain two switches for routing the signal to two different electrode sets.

As already described above, the electrochemical sensor described herein may be incorporated into a catheter device. Under an embodiment, an indwelling catheter includes a body and a lumen, and one or more electrochemical sensors secured in the body with at least a portion of the sensors being in communication with either the lumen or externally of the catheter body (such that the sensor(s) are exposed to the interior of a blood vessel). According to an embodiment, the catheter comprises one or more electrochemical sensors. Under an embodiment, these sensors may respectively include a plurality of working electrodes.

A catheter may comprise a body 5502 and a first lumen 5504 as seen in FIG. 55. The catheter may also comprise a securing body 5510 (including second lumen 5512) which includes openings 5520, 5522 at its distal end. FIG. 55 illustrates body 5502, securing body 5510, and flex circuit 5540 prior to assembly. Note the flex circuit comprises a curvature around a longitudinal axis spanning a length of the flex circuit. The radius of curvature along a surface of the flex circuit is approximately equal to the radius of the second lumen 5512. Note that the distal end of the body 5502 and the distal end of securing body 5510 feature a taper. Such taper reduces the outer annular radius of each body while leaving corresponding lumen radii unchanged.

FIG. 56 shows an assembled catheter device 5000. As seen in FIG. 56 the longitudinal axis of the flex circuit is aligned with and parallel to the longitudinal axes of the body and the securing body. In an assembled state (FIG. 56), the body 5502 resides within and is secured to the securing body 5510. FIG. 56 shows that the distal tip of the body extends beyond the distal end of the securing body. FIG. 56 shows that the flex circuit 5540 resides between body and securing body such that a first surface of the flex circuit is adjacent and conforms to the outer surface (i.e. outer circumferential curvature) of the body 5502 while a second surface of the flex circuit is adjacent and conforms to the interior surface (i.e. interior circumferential curvature) of second lumen 5512.

FIG. 56 shows that securing body 5510 exhibits two circular openings 5520, 5522 at its distal end. The first opening resides above a first electrode array while a second opening resides above a second electrode array. The openings provide fluid communication between the electrode arrays and fluid samples external to the catheter device.

FIG. 57 shows a catheter apparatus 5000 connected to a docking component 5702, under an embodiment.

FIG. 58 show a catheter and flex circuit 5810 connected 5812 to and electronics box 5814. The catheter is also connected to an infusion pump 5844. The electronics box provides connections 5816 to other computing devices. The electronics box may also communicate via Bluetooth™ low energy communications with a mobile computing device 5820 running one or more mobile applications 5822. The applications may provide a user with data collected by the catheter and flex circuit and/or provide a user an ability to manipulate parameters of a potentiostat circuit coupled to the flex circuit.

Under an alternative embodiment, FIG. 59 shows a flex circuit with a connection end 5902 and a sensor end 5904. Conductive traces are on the opposing side of the displayed flex circuit. Trace width and space between traces may each comprise 0.0762 mm but embodiments are not so limited. The sensor end is 2.534 mm in length 5906 and includes two electrode arrays but embodiments are not so limited. The width of the flex circuit body may comprise 0.865 mm along a first length 5908 and 1.143 mm along a second length 5910.

FIG. 60 shows a side view of the flex circuit shown in FIG. 59. FIG. 61 comprises a blow up view of a connection end portion 6004 featured in FIG. 60. FIG. 61 comprises a side view illustrating the layered disposition of the connection end 6004 (as seen in FIG. 60). FIG. 61 describes that a via comprises a diameter 6102 of 0.264 mm and a through hole diameter 6104 of 0.213 mm. FIG. 61 also shows that gold conductive traces 6106 comprise a thickness of 0.007 mm (+/−0.002 mm). The connection end and flex circuit also feature a 0.051 mm PCB substrate 6110. The connection end and flex circuit also features a 0.014 mm (+/−0.002) polyamide cured film thickness 6108.

FIG. 62 shows a blow up of a flex circuit connection end 5902, under an embodiment. The connection features conductive vias 6202, 6204, 6206, 6208, 6210, 6212. FIG. 62 shows that each via is connected to a corresponding conductive trace.

FIG. 63 shows a blow up of a flex circuit sensor end 5904, under and embodiment. The flex circuit sensor end includes reference electrode 6302, working electrode 6304, and counter electrode 6306. Spacing between working electrode and reference electrode may comprise 0.060 mm under an embodiment. The flex circuit sensor end also includes reference electrode 6312, working electrode 6310, and counter electrode 6308. Electrodes comprise a length 6314 of 0.762 mm. FIG. 63 illustrates ten vias 6318 which connect electrodes to conductive traces on the opposing side of the flex circuit sensor end. The vias may comprise a diameter of 0.100 mm under an embodiment. Working electrodes may comprise an exposed electrode area of 0.0246 mm^2. Reference electrodes may comprise an exposed electrode area of 0.2323 mm^2 under an embodiment. Counter electrodes may comprise an exposed electrode area of 0.3871 mm^2 under an embodiment.

FIG. 64 shows a flex circuit comprising connection end 6402 and sensor end 6404. The connection end features plated bonding pads or vias for soldering on reverse side to connector pins. Conductive traces reside on the opposing surface of the flex circuit featured in FIG. 64.

FIG. 65A shows a flex circuit comprising connection end 6502 and flex circuit sensor end 6504. The flex circuit sensor end comprises a width 6506 of 2.52 mm. FIG. 65B illustrates a side view of the flex circuit of FIG. 65A. The featured flex circuit is 41.74 mm in length 6510. The sensor end is soldered to a connector. The length 6508 of the connector from pins to opposing mating end surface comprises 6.10 mm under an embodiment.

FIG. 67 shows a flex circuit comprising connection end 6702 and sensor end 6704. The connection end 6702 is soldered to connector 6704.

FIG. 66 shows a blow view of a flex circuit sensor end 6604. The sensor end includes a first array 6610 of electrodes and a second array 6612 of electrodes positioned on an outer circumferential surface of the sensor end.

FIG. 68 shows a connector 6804 soldered to a connection end 6802 of a flex circuit. After soldering, pins are under an embodiment trimmed to 0.020 inches.

FIG. 69 shows a flex circuit comprising a sensor end 6904 and connector 6902 soldered to connection end.

FIG. 70 shows a sensor end of flex circuit comprising reference electrodes 7002, 7012, working electrodes 7004, 7010, and counter electrodes 7006, 7008. The electrodes are connected to corresponding conductive traces on the opposing side.

FIG. 71 shows a sensor end of flex circuit comprising reference electrodes 7110, 7120, working electrodes 7112, 7118, and counter electrodes 7114, 7116. The electrodes are connected to corresponding conductive traces on the opposing side. The flex circuit comprises a polyamide coverlay 7102 of 5-7 µm, a flex substrate 7104 of 0.001 inches and gold and/or palladium 7106 electrode conductive material (of thickness 5-7 µm).

FIG. 72 shows a sensor end of flex circuit comprising reference electrodes 7202, 7012, working electrodes 7204, 7210, and counter electrodes 7206, 7208. The electrodes are connected to corresponding conductive traces on the opposing side.

FIG. 73 shows a flex circuit comprising a sensor end 7302 and a connection end 7304. The connection end is soldered to a connector.

FIG. 74 shows a catheter device 7400. A distal end 7408 of the catheter device comprises the flex circuit sensor end 7414. The flex circuit connection end 7410 is soldered to connector 7412. A coupling mechanism 7420 connects the connector to wiring. FIG. 74 also shows shrink tubing (0.001 inches) 7450 and a flex PCB assembly 7460.

FIG. 75 shows conductive traces 7514 on a surface of a flex circuit sensor end. A lower surface of the sensor end comprises reference electrodes 7500, 7512, working electrodes 7504, 7510, and counter electrodes 7506, 7508. The electrodes are connected to corresponding conductive traces on the upper surface.

The traces are under an embodiment located on the opposite side of the polyimide flex circuit substrate. They may connect with the electrode pads by way of full thickness holes (or "vias") in the polyimide.

By moving the traces to the other side of the substrate the traces are under an embodiment effectively insulated from the blood and from the electrode pads to improve sensor performance and minimize risk of drug oxidation at sites other than the exposed pads.

The size of the working electrode is under an embodiment significantly reduced relative to the reference electrode and counter electrode. This size differential optimizes (maximizes) the sensitivity of the electrode in 3 ways; 1) it minimizes the consumption of the drug being measured improving the accuracy of the measurement, 2) small size makes the diffusion more "spherical" than linear and thus the steady state signal is more stable and accurate, 3) small size reduces interference and voltage drop, making the signal more accurate The 3-electrode pads are duplicated to provide 2 sites for measurement on each catheter. These pad sets are under an embodiment 180 degrees apart on the catheter cannula.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The method and device for detection of bioavailable drug concentration in a fluid sample can be a component of a single system, multiple systems, and/or geographically separate systems. The method and device for detection of bioavailable drug concentration in a fluid sample can also be a subcomponent or subsystem of a single system, multiple systems, and/or geographically separate systems. The components of method and device for detection of bioavailable drug concentration in a fluid sample can be coupled to one or more other components (not shown) of a host system or a system coupled to the host system.

One or more components of the method and device for detection of bioavailable drug concentration in a fluid sample and/or a corresponding interface, system or application to which the method and device for detection of bioavailable drug concentration in a fluid sample is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include method and device for detection of bioavailable drug concentration in a fluid sample can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the method and device for detection of bioavailable drug concentration in a fluid sample and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the method and device for detection of bioavailable drug concentration in a fluid sample and corresponding systems and methods include: microcontrollers with memory (such as electronically erasable programmable read only memory (EEPROM)), embedded microprocessors, firmware, software, etc. Furthermore, aspects of the method and device for detection of bioavailable drug concentration in a fluid sample and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the method and device for detection of bioavailable drug concentration in a fluid sample is not intended to be exhaustive or to limit the systems and methods to the precise forms disclosed. While specific embodiments of, and examples for, the method and device for detection of bioavailable drug concentration in a fluid sample and corresponding systems and methods are described herein for illustrative purposes, various equivalent modifications are possible within the scope of the systems and methods, as those skilled in the relevant art will recognize. The teachings of the method and device for detection of bioavailable drug concentration in a fluid sample and corresponding systems and methods provided herein can be applied to other systems and methods, not only for the systems and methods described above.

The elements and acts of the various embodiments described above can be combined to provide further embodiments. These and other changes can be made to the method and device for detection of bioavailable drug concentration in a fluid sample and corresponding systems and methods in light of the above detailed description.

Example 7

The intravenous drug 2,6-diisopropylphenol (propofol) is a general anesthetic which is widely used in many surgical and critical care settings for the purpose of general anesthesia or conscious sedation (Krasowski et al., J Pharm Exp Therap 297:338-351 (2001)). The broad appeal and popularity of propofol is related to the rapid induction and rapid elapse of anesthesia. The target steady-state concentration range of propofol in blood is between 0.25-2.0 µg/mL or 1-12 µM. In general, these target values are set by constant infusion rates ranging between 0.3-3.0 mg/kg/h.

Propofol infusion syndrome (PRIS) is a well-known adverse event that is associated with high doses and long term use of propofol (Zaccheo et al., Crit Care Nurse 28: 18-25 (2008); McKeage and Peny, CNS Drugs 17:235-272 (2003)). It can lead to cardiac and renal failure in critically ill patients and is often fatal. Successful treatment of PRIS requires early recognition and immediate discontinuation of propofol infusion. The propofol related death of Michael Jackson has recently brought the safety of propofol administration into the limelight and underlined the importance of monitoring propofol during anesthesia.

Target-controlled infusion anesthesia (TCIA) aims to provide stable, user-defined, blood concentrations of anesthetic drugs using small-platform delivery systems. The infusion rate of the drug is set by algorithms utilizing population-based pharmacokinetic data and individual patient biometrics (Schnider and Minto, Anaesthesia 63:206 (2008); Coppens et al., Brit J Anaesth 104:452-458 (2010); Struys et al., Anesthesiology 100:640-647 (2004); Stonell et al., Anaesthesia 61:240-247 (2006); Absalom et al., Brit J Anaesth 103:26-37 (2009); Absalom et al., Brit J Anaesth 104:261-264 (2010)). TCIA of propofol is now widely used outside of North America. However, the U.S. Food and Drug Administration (FDA) has not approved TCIA for use in the United States despite numerous studies that have documented excellent patient safety profiles for various forms of anesthesia using this approach (Casati et al., Can J Anaesth 46:235-239 (1999); Chen et al., Eur J Anesth 26:928-935 (2009); Leslie et al., Cochrane Db Syst Rev (2008)). Measuring propofol levels in real-time during anesthesia and correlating blood levels with efficacy data would greatly enhance the safety of propofol delivery and potentially permit the approval of "closed-loop TCIA". To date, real-time measurements of propofol concentration in blood and other biological fluids have been elusive. Instead, most of the efforts are focused on monitoring propofol in the exhaled breath (Grossherr et al., Brit J Anaesth 102:608-613 (2009); Harrison et al., Brit J Anaesth 91:797-799 (2003); Grossherr et al., Anesthesiology 104:786-790 (2006); Miekisch et al., Clin Chim Acta 395:32-37 (2008)) and finding the correlation between the exhaled breath and plasma values (Grossherr et al., Anesthesiology 104:786-790 (2006).

The difficulties for electrochemical quantification of propofol in aqueous solution have been discussed in the literature (Langmaier et al., Anal. Chim. Acta 704:63-67 (2011)). While propofol can be oxidized electrochemically, similar to other phenolic compounds (Azevedo et al., J. Electroanal. Chem. 658:38-45 (2011); Kim et al., Anal. Chim. Acta 479:143-150 (2003); Spataro et al., J. Hazard. Mater. 180:777-780 (2010); Yin et al., Aficrochim. Acta 175:39-46 (2011); Yin et al., Electrochim. Acta 56:2748-2753 (2011); Zejli et al., Anal. Chim. Acta 612: 198-203 (2008)), product(s) from the electrochemical oxidation and coupled reactions may deposit to the electrode surface causing immediate passivation or gradual electrode fouling. Although the detrimental effect of electrode fouling could be minimized, the previously reported detection limit (3.2 µM) and selectivity remained inadequate for monitoring propofol in biological samples. Due to the limited selectivity of voltammetric methods, electrochemical propofol sensors are mainly used as detectors in chromatographic separation (Mazzi et al., J. Chromatogr-Biomed. 528:537-541 (1990); Pissinis et al., J. Liq. Chromatogr. R. T. 30:1787-1795

(2007); Trocewicz et al., J. Chromatogr. B. 685:129-134 (1996)). It is therefore desirable to identify an improved electrochemical sensor that can detect propofol as well as other electrochemically active drugs or metabolites in biological samples across their physiological and therapeutic ranges.

The present invention is directed to overcoming these and other deficiencies in the art.

Example 8—Materials and Methods for Examples 9-11

Materials:

2,6-Di-isopropylphenol (propofol) was purchased from Sigma Aldrich (St. Louis, Mo.) and prepared first as a 10 mM stock solution in 0.1 M NaOH, before diluting to a 1 mM secondary stock solution in phosphate buffer (PBS) for use in the experiments. The PBS buffer (pH 7.2) was prepared as a mixture of 0.1 M KH2P04, 0.1 M KCl and 0.045 M NaOH. All other reagents used in this study were purchased commercially from Sigma Aldrich and were of ACS grade unless stated otherwise. The aqueous solutions were prepared with water purified by a Milli-Q Gradient A 10 System (Millipore Corp., Billerica, Mass.).

Membrane Solutions:

PVC membrane solutions were generally prepared as 250 mg quantities, consisting of 25 wt. % PVC, 50 wt. % plasticizer, 22 wt. % organic electrolyte and 3 wt. % ion-exchange salt. This mixture was then dissolved in 2.5 mL tetrahydrofuran (THF). The PVC (high molecular weight), and its plasticizers: 2-nitrophenyl octyl ether (o-NPOE), bis(2-ethylhexyl) sebacate (DOS) and 1-octanol were selectophore grade. The organic electrolyte, tetradodecylammonium tetrakis(pentafluorophenyl) borate (TDDATPFPhB) was prepared by metathesis reaction between tetradodecylammonium chloride (TDDACl) and potassium tetrakis(pentafluorophenyl) borate (KTPFPhB) (Boulder Scientific Company, Colo.) in dichloromethane, followed by a liquid phase extraction of the product using de-ionized (DI) water. The organic electrolyte, bis(triphenylphosphoranilidine) ammonium tetrakis [3,5,bis (trifluoromethyl) phenyl] borate (BTPPATFPhB) was prepared the same way from bis(triphenylphosphoranylidene) ammonium chloride (BTPPACl) (Sigma Aldrich) and sodium tetrakis[3,5bis(trifluoromethyl) phenyl] borate dihydrate (NaTFPhB) (Dojindo Laboratories Gaithersburg, Md., USA). KTPFPhB also served as the ion-exchange salt, or NaTFPhB was used. The specific compositions of each PVC membrane solution mixture used during the course of this work are described in Table 1. The membrane solutions differ from each other primarily in terms of the plasticizer, the organic electrolyte, or the ion-exchange salt content.

TABLE 1

Composition of PVC Membrane Solutions (wt %) for Spin Coating the GC Electrode Surface. 250 mg quantities were dissolved in 2.5 mL THF

| | | PVC Membrane Solutions | | | | |
|---|---|---|---|---|---|---|
| | | I | II | III | IV | V |
| Polymer | PVC | 25.5 | 25.1 | 25.5 | 25.0 | 25.5 |
| Plasticizer | o-NPOE | 50.9 | | | | |
| | DOS | | 49.9 | 49.6 | 49.8 | |
| | 1-octanol | | | | | 49.5 |
| Electrolyte | TDDATPFPhB | 21.2 | 22.6 | 21.9 | | 21.8 |
| | BTPPATFPhB | | | | 21.8 | |

TABLE 1-continued

Composition of PVC Membrane Solutions (wt %) for Spin Coating the GC Electrode Surface. 250 mg quantities were dissolved in 2.5 mL THF

| | | PVC Membrane Solutions | | | | |
|---|---|---|---|---|---|---|
| | | I | II | III | IV | V |
| Ion-exchange Salt | NaTFPhB | 2.4 | | 3 | 3.4 | 3.2 |
| | KTPFPhB | | 2.4 | | | |
| Solvent | THF | (a) | (b) | (c) | (c) | (c) | tACS grade THF generally contains butylated hydroxytoluene (BHT) as antioxidant. BHT is an electrochemically active compound with very similar structure to propofol. To avoid possible interference from BHT, the THF used to dissolve the membrane solution ingredients was either cleaned by column chromatography (a), or distilled before use (b), or an inhibitor-free (c) THF was used.

Electrodes and Methods:

Cyclic voltammetry (CV) and chronoamperometry (CA) experiments were performed in a 3-electrode cell, using a CH Instruments Model 900 potentiostat (CH Instruments Inc., Tex.). In these measurements Ag|AgCl|3.0 M KCl (CH Instruments) and a platinum wire served as the reference and counter electrode, respectively. The potential of the reference electrode was regularly checked versus a saturated calomel reference electrode. Readings for the Ag/AgCl reference electrode were generally recorded as −35.3/mV in 3.0 M KCl. For details on the theory and application of CV and CA methods the book of Bard and Falkner is recommended (Bard et al., Electrochemical Methods. 2nd ed.; John Wiley & Sons, Inc.: New York (2001), which is hereby incorporated by reference in its entirety.

For the working electrode, a PVC membrane coated glassy carbon (GC) (Ø=3 mm) was used (BASi, IN). The working electrode was first polished (0.3 μm and 0.05 μm alumina slurry), then rinsed and sonicated in DI water, and dried. The electrode was spin-coated with a PVC membrane using a drill press. The electrode was dipped into a PVC membrane solution and rotated for 20 seconds at 1100 rpm and left in an up-right position until the complete evaporation of THF (1 hour). This protocol resulted in a few μm thick PVC membrane coating on the electrode surface. Prior to electrochemical experiments, the PVC membrane-coated electrodes were soaked in PBS for 15 minutes.

Electrochemically oxidizable impurities in the membrane may interfere with the voltammetric determination of the analyte. In the accompanying Examples, impurities in KTPFPhB resulted in an oxidation peak at 1.6 V in the cyclic voltammograms recorded in the background electrolyte. This interference was minimized by implementing an electrochemical pre-treatment protocol in which the potential of the membrane coated electrode was cycled between 0.8 and 1.8 V for 100 scans at 0.1 Vs$^{-1}$ in the background electrolyte prior to exposing the membrane coated sensor to any solution containing propofol, the target analyte. The electrochemical pre-treatment step was no longer required once a high purity KTPFPhB was used for the membrane solutions Example 9—Cyclic Voltammetry with the PVC Membrane Coated GC Electrode In this Example, a plasticized PVC membrane coated GC electrode was used for the measurement of propofol in the presence of interfering compounds at physiologically relevant pH values. As plasticizers, o-NPOE and DOS were used with dielectric constants of 23.9 and 3.9, respectively (Mohr, OPTICAL CHEMICAL SENSORS 297-321, Baldini et al., eds., Springer (2006), which is hereby incorporated by reference in its entirety). Based on previous CV experiments with propofol in acetonitrile, no or minimal electrode fouling was expected when the electrochemical oxidation of propofol is performed in an organic phase.

To perform voltammetric measurements with the plasticized PVC membrane coated electrode, the membranes were prepared with an organic electrolyte (TDDATPFPhB) in combination with an ion-exchange salt (e.g., KTPFPhB), which served as the background electrolyte. Based on the early works of Nieman (Nieman et al., *Analytica Chimica Acta* 170:359-363 (1985), which is hereby incorporated by reference in its entirety) and Amman (Ammann et al., *Analytica Chimica Acta* 171:119-129 (1985), which is hereby incorporated by reference in its entirety), these and similar additives are commonly used to reduce the resistance of liquid membrane ion-selective electrodes. The organic electrolyte has been used in combination with an ion-exchange salt because it provided the lowest resistance (Ammann et al., *Analytica ChimicaActa* 171:119-129 (1985), which is hereby incorporated by reference in its entirety). In general, the primary role of the ion-exchange salt in ion-selective membranes is to improve the permselectivity of the membrane. The permselectivity of the PVC membrane coating during the voltammetric determination of propofol improves the selectivity of the sensor against negatively charged interfering compounds like ascorbate anion. However, in this work the ion exchange salt was incorporated into the membrane with an additional consideration. It was assumed that the oxidation of propofol generates positively charged cationic species, e.g., phenoxonium ions (Morrow, in ORGANIC ELECTROCHEMISTRY, ed. Lund et al., Marcel Dekker, Inc.: New York, Basel (2001), which is hereby incorporated by reference in its entirety) in the membrane, and the excess positive charge is compensated for by the release of hydrophilic cations from the ion exchange salt into the solution.

Cyclic voltammetry (CV) experiments performed with the PVC membrane coated electrode in PBS buffer containing different concentrations of propofol showed a concentration dependent oxidation peak at 1.25 V. The traces of the forward scans recorded at 0.1 Vs$^{-1}$, and the calibration curve constructed from the peak current values are shown in FIG. 84. Using the residual mean standard deviation (RMSD) and slope value (S) of the calibration curve between 40 and 111.1 M, a detection limit (DL) of 8.8 µM was calculated (DL=3× RMSD IS). By considering the reproducibility of the background current (the standard deviation of the background current recorded in three CV scans for the PBS background solution) an improved DL of 2.2 µM (DL=3×STDV/S) was calculated.

CVs recorded with the PVC membrane coated electrode in PBS containing 111.1 µM propofol were very similar to the CVs recorded in acetonitrile. No electrode passivation or decrease in the peak current was detected for a series of continuous scans (6 in total). The peak current increased linearly with propofol concentration. The traces of forward scans recorded at 0.1 Vs$^{-1}$, and the calibration curve constructed from the peak current values at 1.25 V are shown in FIG. 84.

Example 10—Chronoamperometry with the PVC Membrane Coated GC Electrode

For continuous monitoring, chronoamperometry (CA) is a better alternative than CV. In CA experiments the charging current is smaller and the detection limit (DL) is lower. The CA response of three freshly prepared PVC membrane coated sensors for propofol in PBS is shown in FIG. 85 (Table I, solution I). Based on the CV experiments shown in FIG. 84, a potential of 1.2 V was applied vs. Ag|AgCl|3.0 M KCl reference electrode. Propofol concentration of the solution was increased by injecting aliquots of propofol standards at 3 minute intervals into a continuously stirred PBS background solution. As can be seen from FIG. 85, the response of the PVC membrane coated electrode is fast, and the sensor-to-sensor reproducibility is very good. The differences in the slopes of the calibration curves are related to the differences in the thickness of the organic membrane coatings on the GC electrode. Propofol sensors with thicker membrane coatings have reduced sensitivity and slower response compared to sensors with thinner membranes.

Due to concerns about performing voltammetric measurements in a resistive organic film, o-NPOE, which has a relatively large dielectric constant (c:r=23.9) (Mohr, OPTICAL CHEMICAL SENSORS, pp. 297-321, Baldini et al., eds., Springer (2006), which is hereby incorporated by reference in its entirety), was initially used as the plasticizer in the PVC membrane coatings (FIG. 85). However, once it was realized that the resistance of the membrane, due to its small thickness and large organic salt content was not critical, other plasticizers were evaluated. The different membrane coatings resulted in CVs with significantly different peak potentials and peak currents. CA experiments with the DOS plasticized membrane coated GC electrodes were performed with the same protocol as before, but with a different applied potential value.

To study the response of the membrane coated propofol sensor in the presence of easily oxidizable compounds that may interfere with the determination of propofol in whole blood, serum, or plasma, similar triplicate measurements were performed in the presence of 3 mM ascorbic acid (AA) and 1 mM 4-acetamidophenol (APAP). The selected concentrations of AA, APAP, and BSA are at the high end of physiologically relevant concentrations. In these experiments the samples contained also 5% bovine serum albumin (BSA). The influence of albumin on the response of the propofol sensor was tested because albumin is the most abundant plasma protein which may influence the response of an electrochemical sensor when adsorbed to the surface. In addition, it is known that up to 96% of propofol is bound to albumin (Bhattacharya et al., *J. Biol. Chem.* 275:38731-38738 (2000); Schywalsky et al., *Arzneimittel-Forsch.* 55:303-306 (2005), each of which is hereby incorporated by reference in its entirety), i.e., in the presence of albumin the free propofol concentration in the solution is significantly reduced compared to its nominal value.

Propofol detection in the presence of these particular interferents was first evaluated individually and then in a mixture of all three (in order to model measurements recorded in patient's serum or whole blood).

Example 11—Limit of Detection for Propofol with the Membrane-coated Sensor

IUPAC defines the limit of detection as the smallest concentration (or quantity) that can be detected in an analytical procedure with a given certainty (Freiser et al., COMPENDUM OF ANALYTICAL NOMENCLATURE. DEFINITIVE RULES 1987, Blackwell Sci. Publ., Oxford, (1987), which is hereby incorporated by reference in its entirety). This concentration is derived from the mean of the measured signal in the blank (xbi), the standard deviations of the blank measurement (sb;) and the slope of the analytical calibration curve (S) as $c_{DL}^1 = (x_L - \bar{x}_{bi})/S$, where $x_L = \bar{x}_{bi} + 3s_{bi}$.

The detection limit for propofol determination with the membrane coated sensor in cyclic voltammetric experiments (FIG. 84) by considering the standard deviation of the background current recorded in repeated CV scans (n=3) was calculated as $c^1{}_{DL}$=2.2 µM. In monitoring experiments, in addition to the smallest concentration that can be determined, the resolution of the concentration measurements is also very important. The resolution of the measurement is defined as the minimum difference between two concentrations that can be distinguished with a given probability. The resolution of the concentration measurements (cL) in this work has been calculated as $c_{DL}{}^2$=3×RMSD/S, where RMSD is the residual mean standard deviation of the data points of the calibration curve around the best line fit and S is the slope of the fitted line. By considering the peak current values recorded in the CV experiments between 40 and 111.1 µM (FIG. 84 inset) $c^2{}_{DL}$=8.8 µM was calculated. $c^2{}_{DL}$ is greater than $c^1{}_{DL}$ because the scatter of the data points around the best fit line is much larger at high concentrations than at low concentrations.

In FIG. 86A and FIG. 86B, a close-up of the CA response for 1.25 µM propofol in PBS (86A) and in PBS containing 3 mM AA, 1 mM APAP and 5% BSA (86B) is shown in combination with details on the evaluation of cL based on the background current noise. First a line was fitted to a one minute segment of the background current Gust before the first addition of propofol) and the RMSD of the data points around the line was determined (RMSDbgc) (Line A in the figures). Next, a second line was plotted parallel to line A in a distance of 3× RMSDbgc (Line B in FIGS. 86A and 86B). This second line represents a theoretical current response in a solution with a concentration equal to the detection limit of the method. A comparison of the current change recorded upon the addition of 1.25 µM propofol and the current change equal to 3× RMSDbgc (the shift between line A and B in the inset of FIG. 86A) indicates impressive DL values. The detection limits and resolutions for propofol in chronoamperometric measurements using a GC working electrode with different membrane coatings in PBS, and in PBS containing a variety of potential interferences are summarized in Table 2. The resolutions of the CA measurements (cL) were calculated as above, using the slope and the RMSD data of the calibration curve (cL=3×RMSD/S). As shown in FIG. 86B, the interfering compounds increased the background current and decreased the slope of the calibration curves.

In summary, the results in Table 2 show that propofol can be determined in PBS with the plasticized PVC membrane coated GC electrode down to nanomolar concentrations. Sub-micromolar detection limits could be achieved even in the presence of a large excess of easily oxidizable compounds, like AA and APAP. However, in the presence of physiologically relevant levels of albumin the detection limit is shifted towards somewhat larger concentrations. This shift in the DLs toward larger concentrations is a consequence of the decrease in the sensitivity of the measurements in the presence of albumin. The slope of the calibration curves were 6 to 18 times larger in PBS than in the MIXED background electrolyte (PBS with 3 mM AA, 1 mM APAP and 5% BSA) using the DOS or o-NPOE plasticized PVC membranes on the surface of the GC working electrode, respectively. Parallel to the decrease in the slope values in the MIXED background the RMSD values of the calibration points around the regression lines increased which made the calculated resolution of the measurements worse.

A comparison of the compiled values in Table 2 shows that the response range, detection limit ($c^1{}_{DL}$) and resolution ($c^2{}_{DL}$) values were better for the GC electrodes coated by DOS plasticized than o-NPOE plasticized membranes.

Example 12—Selectivity of the Propofol Sensor: Importance of the Partition Coefficients Between the Membrane and the Aqueous Solution To elucidate the impressive detection limit of the propofol sensor in the presence of the most common electrochemical interferences (Table 2), CV scans were recorded both with the bare GC electrode and PVC membrane-coated GC electrode in 3 mM AA and 1 mM APAP solutions. The results of these experiments are shown in FIGS. 87A and 87B. The influence of the PVC membrane coating on the CV response is remarkable in both experiments. No measurable oxidation peak is obtained with the PVC membrane-coated electrode for 3 mM AA and the peak current related to the oxidation of APAP was about 140 times smaller with the PVC membrane-coated electrode in 1 mM APAP solution compared to the bare GC electrode. This large decrease in the sensitivity for AA and APAP compared to an uncoated electrode is obtained because almost no AA or APAP is

TABLE 2

Detection Limits ($c_{DL}{}^1$) and Resolutions ($c_{DL}{}^2$) for Propofol Measurements

| PLASTICIZER | MEMBRANE SOLUTION | BACKGROUND | LINEAR RANGE [µM] | AVG $c_{DL}{}^1$ † [µM] | AVG $c_{DL}{}^2$ † [µM] |
|---|---|---|---|---|---|
| o-NPOE | I | PBS | 0-56.6 | 0.3 ± 0.01 | 1.1 ± 0.2 |
| | I | 3 mM AA * | 0-56.6 | 0.04 ± 0.05 | 2.0 ± 1.0 |
| | I | 1 mM APAP * | 0-56.6 | 0.08 ± 0.02 | 4.6 ± 0.9 |
| | I | 5% BSA * | 5.0-56.6 | 2.2 ± 3.1 | 14.5 ± 1.8 |
| | I | MIXED ‡ | 2.5-109.8 | 0.5 ± 0.4 | 28.2 ± 5.2 |
| DOS | II | PBS | 0-111.1 | 0.12 ± 0.05 | 4.3 ± 0.4 |
| | II | MIXED ‡ | 0-111.1 | 3.0 ± 0.3 | 4.5 ± 2.3 |
| | III | PBS | 0-56.6 | 0.013 ± 0.004 | 5.5 ± 1.4 |
| | III | MIXED ‡ | 0-56.6 | 0.6 ± 0.4 | 4.3 ± 1.2 |
| | IV | PBS | 0-56.6 | 0.022 ± 0.006 | 2.2 ± 0.6 |
| | IV | MIXED ‡ | 9.9-111 | 2.1 ± 1.7 | 12.6 ± 0.2 |

The membrane compositions are provided in Table I. The DL values are provided with their standard deviations (n = 3).
† $c_{DL}{}^1$ = 3 × RMSD$_{bgc}$/S; $c_{DL}{}^2$ = 3 × RMSD/S where RMSD$_{bgc}$ and RMSD were calculated by fitting a line to a section of the background current or the points of the calibration curve, respectively. The slope values (S) were calculated by least square regression in the concentration range quoted as linear range.
‡ MIXED = 3.0 mM AA + 1.0 mM APAP + 5% w/v BSA, in PBS.
* PBS containing ascorbic acid (AA), or 4-acetamidophenol (APAP) or bovine serum albumin (BSA) as interferents.

extracted into the highly hydrophobic membrane, and because the diffusion coefficients are much smaller in the membrane compared to the aqueous solution. The anion exclusion properties of the membranes with KTPFPhB or NaTFPhB content, is an additional benefit with respect of anionic interferences like ascorbate anion. FIG. 88 shows that the chronoamperometric current in a sample with 10 μM propofol remains constant upon the stepwise change of AA concentration in that sample from zero up to 3 mM.

In the cyclic voltammetry experiments with the membrane coated electrode (FIG. 84) the peak currents increased linearly with the square root of the scan rate between 10 and 150 mV/s, and were barely influenced by the rotation rate between 400 and 1600 rpm indicating that the diffusion in the membrane dominates the mass transfer rate. Based on the scan rate dependence of the peak current for the membrane-coated sensor in propofol solutions, it was assumed that the Randles-Sevcik equation (Eq. 6.2.19 in Bard and Falkner, *Electrochemical J Methods*, John Wiley and Sons, New York (2001), which is hereby incorporated by reference in its entirety) can be used to describe the peak current dependence on the concentration. With this assumption, the current ratio measured with the coated and uncoated sensor (Equation 1) can be used to calculate the partition coefficient $$\left(P_{mw} = \frac{c_m}{c_w}\right)$$

of an electrochemically active solute between the membrane and aqueous solution.

$$\frac{i_m}{i_w} = \frac{D_m^{1/2}}{D_w^{1/2}} \cdot \frac{c_m}{c_w} \quad (1)$$

In equation (1), $i_m$ is the peak current recorded with the membrane-coated sensor in an aqueous solution with a concentration of $c_w$; $i_w$ is the peak current measured in the same solution with an uncoated sensor; $D_m$ and $D_w$ are diffusion coefficients of the solute in the membrane and the aqueous solution; and $c_m$ is the concentration of the solute in the membrane. The calculation of $c_m$ and $P_{mw}$ (membrane/water partition coefficient) requires the knowledge of the diffusion coefficient of the solute in the membrane. By using diffusion coefficients measured in ion-selective membranes of similar composition ($D_m = 4 \times 10^{-8}$ cm$^2$/s) (Armstrong et al., *Electrochim. Acta* 35: 1-7 (1990); Bodor et al., *Analyst* 133:635-642 (2008), each of which is hereby incorporated by reference in its entirety) and the experimentally measured $i_w/i_m$ ratio of ~140 (FIG. 88) in combination with $D_w = 8 \times 10^{-6}$ cm$^2$/s (Brookes et al., *J. Phys. Chem. B* 105:6361-6366 (2001), which is hereby incorporated by reference in its entirety) and $C_w = 1$ mM in Equation 1, $P_{mw} = 0.1$ was calculated for APAP, for PVC membrane I (o-NPOE). This is more than an order of magnitude smaller than the octanol/water partition coefficient values for APAP, ranging between $P_{ow} = 2.9$ and $P_{ow} = 1.6$. The partition coefficients calculated for membranes III (DOS) and V (1-octanol) using the same protocol were $P_{mw} = 0.5$ and $P_{mw} = 1.6$, respectively. Weber found a 1:1 correlation between the log $P_{mw}$ and log $P_{ow}$ values for membranes without background electrolyte and ion-exchanger (Chen & Weber, *Anal. Chem.* 79: 1043-1049 (2007), which is hereby incorporated by reference in its entirety). Apparently the high concentration of background electrolyte and ion-exchange salt influence the extraction properties of the membrane.

Example 13—Discussion of Examples 9-12

In the preceding Examples, several organic-film modified GC working electrodes are described for the quantitative assessment of physiologically relevant levels of propofol in serum-like electrolyte solutions. The membrane prevented fouling of the working electrode during propofol detection and improved the selectivity of the sensor due to the large difference in hydrophobicity between the analyte (propofol) and interfering compounds present in the sample, e.g., AA and APAP.

The sensitivity and selectivity of the membrane-coated working electrode for propofol is greatly influenced by the composition of the PVC membrane, i.e., the dielectric properties of the plasticizer, the selection and concentration of the background electrolyte, as well as the incorporation of mobile cation-exchange sites into the membrane, like TPFPhB. The membrane composition also affects the peak potential at which propofol is oxidized in the membrane.

The DL of CA measurements of propofol in PBS buffer (pH 7.2), and in PBS solutions containing 3 mM AA, 1 mM APAP and 5% BSA were 0.03 (±0.01) μM and 0.45 (±0.4) μM, respectively. These values are well below the physiologically relevant target concentrations used during anesthesia or sedation (Grossherr et al., *Brit. J. Anaesth.* 102: 608-613 (2009); Perl et al., *Brit. J. Anaesth.* 103:822-827 (2009), each of which is hereby incorporated by reference in its entirety).

Example 14—Real-Time Monitoring of Propofol

A series of additional experiments were performed using the preferred PVC membrane in a microfluidic detector cell.

FIG. 89 shows the results of a model experiment corresponding to continuous monitoring of propofol in PBS, which models the patient blood. PBS solution was pumped through a flow through detector cell, a Bioanalytical System Inc. flow cell modified to include the PVC membrane (spin-coated) over the electrodes to form an electrochemical cell. Output from the detector cell flowed back into the container. The measured current signal is proportional to the concentration to propofol in the sample in contact with the organic membrane coated electrode or electrochemical cell implemented in the flow through electrochemical cell. After approximately 10 minutes of recording the current signal in PBS without propofol, the propofol concentration in the sample container was increased every 3 minutes through the addition of propofol standard aliquots, while the sensor signal was continuously recorded. As the propofol concentration in the sample container increased the sensor signal also increased. From the steady state current signals recorded at different concentrations, a calibration curve was constructed (inset). Such a calibration curve can be used for the assessment of the propofol concentration in unknown samples.

FIG. 90 shows the results of a similar model experiment discussed in FIG. 89, i.e., a sample container filled with PBS models the patient blood. However, in this experimental model a carrier solution was pumped through the electrochemical flow cell and only small volume aliquots of the sample in the container are metered into the continuously flowing carrier solution. For metering small volume of samples into the carrier stream, sampling valves, also known as injectors, were used. The sample injected into the continuously flowing carrier stream traveled with the carrier through the flow-through electrochemical cell and generated a peak shape transient current signal. The peak height of the transient signal was proportional to the propofol concentration in the injected sample while the peak area was proportional to the total amount of propofol in the sample. This analysis method is known as flow-injection analysis (FIA) (see, e.g., Ruzicka & Hansen, *Flow Injection Analysis*, John Wiley & Sons, New York (1988), which is hereby incorporated by reference in its entirety). The peaks in the figure were recorded following the injection of samples with 0.5, 1, 2.5, 5 and 10 μM propofol concentrations. The inset shows a calibration curve constructed from the peak height-propofol concentration data pairs.

In a follow-up FIA experiment, sequential FIA was used to determine the concentration of propofol in samples. Peaks labeled in FIG. 91 as 1 μM and 10 μM correspond to the injection of 1750 μL volume standard serum like solutions into a continuously flowing carrier steam as above. (Experimental conditions: Sample volume, 175 μL; Flow rate, 0.53 mL/min; applied potential, 1.2 V.) These injections were performed before the monitoring of propofol in model patient serum was started. The peak heights of these two transients were used to construct a two-point calibration curve. Once the calibration was finished, the monitoring experiment started. In the example of FIG. 91, for purposes of this model the patient serum propofol concentration remained constant at 6 μM concentration (which is expected to be achievable using, e.g., TCI). In the example, the 5% BSA containing sample was injected 12 times in the carrier stream with 5 minutes interval to determine the reproducibility of the propofol sensor when it is used in an automated analyzer in flow injection mode. The relative standard deviation was 15%.

In a final experiment, human serum (HSA) or 5% BSA containing electrolyte solution (simulating serum) with different concentrations of propofol were pumped through the electrochemical flow cell while the current signal of the organic membrane coated propofol sensor was continuously recorded. (Experimental conditions: Flow rate, 0.317 mL/min; applied potential, 1.2 V.) The inset to FIG. 92 shows the calibration curves constructed from the steady state current propofol concentration data pairs. FIG. 92 confirms that the 5% BSA containing standards can be used to assess the concentration in human serum samples.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An electrochemical voltammetric sensor device comprising,
a body comprising a first lumen;
a securing body comprising a second lumen;
a flexible circuit comprising a connection end and a sensor end, wherein the flexible circuit comprises a flexible strip of material; wherein the flexible strip of material comprises a first layer and a second layer, wherein the first layer and the second layer comprise polyamide;
the connection end comprising a plurality of vias;
the sensor end comprising an electrochemical sensor, wherein the electrochemical sensor comprises a first array of electrodes, wherein the first array of electrodes are electrically connected to the vias using conductive traces, wherein the first array of electrodes comprises a water-immiscible coating that surrounds the first array of electrodes, wherein the coating partitions a hydrophobic drug from a fluid sample;
wherein the body resides within the second lumen of the securing body, wherein an upper surface of the flexible circuit is adjacent and conforms to an interior circumferential curvature of the second lumen,
wherein a lower surface of the flexible circuit is adjacent and conforms to an exterior circumferential curvature of the body;
the securing body comprising a first opening positioned above the first array of electrodes,
wherein the first opening exposes the first array of electrodes to the fluid sample.

2. The electrochemical voltammetric sensor device of claim 1, wherein the flexible strip of material comprises a third layer between the first and the second layer, wherein the third layer comprises adhesive and the conductive traces.

3. The electrochemical voltammetric sensor device of claim 1, wherein pins of a mating connector pass through corresponding vias of the connection end, wherein the pins and the connection end are joined by soldering the pins to the corresponding vias.

4. The electrochemical voltammetric sensor device of claim 1, wherein the mating connector couples the vias to a potentiostat circuit which controls voltage and current supplied to the electrochemical sensor.

5. The electrochemical voltammetric sensor device of claim 1, wherein the electrochemical sensor comprises a second array of electrodes, wherein the second array of electrodes are electrically connected to the vias using conductive traces, wherein the second array of electrodes comprises the water-immiscible coating that surrounds the second array of electrodes, wherein the coating partitions the hydrophobic drug from the fluid sample.

6. The electrochemical voltammetric sensor device of claim 1, the securing body comprising a second opening positioned above the second array of electrodes, wherein the second opening exposes the second array of electrodes to the fluid sample.

7. The electrochemical, voltammetric sensor device of claim 6, wherein the hydrophobic drug is oxidized within the coating, wherein at least one of the first array of electrodes and the second array of electrodes measure an oxidation/reduction current within the coating, and wherein the measured oxidation/reduction current correlates to the amount of the hydrophobic drug partitioned into the coating.

8. The electrochemical, voltammetric sensor device of claim 1, wherein the coating further comprises a membrane resistance controlling component selected from the group consisting of lipophilic electrolytes, tetradodecyl ammonium-tetrakis(4-chlorophenyl) borate (ETH500), and bis(triphenylphoranylidene) ammonium tetrakis[3,5-bis(trifluoromethyl) phenyl] borate (BTPPATFPB); a biocompatibility enhancing component selected from the group consisting of nitric-oxide releasing sol-gel materials, N-(6-aminohexyl) aminopropyltrimethoxysilane, and balanced isobutyltrimethoxysilane diazeniumdiolate; or both.

9. The electrochemical, voltammetric sensor device of claim 1, wherein the coating comprises PVC, o-NPOE, and TDATPFPB.

10. The electrochemical, voltammetric sensor device of claim 1, wherein the coating is less than about 200 μm thick.

11. An electrochemical voltammetric sensor device comprising, a body comprising a first lumen;
a securing body comprising a second lumen;
a flexible circuit comprising a connection end and a sensor end;
the connection end comprising a plurality of vias; wherein pins of a mating connector pass through corresponding vias of the connection end, wherein the pins and the connection end are joined by soldering the pins to the corresponding vias;
the sensor end comprising an electrochemical sensor, wherein the electrochemical sensor comprises a first array of electrodes, wherein the first array of electrodes are electrically connected to the vias using conductive traces, wherein the first array of electrodes comprises a water-immiscible coating that surrounds the first array of electrodes, wherein the coating partitions a hydrophobic drug from a fluid sample;
wherein the body resides within the second lumen of the securing body, wherein an upper surface of the flexible circuit is adjacent and conforms to an interior circumferential curvature of the second lumen;
wherein a lower surface of the flexible circuit is adjacent and conforms to an exterior circumferential curvature of the body; and
wherein the securing body comprises a first opening positioned above the first array of electrodes, wherein the first opening exposes the first array of electrodes to the fluid sample.

12. The electrochemical voltammetric sensor device of claim 11, wherein the flexible strip of material comprises a first layer and a second layer, wherein the first layer and the second layer comprise polyamide.

13. The electrochemical voltammetric sensor device of claim 12, wherein the flexible strip of material comprises a third layer between the first and the second layer, wherein the third layer comprises adhesive and the conductive traces.

14. The electrochemical voltammetric sensor device of claim 11, wherein the mating connector couples the vias to a potentiostat circuit which controls voltage and current supplied to the electrochemical sensor.

15. The electrochemical voltammetric sensor device of claim 11, wherein the electrochemical sensor comprises a second array of electrodes, wherein the second array of electrodes are electrically connected to the vias using conductive traces, wherein the second array of electrodes comprises the water-immiscible coating that surrounds the second array of electrodes, wherein the coating partitions the hydrophobic drug from the fluid sample.

16. The electrochemical voltammetric sensor device of claim 11, the securing body comprising a second opening positioned above the second array of electrodes, wherein the second opening exposes the second array of electrodes to the fluid sample.

17. The electrochemical voltammetric sensor device of claim 16, wherein the hydrophobic drug is oxidized within the coating, wherein at least one of the first array of electrodes and the second array of electrodes measure an oxidation/reduction current within the coating, and wherein the measured oxidation/reduction current correlates to the amount of the hydrophobic drug partitioned into the coating.

18. The electrochemical voltammetric sensor device of claim 11, wherein the coating further comprises a membrane resistance controlling component selected from the group consisting of lipophilic electrolytes, tetradodecyl ammonium-tetrakis(4-chlorophenyl) borate (ETH500), and bis(triphenylphoranylidene) ammonium tetrakis[3,5-bis(trifluoromethyl) phenyl] borate (BTPPATFPB); a biocompatibility enhancing component selected from the group consisting of nitric-oxide releasing sol-gel materials, N-(6-aminohexyl) aminopropyltrimethoxysilane, and balanced isobutyltrimethoxysilane diazeniumdiolate; or both.

19. The electrochemical voltammetric sensor device of claim 11, wherein the coating comprises PVC, o-NPOE, and TDATPFPB.

20. The electrochemical voltammetric sensor device of claim 11, wherein the coating is less than about 200 µm thick.

* * * * *